United States Patent
Madiyalakan et al.

(10) Patent No.: US 7,318,921 B2
(45) Date of Patent: *Jan. 15, 2008

(54) THERAPEUTIC COMPOSITIONS THAT ALTER THE IMMUNE RESPONSE

(75) Inventors: Ragupathy Madiyalakan, Edmonton (CA); Antoine Noujaim, Edmonton (CA); Birgit Schultes, Arlington, MA (US); Richard Baum, Hargesheim (DE)

(73) Assignee: AltaRex Medical Corp., Edmonton, Alberta (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/376,604

(22) Filed: Aug. 18, 1999

(65) Prior Publication Data

US 2002/0048586 A1     Apr. 25, 2002

Related U.S. Application Data

(63) Continuation-in-part of application No. PCT/IB99/01114, filed on Jun. 15, 1999, which is a continuation-in-part of application No. 09/152,698, filed on Sep. 2, 1998, which is a continuation-in-part of application No. 09/094,598, filed on Jun. 15, 1998, now abandoned, which is a continuation-in-part of application No. 08/877,511, filed on Jun. 17, 1997, now Pat. No. 6,086,873, which is a continuation-in-part of application No. PCT/IB96/00461, filed on May 15, 1996.

(51) Int. Cl.
*A61K 39/00* (2006.01)
*A61K 39/395* (2006.01)

(52) U.S. Cl. .............. 424/130.1; 424/133.1; 424/134.1; 424/135.1; 424/138.1; 424/141.1; 424/178.1

(58) Field of Classification Search ............. 424/130.1, 424/131.1, 138.1, 141.1, 152.1, 174.1
See application file for complete search history.

(56) References Cited

U.S. PATENT DOCUMENTS

| | | | |
|---|---|---|---|
| 3,865,689 A | 2/1975 | Goldenberg | 195/1.7 |
| 4,331,647 A | 5/1982 | Goldenberg | 424/1 |
| 4,740,371 A | 4/1988 | St. Remy et al. | |
| 4,879,225 A | 11/1989 | Morgan, Jr. et al. | |
| 5,053,224 A | 10/1991 | Koprowski et al. | 424/85.8 |
| 5,165,922 A | 11/1992 | Hellstrom et al. | 424/85.8 |
| 5,512,283 A | 4/1996 | Byers et al. | |
| 5,532,159 A * | 7/1996 | Webb et al. | 435/344.1 |
| 5,583,202 A | 12/1996 | Zanetti | |
| 5,591,593 A | 1/1997 | Courtenay-Luck | |
| 5,652,114 A | 7/1997 | Chu et al. | |
| 5,688,657 A | 11/1997 | Tsang et al. | |
| 5,725,856 A * | 3/1998 | Hudziak et al. | 424/130.1 |
| 5,869,445 A | 2/1999 | Cheever et al. | |
| 5,977,315 A * | 11/1999 | Chatterjee et al. | 530/387.2 |
| 6,068,830 A | 5/2000 | Diamandis et al. | |
| 6,077,519 A | 6/2000 | Storkus et al. | |
| 6,096,289 A * | 8/2000 | Goldenberg | 424/1.49 |
| 6,140,091 A | 10/2000 | Raso et al. | |
| 6,241,985 B1 * | 6/2001 | Madiyalakan et al. | |

FOREIGN PATENT DOCUMENTS

| | | |
|---|---|---|
| EP | 0 234 122 A2 | 9/1987 |
| EP | 0 308 208 A1 | 3/1989 |
| WO | WO 87/00053 | 1/1987 |
| WO | WO 88/03954 | 6/1988 |
| WO | WO 89/05140 | 6/1989 |
| WO | WO95/04548 | 2/1995 |
| WO | WO98/57661 | 12/1998 |

OTHER PUBLICATIONS

Madiyalakan et al (Hybridoma, Apr. 1995, vol. 14(2):199-203.*
Baum et al (Hybridoma, 1993, vol. 12(5):583-9.*
Baum et al (Cancer Supplement, 1994, vol. 73(3):1121-1125).*
Baum et al. (Hybridoma, vol. 12, No. 5, 1993, pp. 583-589).*
Madiyalakan et al. (Hybridoma, vol. 14, No. 2, May 19, 1995).*
Ward et al., "Unconjugated antibodies for cancer therapy: lessons from the clinic", Cancer Treatment Reviews, 1997, vol. 23, pp. 305-319.*
Leitzel et al. Elevated Soluble c-erbB-2 Antigen Levels in the Serum and Effusions of a Proportion of Breast Cancer Patients, Jnl.Clin.Oncol., 1992, vol. 10. No. 9, pp. 1436-1443.*
Clark (Protein Engineering of Antibody Molecules for Prophylactic and Therapeutic Applications in Man, 1993, p. 1).*
Kedar and Klein ('Cancer Immunotherapy' In: Advances in Cancer Research, 1992, vol. 59, pp. 245-323.*
Schultze et al (Trends in Immunology, 2004, vol. 25, pp. 659-664).*
Bodey et al, (Anticancer Research, 2000, vol. 20, pp. 2665-2676).*
Abstract of Semino et al (Journal of Biological Regulators and Homeostatic Agents, 1993, vol. 7, pp. 99-105).*
Abstract of Algarra et al, International Journal of Clinical and Laboratory Research, 1997, vol. 27, pp. 95-102.*
Paul, Fundamental Immunology, (text), 1993.*
Ohlen et al (Journal of Immunology, 2001, vol. 166, pp. 2863-2870.*
Lee et al, Journal of Immunology, 1999, vol. 163, pp. 6292-6300.*
Benichou et al, 1994, vol. 6, pp. 131-138.*
Abstract of Pani et al (Immunological Investigations, 1994, vol. 23, pp. 337-346.*
Sotomayor et al, Critical Reviews in Oncogenesis, 1996, vol. 7, pp. 433-456.*
Nishimura et al, Cancer Chemother Pharmacol, 2000, vol. 46, suppl. pp. S52-S61.*
PCT International Search Report Corresponding To PCT International Application No. PCT/IB99/01114; Authorized Officer: M. Covone; Date of Completion: Nov. 30, 1999; Date of Mailing: Dec. 15, 1999 (8 pages).
Madiyalakan, R. et al., HYBRIDOMA, vol. 14, No. 2, 1995, "Antiidiotype Induction Therapy: Evidence for the Induction of Immune Response through the Idiotype Network in Patients with Ovarian Cancer after Administration of Anti-CA 125 Murine Monoclonal Antibody B43.13", pp. 199-203.

(Continued)

*Primary Examiner*—Karen A. Canella
(74) *Attorney, Agent, or Firm*—Ropes & Gray LLP

(57) ABSTRACT

The invention is therapeutic methods and compositions that alter the immunogenicity of the host.

76 Claims, 11 Drawing Sheets

OTHER PUBLICATIONS

Leveugle, B. et al., Proceedings of the American Associate for Cancer Research Annual Meeting, vol. 39, Mar. 1998, "PSA-directed immunotherapy of prostate cancer.", p. 355, (1 page).

Chattopadhyay et al., "Human high molecular weight-melanoma associated antigen mimicry by an anti-idiotypic antibody: characterization of the immunogenicity and the immune response to the mouse monoclonal antibody IMel-1," Cancer Res., 5:6045-51 (1991).

Clark, Protein Engineering of antibody Molecules for Prophylactic and therapeutic Applications in Man, (monograph), Prot. Eng., 1 (1993).

Crowley et al., "Dendritic cells are the principal cells in mouse spleen bearing immunogenic fragments of foreign proteins", J. Exp. Med., 172:383-386 (1990).

De la Salle, "FcγR on Human Dendritic Cells", Human IgG Receptors, p. 39-55 (1996).

Fagerberg, "Humoral anti-idiotypic and anti-anti-idiotypic immune response in cancer patients treated with monoclonal antibody 17-1A," Cancer Imm., 12:81-87 (1996).

Frodin et al., "Induction of anti-idiotypic (ab2) and anti-anti-idiotypic (ab3) antibodies in patients treated with the mouse monoclonal antibody 17-1A (ab1). Relation to the clinical outcome—an important antitumoral effector funtion?," 10:421-31 (1991).

Goldenberg et al., "Cancer Diagnosis and Therapy with Radiolabeled Antibodies", In: Immunoconjugates, Antibody Conjugates in Radioimaging and Therapy of Cancer, Vogel. Ed., 259-280 (1987).

Keder et al., "Cancer Immunotherapy: Are the results discouraging? Can they be improved?", Adv. Cancer Res., 59:245-323 (1992).

Abbas AK et al., "Antigen presentation by B lymphocytes," *Antigen Presenting Cells: Diversity, Differentiation, and Regulation* 269-279 (1988).

Adams S et al., "Comparison of metabolic and receptor imaging in recurrent medullary thyroid carcinoma with histopathological findings," *Eur J Nucl Med.* 25(9):1277-83 (1998).

Alzona M et al., "IL-12 activates IFN-gamma production through the preferential activation of CD30+ T cells," *J Immunol.* 154(1):9-16 (1995).

American Cancer Society, "Cancer Facts and Figures," Atlanta, GA: American Cancer Society (1995).

Andersson K et al., "Modulation of antigen-antibody complexations by immunoglobulins," *Scand J Immunol.* 42(4):407-17 (1995).

Bachmann MF et al., "Regulation of IgG antibody titers by the amount persisting of immune-complexed antigen," *Eur J Immunol.* 24(10):2567-70 (1994).

Barnd DL et al., "Specific, major histocompatibility complex-unrestricted recognition of tumor-associated mucins by human cytotoxic T cells," *Proc Natl Acad Sci U S A.* 86(18):7159-63 (1989).

Bartoloni C et al., "Assay, isolation and characterization of circulating immune complexes from serum of gastrointestinal cancer, stage III and IV melanoma and chronic inflammatory bowel disease patients," *Oncology* 50(1):27-34 (1993).

Bast RC Jr. et al., "A radioimmunoassay using a monoclonal antibody to monitor the course of epithelial ovarian cancer," *New England J. Med.* 309(15):883-7 (1983).

Baum RP et al., "Activating anti-idiotypic human anti-mouse antibodies for immunotherapy of ovarian carcinoma," *Cancer* 73(3 Suppl):1121-5 (1994).

Bernard NF et al., "Possible Role for Specific Surface Immunoglobulin In Antigen Presentation," *Antigen Presenting Cells: Diversity, Differentiation, and Regulation* 291-300 (1988).

Boon T et al., "Tumor antigens recognized by T lymphocytes," *Annu Rev Immunol.* 12:337-65 (1994).

Brakenhoff RH et al., "Construction and characterization of the chimeric monoclonal antibody E48 for therapy of head and neck cancer," *Cancer Immunol Immunother.* 40(3):191-200 (1995).

Bretscher PA et al., "Establishment of stable, cell-mediated immunity that makes "susceptible"mice resistant to Leishmania major," *Science* 257(5069):539-42 (1992).

Brockmeyer NH et al., "Immunomodulation of cimetidine in healthy volunteers," *Klin Wochenschr.* 67(1):26-30 (1989).

Bouige P et al., "Immune complexes as immunizing agents to increase the number of monoclonal antibody producing hybrids and to deviate the response to poorly immunogenic epitopes," *Hybridoma* 9(6):519-26 (1990).

Bukowski RM et al., "Phase I trial of continuous infusion interleukin-2 and doxorubicin in patients with refractory malignancies," *J Immunother.* 10(6):432-9 (1991).

Canevari S et al., "Regression of advanced ovarian carcinoma by intraperitoneal treatment with autologous T lymphocytes retargeted by a bispecific monoclonal antibody," *J Natl Cancer Inst.* 87(19):1463-9 (1995).

Chang CT et al., "Circular dichroic analysis of protein conformation: inclusion of the beta-turns," *Anal Biochem.* 91(1):13-31 (1978).

Chatterjee MB et al., "Idiotypic antibody immunotherapy of cancer," *Cancer Immunol Immunother.* 38(2):75-82 (1994).

Chester SJ et al., "Improved detection of the early stages of colon cancer by determining both free circulating and immune complex-bound antigens reactive with monoclonal antibody," *Cancer Res.* 54(15):3974-8 (1994).

Cheung NK et al., "Antibody response to murine anti-GD2 monoclonal antibodies: correlation with patient survival," *Cancer Res.* 54(8):2228-33 (1994).

Clarke-Pearson DL et al., "Palliative surgery for epothelial ovarian cancer," In Rub SC, Sutton GP eds. *Ovarian Cancer* New York: McGraw-Hill, Inc. 1993: 351-364.

Crum ED, "Effect of cisplatin upon expression of in vivo immune tumor resistance," *Cancer Immunol Immunother.* 36(1):18-24 (1993).

Defoin A et al., "A new liquid phase actinometer: Quantum yield and photo-cidnp study of phenylglyoxylic acid in aqueous solution," *J. Photochem.* 33:237-255 (1985).

DiLeo AJ et al., "High resolution removal of virus from protein solutions using a membrane of unique structure," *Biotechnology* 10(2):182-8 (1992).

DiLeo AJ et al., "Size exclusion removal of model mammalian viruses using a unique membrane system, Part II: Module qualification and process simulation," *Biologicals* 21(3):287-96 (1993).

DiLeo AJ et al., "Sixe exclusion removal of model mammalian viruses using a unique membrane system, Part I: Membrane qualification," *Biologicals* 21(3):275-86 (1993).

Dorai, H et al., "Aglycosylated chimeric mouse/human IgG1 antibody retains some effector function," *Hybridoma* 10:211-7 (1991).

Dohlsten M et al., "Monoclonal antibody-superantigen fusion proteins: tumor-specific agents for T-cell-based tumor therapy," *Proc Natl Acad Sci U S A.* 91(19):8945-9 (1994).

Dohlsten M et al., "Antibody-targeted superantigens are potent inducers of tumor-infiltrating T lymphocytes in vivo," *Proc Natl Acad Sci U S A.* 92 (21):9791-5 (1995).

Donnerstag B et al., "Immunological profile of patients with ovarian cancer under immunostimulation with murine monoclonal antibodies," *International J. of Oncology* 6:853-858 (1995).

Durrant LG et al., "Enhanced cell-mediated tumor killing in patients immunized with human monoclonal antiidiotypic antibody 105AD7," *Cancer Res.* 54(18):4837-40 (1994).

Ehrke MJ et al., "Effects of anticancer drugs on the immune system in humans," *Semin Oncol.* 16(3):230-5 (1989).

Engvall E and Perlman P, " Enzyme-linked immunosorbent assay (ELISA), Quantitative assay of immunoglobulin G." *Immunochemistry* 8:871 (1971).

Fagerberg J et al., "Induction of an immune network cascade in cancer patients treated with monoclonal antibodies (ab1). I. May induction of ab1-reactive T cells and anti-anti-idiotypic antibodies (ab3) lead to tumor regression after mAb therapy?," *Cancer Immunol Immunother.* 37(4):264-70 (1993).

Fagerberg J et al., "Induction of an immune network cascade in cancer patients treated with monoclonal antibodies (ab1). II. Is induction of anti-idiotype reactive T cells (T3) of importance for tumor response to mAb therapy?," *Cancer Immunol Immunother.* 38(3):149-59 (1994).

Fagerberg J et al., "Tumor regression in monoclonal antibody-treated patients correlates with the presence of anti-idiotype-reactive T lymphocytes," *Cancer Res.* 55(9):1824-7 (1995).
Fendrick JL et al., "Characterization of CA 125 synthesized by the human epithelial amnion WISH cell line," *Tumour Biol.* 14(5):310-8 (1993).
Gadducci A et al., "Serum half-life of CA 125 during early chemotherapy as an independent prognostic variable for patients with advanced epithelial ovarian cancer: results of a multicentric Italian study," *Gynecol Oncol.* 58(1):42-7 (1995).
Gallagher G and Al-Azzawi F, "Adoptive immunotherapy of experimental ovarian cancer using activated human monocytes and the human monoclonal antibody, anti-14C1," *Intl J of Oncology* 5:253-258 (1994).
Gallagher G et al., "Multiple epitopes of the human ovarian cancer antigen 14C1 recognised by human IgG antibodies: their potential in immunotherapy," *Br J Cancer* 64(1):35-40 (1991).
Geffner JR et al., "Activation of human neutrophils and monocytes induced by immune complexes prepared with cationized antibodies or antigens," *Clin Immunol Immunopathol.* 69(1):9-15 (1993).
Goldenberg DM "New developments in monoclonal antibodies for cancer detection and therapy," *CA Cancer J Clin.* 44(1):43-64 (1994).
Goronzy J et al., "Long-term humoral unresponsiveness in vivo, induced by treatment with monoclonal antibody against L3T4," *J Exp Med.* 164(3):911-25 (1986).
Handgretinger R et al., "A phase I study of human/mouse chimeric antiganglioside GD2 antibody ch14.18 in patients with neuroblastoma," *Eur J Cancer.* 31A(2):261-7 (1995).
Hariharan K eta l., "The induction of cytotoxic T cells and tumor regression by soluble antigen formulation," *Cancer Res.* 55(16):3486-9 (1995).
Harris JE and Braun DP, "Abnormal Immunoregulation and the tumor dormant state in human cancer," In: Stewart THM, Wheelock eds. Cellular immune mechanisms and tumor dormancy, Boca Raton, Florida: CRC Press 261-276 (1992).
Hoskins PJ et al., "Ten-year outcome of patients with advanced epithelial ovarian carcinoma treated with cisplatin-based multimodality therapy," *J Clin Oncol.* 10(10):1561-8 (1992).
Hozumi N and Sandhu JS, "Recombinant antibody technology: its advent and advances," *Cancer Invest.* 11(6):714-23 (1993).
Hayat MA, *Colloidal Gold: Principles, Methods, and Applications* vol. 1, San Diego: Academic Press, Inc. 1989.
Ioannides CG et al., "Cytotoxic T cells from ovarian malignant tumors can recognize polymorphic epithelial mucin core peptides," *J Immunol.* 151(7):3693-703 (1993).
Jacoby RO et al., "Characterization of mouse parvovirus infection by in situ hybridization," *J Virol.* 69(6):3915-9 (1995).
Jensen JL et al., "Possible utility of serum determinations of CA 125 and CA 27.29 in breast cancer management," *Int. J. Biol. Markers* 6:1 (1991).
Jerne NK, "Towards a network theory of the immune system," *Ann Immunol* (Paris) 125C(1-2):373-89 (1974).
Kehoe S, "Cell-mediated immunity and immunotherapy in ovarian cancer (review)," *Intl J of Oncology* 6:451-458 (1995).
Khazaeli MB et al., "Human immune response to monoclonal antibodies," *J. Immunother.* 15(1):42-52 (1994).
Kim HT et al., "Gamma delta T cell recognition of tumor Ig peptide," *J Immunol.* 154(4):1614-23 (1995).
Knuth A et al., "T-cell-mediated cytotoxicity against autologous malignant melanoma: analysis with interleukin 2-dependent T-cell cultures," *Proc Natl Acad Sci U S A* 81(11):3511-5 (1984).
Kobayashi H et al., "Characterization of CA 125 antigen identified by monoclonal antibodies that recognize different epitopes," *Clin Biochem.* 26(5):391-7 (1993).
Kosmas C et al., "Activation of cellular immunity after intracavitary monoclonal antibody therapy of ovarian cancer," *Cancer* 73(12):3000-10 (1994).
Kosmas C et al., "Patients receiving murine monoclonal antibody therapy for malignancy develop T cells that proliferate in vitro in response to these antibodies as antigens," *Br J Cancer* 64(3):494-500 (1991).

FT Kreutz and Suresh MR, "Biospecific monoclonal Anti-CA 125 X Anti-peroxidase antibodies in the measurement of the ovarian carcinoma antigen" *J of Tumor Marker Oncology* 10(1):45-53 (1995).
Lamers CH et al., "Inhibition of bispecific monoclonal antibody (bsAb)-targeted cytolysis by human anti-mouse antibodies in ovarian carcinoma patients treated with bsAb-targeted activated T-lymphocytes," *Int J Cancer* 60(4):450-7 (1995).
Lanzavecchia A, "Identifying strategies for immune intervention," *Science* 260(5110):937-44 (1993).
Lanzavecchia A et al., "Antibodies as antigens. The use of mouse monoclonal antibodies to focus human T cells against selected targets," *J Exp Med.* 167(2):345-52 (1988).
Livingston Po et al., "Sympsoium 10: glucosylation defining malignancy. Effect of active immunization with human tumor associated carbohydrate antigens on the immune response and on tumor growth," *Proc. Am. Assoc. Cancer Research* 36:678 (1995).
Loevinger, RL et al., *MIRD Primer for Absorbed Dose Calculations* New York: Society of Nuclear Medicine, 1991.
Lopes LM and Chain BM, "Liposome-mediated delivery stimulates a class I-restricted cytotoxic T cell response to soluble antigen," *Eur J Immunol.* 22(1):287-90 (1992).
Madiyalakan R et al., "Antiidiotype induction therapy: evidence for the induction of immune response through the idiotype network in patients with ovarian cancer after administration of anti-CA125 murine monoclonal antibody B43.13," *Hybridoma* 14(2):199-203 (1995).
Manca F et al., "Effect of antigen/antibody ratio on macrophage uptake, processing, and presentation to T cells of antigen complexed with polyclonal antibodies," *J Exp Med.* 173(1):37-48 (1991).
Maraveyas A and Epenetos AA, "Targeted immunotherapy. An update with special emphasis on ovarian cancer," *Acta Oncol.* 32(7-8):741-6 (1993).
Martin AC et al., "Modeling antibody hypervariable loops: a combined algorithm," *Proc Natl Acad Sci U S A* 86:9268-72 (1986).
Marusic-Galesic S et al., "Cellular immune response to the antigen administered as an immune complex," *Immunology.* 72(4):526-31 (1991).
Meier W, "CA 125 based diagnosis and therapy in recurrent ovarian cancer," Abstract. *Abstarcts of the Eighth International Hamburg Symposium on Tumor Markers* Hamburg, German 2443 (1995).
Mitchell MS, *Biological Approaches to Cancer Treatment: Biomodulation* New York: McGrawHill, Inc., 1993.
Mitchell MS et al., "Biomodulators in cancer treatment," *J Clin Pharmacol.* 32(1):2-9 (1992).
Mosmann TR and RL Coffman, Two types of mouse helper t-cell clone, Review. *Immunology Today* 8(7 and 8):223-227 (1987).
Muddukrishna SN et al., "Indirect iodometric procedure for quantation of Sn(II) in radiopharmaceutical kits," *Appl. Radial. Isot.* 45(3):293-299 (1994).
Munn DH and Cheung NK "Interleukin-2 enhancement of monoclonal antibody-mediated cellular cytotoxicity against human melanoma," *Cancer Res.* 47(24 Pt 1):6600-5 (1987).
Naramura M et al., "Therapeutic potential of chimeric and murine anti-(epidermal growth factor receptor) antibodies in a metastasis model for human melanoma," *Cancer Immunol Immunother.* 37(5):343-9 (1993).
National Cancer Institute of Canada, "Canadian Cancer Statistics" Toronto: National Cancer Institute of Canada (1998).
Nemazee DA and Sato VL, "Enhancing antibody: a novel component of the immune response," *Proc Natl Acad Sci U S A.* 79(12):3828-32 (1982).
Ohta S et al., "Tumor-associated glycoantigen, sialyl Lewis$^a$ as a target for bispecific antibody-directed adoptive tumor immunotherapy," *Immunol Lett.* 44(1):35-40 (1995).
Ovarian Cancer: Screening, Treatment, and Followup. NIH Consens Statement 12(3):1-30 (1994).
Ozols, MD, PhD, RF "Biologic Treatment of Human Cancer," *Current Problems in Cancer* 19(4):186-261 (1995).
Pederson J et al., "Antibody Modeling: Beyond Homology," *Immunomethods* 1:126-136 (1992).
Perala-Heape M et al., "Effects of tumour mass and circulating antigen on the biodistribution of 111 In-labelled F(ab')2 fragments of human prostatic acid phosphatase monoclonal antibody in nude mice bearing PC-82 human prostatic tumour xenografts," *Eur J Nucl Med.* 18(5):339-45 (1991).

Pierce SK and LA Casten, "Soluble globular protein antigens covalently coupled to antibodies specific for b cell surface structures are effective antigens both in vitro and in vivo," *Antigen presenting cells: diversity, differentiation, and regulation* 259-268 (1988).

Pimm MV, "Circulating antigen: bad or good for immunoscintigraphy?" *Nucl Med Biol.* 22(2):137-45. Review. (1995).

Pimm MV et al., "Influence of syngeneic monoclonal anti-idiotypic antibodies to murine monoclonal antibodies against tumour-associated antigens on the biodistribution of their target antibodies and their fragments," *J Cancer Res Clin Oncol.* 119(7):408-14 (1993).

Pimm MV and Gribben SJ, "Toxicity associated with the formation and clearance of immune complexes between antitumour monoclonal antibodies and syngeneic anti-idiotypic antibodies in mice," *J Cancer Res Clin Oncol.* 119(1):41-5 (1992).

Provencher SW and Glockner J, "Estimation of globular protein secondary structure from circular dichroism," *Biochemistry* 20(1):33-7 (1981).

Randall RE et al., "Purification of antibody-antigen complexes containing recombinant SIV proteins: comparison of antigen and antibody-antigen complexes for immune priming," *Vaccine* 12(4):351-8 (1994).

Riethmuller G et al., "Monoclonal antibodies in cancer therapy," *Curr Opin Immunol.* 5(5):732-9 (1993).

Riethmuller G et al., "Randomised trial of monoclonal antibody for adjuvant therapy of resected Dukes' C colorectal carcinoma," *Lancet* 343(8907):1177-83 (1994).

Ron IG et al., "Use of CA-125 response to predict survival parameters of patients with advanced ovarian carcinoma," *Acta Obstet Gynecol Scand.* 73(8):658-62 (1994).

Roosnek E and A Lanzavecchia, "Efficient and selective presentation of antigen-antibody complexes by rheumatoid factor B cells," *J Exp Med.* 173(2):487-9 (1991).

Schlebusch H et al., "A monoclonal antiidiotypic antibody ACA 125 mimicking the tumor-associated antigen CA 125 for immunotherapy of ovarian cancer," *Hybridoma* 14(2):167-7 (1995).

Schmolling J et al., "Antiidiotypic antibodies in ovarian cancer patients treated with the monoclonal antibody B72.3," *Hybridoma* 14(2):183-6 (1995).

Schultes BC et al., "Idiotypic cascades after injection of the monoclonal antibody OC125: a study in a mouse model. Induction of antibodies against OC125 and CA125 after immunization with an anti-CA 125 (MAb OC125) monoclonal antibody by activation of the idiotypic network," *Eur J Clin Chem Clin Biochem.* 31(7):427-32 (1993).

Sciammas R et al., "TCR gamma delta cells: mysterious cells of the immune system," *Immunol Res.* 13(4):268-79 (1994).

Shitara K et al., "A mouse/human chimeric anti-(ganglioside GD3) antibody with enhanced antitumor activities," *Cancer Immunol Immunother.* 36(6):373-80 (1993).

Snyder et al., *A Tabulation of Dose Equivalent per Microurie-Day for Source and Target Organs of an Adult for Various Radionuclides* Oak Ridge National Laboratory, Oak Ridge Tn (1975).

Spalding BJ, "Few firms pursue anti-ids," *Bio/Technology* 10:950 (1992).

Squire CM et al., "Antigen presentation is enhanced by targeting antigen to the Fc epsilon RII by antigen-anti-Fc epsilon RII conjugates," *J Immunol.* 152(9):4388-96 (1994).

Stevenson FK and RE Hawkins, "Molecular Vaccines Against Cancer," *Immunologist* 2(1):16-19 (1994).

Strieter RM et al., "Cellular and molecular regulation of tumor necrosis factor-alpha production by pentoxifylline," *Biochem Biophys Res Commun.* 155(3):1230-6 (1988).

Sulica A et al., "Regulation of human natural cytotoxicity by IgG. IV. Association between binding of monomeric IgG to the Fc receptors on large granular lymphocytes and inhibition of natual killer (NK) cell activity," *Cell Immunol.* 147(2):397-410 (1993).

Taggart, RT, Samloff IM., "Stable antibody-producing murine hybridomas," *Science* 219:1228-1230 (1983).

Tew JG et al., "Induction of the secondary antibody response: immune complex formation, iccosome release by follicular dendritic cells, processing and presentation of antigen by genminal center b cells and tingible body macrophages," *Progress in Leukocyte Biology* 7:1-10 Alan R Liss, Inc., New York (1988).

Thomson AW and JV Forrester, "Therapeutic advances in immunosuppression," *Clin Exp Immunol.* 98(3):351-7 (1994).

Torbett BE et al., "hu-PBL-SCID mice: a model for human immune function, AIDS, and lymphomagenesis," *Immunol Rev.* 124:139-64 (1991).

Trauth BC et al., "Monoclonal antibody-mediated tumor regression by induction of apoptosis," *Science* 245(4915):301-5 (1989).

Ullman EF et al., "Anti-immune complex antibodies enhance affinity and specificity of primary antibodies," *Proc Natl Acad Sci U S A.* 90(4):1184-9 (1993).

United Nations, Demographic Yearbook, 1992 Forty-fourth issue, New York (1994).

United Nations Population Fund, The State of World Population, 1991.

van der Bruggen P, "The long-standing quest for tumor rejection antigens," *Clin Immunol Immunopathol* 71(3):248-52 (1994).

Vitetta ES and JW Uhr, "Monoclonal antibodies as agonists: an expanded role for their use in cancer therapy," *Cancer Res.* 54(20):5301-9 (1994).

Vose BM and Bonnard GD, "Specific cytotoxicity against autologous tumour and proliferative responses of human lymphocytes grown in interleukin 2," *Int J Cancer* 29(1):33-9 (1982).

Wagner U, "Antitumor antibodies for immunotherapy of ovarian carcinomas," *Hybridoma* 12(5):521-8 (1993).

Wagner U et al., "Clinical courses of patients with ovarian carcinomas after induction of anti-idiotypic antibodies against a tumor-associated antigen," *Tumor Diagnostic & Therapic* 11:1-4 (1990).

Wagner UA et al., "Immunotherapy of advanced ovarian carcinomas by activation of the idiotypic network," *Biotechnol Ther.* 3(1-2):81-9 (1992).

Walker AM et al., "Prolactin-immunoglobulin G complexes from human serum act as costimulatory ligands causing proliferation of malignant B lymphocytes," *Proc Natl Acad Sci U S A.* 92(8):3278-82 (1995).

Wawrzynczak EJ et al., "Blood clearance in the rat of a recombinant mouse monoclonal antibody lacking the N-linked oligosaccharide side chains of the CH2 domains," *Mol Immunol.* 29:213-20 (1992).

Weber D, *MIRD: Radiocuclide Data and Decay Schemes* New York: Society of Nuclear Medicine, 1989.

Wiersma EJ et al., "Enhancement of the antibody response to protein antigens by specific IgG under different experimental conditions," *Scand J Immunol.* 36(2):193-200 (1992).

Wolff EA et al., "Monoclonal antibody homodimers: enhanced antitumor activity in nude mice," *Cancer Res.* 53(11):2560-5 (1993).

Wyatt, PJ "Light scattering and the absolute characterization of macromolecules" Review. *Analytica Chimica Acta* 272:1-40 (1993).

Xu ZY et al., "Overcoming suppression of antitumor immune reactivity in tumor-bearing rats by treatment with bleomycin," *Cancer Res.* 48(23):6658-63 (1988).

Yano S et al., "Natural antibodies against the immunoglobulin F(ab')2 fragment cause elimination of antigens recognized by the F(ab')2 from the circulation," *Eur J Immunol.* 25(11):3128-33 (1995).

Zhang S et al., "Increased tumor cell reactivity and complement-dependent cytotoxicity with mixtures of monoclonal antibodies against different gangliosides," *Cancer Immunol Immunother.* 40(2):88-94 (1995).

Jurncic-Winkler et al., 1993, Clinical evaluation of a new prostate-specific antigen sandwich ELISA which employs four monoclonal antibodies directed at different epitopes of prostate-specific antigen, Eur. Urol. 1993;24(4):487-91.

Paul, 1993, Fundamental Immunol., p. 1163.

Simitsek et al., 1995, Modulation of antigen processing by bound antibodies can boost or suppress class II major histocompatibility complex presentation of different T cell determinants, J. Exp. Med. 181:1957-1963.

VRBA et al., 1975, Carcinoembryonic antigen: evidence for multiple antigenic determinants and isoantigens, Proc. Natl. Acad. Sci. USA 72(11):4602-4606.

Madlyalakan, R. et al., HYBRIDOMA, vol. 14, No. 2, 1995, "Antiidiotype Induction Therapy: Evidence for the Induction of Immune Response through the Idiotype Network in Patients with Ovarian Cancer after Administration of Anti-CA 125 Murine Monoclonal Antibody B43.13", pp. 199-203.

Foon, K.A. et al., Clinical Cancer Research, vol. 3, Aug. 1997, "Clinical and Immune Responses in Advanced Colorectal Cancer Patients Treated with Anti-Idiotype Monoclonal Antibody Vaccine That Mimics the Carcinoembryonic Antigen", pp. 1267-1276.

Uemura, H. et al., Jpn J. Cancer Res., vol. 7, No. 10, 1995, "Generation of anti-idiotype antibodies related to prostatic specific antigen" (meeting abstract), p. 427.

Schultes, B.C. et al., Cancer Immunol Immunother, vol. 46, No. 4, Jun. 1998, "Anti-idiotype induction therapy: anti-CA 125 antibodies ($Ab_3$) mediated tumor killing in patients treated with Ovarex mAb B43.13 ($Ab_1$)", pp. 201-212.

Hertel A et al. "A New Tc-99m Labeled Monoclonal Antibody (B43.13) Against CA 125 For Early Detection of Ovarian Cancer Recurrences—First Clinical Results" The Journal of Nuclear Medicine Abstract Book vol. 33, No. 5 May 1992 p. 904, Abstract No. 338.

White E et al. "Process Validation for Virus Removal and Inactivation" BioPharm May 1991 pp. 34-39.

Klaus, "Antigen-antibody complexes elicit anti-idiotypic antibodies to self-idiotopes," Nature, 272:265-66 (1978).

McGuckin et al., "Circulating tumour-associated mucin concentrations, determined by the CASA assay, in healthy women," Clin. Chim. Acta, 214:139-51 (1993).

Paul, "Factors limiting effective tumor immunity", Fund. Imm., 1163-69 (1993).

Rooijen, "The role of the FDC-retained immune complex network and its dynamics in the activity of germinal centres," Res. Immunol., 144:545-52 (1993).

Sallusto, "Efficient presentation of soluble antigen by cultured human dendritic cells is maintained by granulocyte/macrophage colony-stimulating factor plus interleukin 4 and downregulated by tumor necrosis factor $\alpha$", J. Exp. Med., 179:1109-1118 (1994).

Schlom, In: Molecular foundations of Oncology, S. Broder, Ed., Mol. Fndns. Oncol., 105-107 (1991).

Schwartz, "Cancer Markers," In: Cancer: Principles and Practice of Clinical Oncology, 4th Ed., 531-542 (1994).

Tassi et al., "Immunogenicity of anti-idiotypic antibodies and of their F(ab')2 fragments," Imm. Letts., 27:39-44 (1991).

Ward, "Unconjugated antibodies for cancer therapy: lessons from the clinic" Cancer Treatment Rev., 23:305-319 (1997).

Yin et al., "Serological and immunochemical analysis of Lewis $\gamma$ (Ley) blood group antigen expression in epithelial ovarian cancer," Int. J. Cancer, 65-406-412 (1996).

* cited by examiner

THERAPEUTIC COMPOSITIONS THAT ALTER THE IMMUNE RESPONSE

The application is a continuation-in-part of U.S. Ser. No. 08/877,511, filed Jun. 17, 1997, now U.S. Pat. No. 6,086,873, which is a continuation-in-part of International Application No. PCT/IB96/00461, filed May 15, 1996, now WO 97/42973 A1; a continuation-in-part of U.S. Ser. No. 08/913,290, a U.S. national stage application of International Application No. PCT/IB96/00461, filed under 35 U.S.C. § 371 on Mar. 20, 1998, now U.S. Pat. No. 6,241,985; a continuation-in-part of U.S. Ser. No. 09/152,698, filed Sep. 2, 1998; and a continuation-in-part of PCT/IB99/01114, filed Jun. 15, 1999, now WO 99/65517 A2. U.S. Ser. No. 09/152,698 is also a continuation-in-part of U.S. Ser. No. 08/877,511 (now U.S. Pat. No. 6,086,873), Ser. No. 08/913,290 (now U.S. Pat. No. 6,241,985), and Ser. No. 09/094,598 (filed Jun. 15, 1998, now abandoned, which is a continuation-in-part of both U.S. Ser. No. 08/877,511 and International Application No. PCT/IB96/00461). The teachings of each of these applications are hereby incorporated by reference.

TECHNICAL FIELD

The invention concerns methods and compositions having increased therapeutic effect by altering the immunogenicity of the active component without decreasing the active component's antigenicity. Typically, a beneficial therapeutic effect is derived from altering the state of the immune system, and for some embodiments of the invention, e.g., cancer immunotherapy, immunogenicity is induced, activated, or increased. The invention also concerns methods and compositions for stimulating a host's immune response, particularly for the treatment of cancer. The methods and compositions according to the invention use binding agents such as antibodies to generate an immune response to a pre-determined antigen.

BACKGROUND ART

In vertebrates, the mechanisms of natural and specific immunity cooperate within a system of host defenses, the immune system, to eliminate foreign invaders. The hypothesis that the immune system ought to be able to recognize tumors and thus could be recruited in the fight against cancer has been a driving force behind outstanding efforts of many immunologists. This approach is attractive because of the unique ability of the immune system to specifically destroy affected cells while mostly sparing normal tissue. Moreover, the initial immune response is known to leave behind a long-term memory that serves to protect from the same disease in the future. No drug treatment for cancer can claim such specificity or memory.

An immunotherapeutic strategy for the treatment of cancer and other diseases or conditions involve one or more components of the immune system to trigger a complex cascade of biological reactions focused on eliminating a foreign molecule from the host. Vertebrates have two broad classes of immune responses: antibody responses, or humoral immunity, and cell-mediated immune responses, or cellular immunity.

Humoral immunity is provided by B lymphocytes, which, after proliferation and differentiation, produce antibodies (proteins also known as immunoglobulins) that circulate in the blood and lymphatic fluid. These antibodies specifically bind to the antigen that induced them. Binding by antibody inactivates the foreign substance, e.g., a virus, by blocking the substance's ability to bind to receptors on a target cell or by attracting complement or the killer cells that attack the virus. The humoral response primarily defends against the extracellular phases of bacterial and viral infections. In humoral immunity, serum alone can transfer the response, and the effectors of the response are protein molecules, typically soluble, called antibodies. Lymphocytes produce these antibodies and thereby determine the specificity of immunity; it is this response that orchestrates the effector limbs of the immune system. Cells and proteins, such as antibodies, that interact with lymphocytes play critical roles in both the presentation of antigen and in the mediation of immunologic functions.

Individual lymphocytes respond to a limited set of structurally related antigens. As noted in more detail below, this function is defined structurally by the presence of receptors on the lymphocyte's surface membrane that are specific for binding sites (determinants or epitopes) on the antigen.

Lymphocytes differ from each other not only in the specificity of their receptors, but also in their functions. One class of lymphocytes, B cells, are precursors of antibody-secreting cells, and function as mediators of the humoral immune response.

Another class of lymphocytes, T cells, express important regulatory functions, and are mediators of the cellular immune response. The second class of immune responses, cellular immunity, involve the production of specialized cells, e.g., T lymphocytes, that react with foreign antigens on the surface of other host cells. The cellular immune response is particularly effective against fungi, parasites, intracellular viral infections, cancer cells and other foreign matter. In fact, the majority of T lymphocytes play a regulatory role in immunity, acting either to enhance or suppress the responses of other white blood cells. These cells, called helper T cells and suppressor T cells, respectively, are collectively referred to as regulatory cells. Other T lymphocytes, called cytotoxic T cells, kill, for example, virus-infected cells or tumor cells. Both cytotoxic T cells and B lymphocytes are involved directly in defense against infection and are collectively referred to as effector cells. There are a number of intercellular signals important to T cell activation. Under normal circumstances an antigen degrades or is cleaved to form antigen fragments or peptides. Presentation of At antigen fragments to T-cells is the principal function of MHC molecules, and the cells that carry out this function are called antigen-presenting cells (APC: including but not limited to dendritic cells, macrophages, and B cells).

The time course of an immune response is subdivided into the cognitive or recognition phase, during which specific lymphocytes recognize the foreign antigen; the activation phase, during which specific lymphocytes respond to the foreign antigen; and the effector phase, during which antigen-activated lymphocytes mediate the processes required to eliminate the antigen-carrying target cells. Lymphocytes are immune cells that are specialized in mediating and directing specific immune responses. T cells and B cells become morphologically distinct only after they have been stimulated by an antigen.

The capture and processing of an antigen by APCs is essential for the induction of a specific immune response. APCs capture antigens via specific receptors, such as Fc receptors or mannose receptors, or the APCs non-specifically phagocytose antigen. The capture through specific receptors is more efficient; antigens can be presented better when in complex with, for example, an antibody. Such a complex can be formed by injecting an antibody to a circulating antigen (e.g., PSA or CA 125), and the immune complexes can be targeted to dendritic cells and macrophages through the Fc-receptors present on these cells. However the high number of Fc receptors on neutrophils may considerably limit this process.

Immunotherapy is based on the principle of inducing or activating the immune system to recognize and eliminate undesirable cells, such as neoplastic cells. The key elements in any immunotherapy is to induce or trigger the host immune system to first recognize a molecule as an unwanted target, and then to induce the system to initiate a response against that molecule. In healthy hosts, the immune system recognizes surface features of a molecule that is not a normal constituent of the host (i.e., is "foreign" to the host). Once the recognition function occurs, the host must then direct a response against that particular foreign molecule.

Both the recognition and the response elements of the immune system involve a highly complex cascade of biological reactions. In most immunologically based disorders, at least one of the steps in the recognition phase, or at least one of the steps in the response phase, are disrupted. Virtually any disruption in either of these complex pathways leads to a reduced response or to the lack of any response. The inability of the immune system to destroy a growing tumor has been attributed, among other factors, to the presence of tumor-associated antigens (TAA) that induce immunological tolerance and/or immunosuppression. For example, in some kinds of cancer, the cancer itself tricks the host into accepting the foreign cancer cell as a normal constituent, thus disrupting the recognition phase of the immune system. The immunological approach to cancer therapy involves modification of the host-tumor relationship so that the immune system is induced or amplifies its response to the TAAs. If successful, inducing or amplifying the immune system can lead to tumor regression, tumor rejection, and occasionally, to tumor cure.

Antigenicity and Immunogenicity

As used herein, if a binding agent can recognize an antigen, i.e., can bind to or interact with an antigen, then the antigen is said to be antigenic. If the immune system can also mount an active response against the antigen, a complex containing the antigen, a portion of the complex, or the binding agent itself, it is said to be immunogenic.

The conventional definition of an antigen is a substance (such as an antibody or an antigen) that can elicit in a vertebrate host the formation of a specific antibody or the generation of a specific population of lymphocytes reactive with the substance. As frequently occurs in science, however, it is now known that this definition, although accurate, is not complete. For example, it is now known that some disease conditions suppress or inactivate the host immune response, and the substance that would have been expected to elicit an antibody or generate specific lymphocytes, does not. Thus, not all antigens are capable of eliciting a human immune response.

Typically, the antibody's capability of binding the antigen is based on highly complementary structures. That is, the shape of the antibody must contain structures that are the compliment of the structures on the antigen. The portion of the antigen to which an antibody binds is called the "antigenic determinant", or "epitope". Thus antigens are molecules that bear one or more epitopes which may be recognized by specific receptors in an immune system, a property called antigenicity.

Immunogenicity refers to the property of stimulating the immune system to generate a specific response. Thus, all immunogens are antigens, but not vice-versa. Although an immune system may recognize an antigen (e.g., binds to a T or B cell receptor), it does not respond to the antigen unless the antigen or an antigen-containing complex is also immunogenic.

An immune response to a particular antigen is greatly influenced by the structure and activity of the antigen itself, as well as myriad other factors. In some cases, the immune system is not able to generate an immune response to a particular antigen, a condition that is called tolerance.

In influencing whether an antigen is immunogenic or immunotolerant, an important characteristic of the antigen is the degree of difference between the antigen and similar molecules within the host The most immunogenic antigens are those that have no homologs in the host, i.e., those that are most "foreign." Other factors that promote immunogenicity include higher molecular weight, greater molecular complexity, the proper antigen dose range, the route of administration, the age of the host, and the genetic composition of the host (including exposure to antigens during fetal development).

As noted above, antigens may have one or more epitopes or binding sites that are recognized by specific receptors of the immune system. Epitopes may be formed by the primary structure of a molecule (called a sequential epitope), or may be formed by portions of the molecule separate from the primary structure that juxtapose in the secondary or tertiary structure of the molecule (called a conformational epitope). Some epitopes, e.g., cryptic epitopes, are hidden in the three dimensional structure of the native antigen, and become immunogenic only after a conformational change in the antigen provides access to the epitope by the specific receptors of the immune system. Some antigens, e.g., tumor-associated antigens such as ovarian cancer or breast cancer antigens, have multiple antibody binding sites. These antigens are termed "multi-epitopic" antigens.

An important feature and function of a comprehensive therapeutic reagent is the ability to initiate recognition and response to an antigen, to induce a cellular and humoral response (either or both) to the antigen, and to increase the immunogenicity of a molecule without affecting its antigenicity.

Antibodies bear three major categories of antigen-specific determinants—isotypic, allotypic, and idiotypic—each of which is defined by its location on the antibody molecule. For the purpose of the present invention, we shall only focus on the idiotypic category.

Idiotypic determinants, or idiotopes, are markers for the V region of an antibody, a relatively large region that may include several idiotopes each capable of interacting with a different antibody. The set of idiotopes expressed on a single antibody V region constitutes the antibody idiotype. An antibody (Ab1) whose antigen combining site (paratope) interacts with an antigenic determinant on another antibody V region (idiotope) is called an anti-idiotypic antibody (Ab2). Thus, an Ab2 antibody includes an antigen binding site which is also an antibody binding site. A portion of such anti-idiotypic antibodies (i.e., Ab2β) will identify an epitope within the paratope of the idiotype antibody, thus presenting an "internal" image of the epitope identified by the idiotype antibody on the tumor associated antigen. The phenomenon of producing an anti-idiotypic antibody having the internal image of the antigen may permit the use of antibodies to replace the antigen as an immunogen. For a graphic representation of these types of antibodies and their interaction, see FIG. 1.

For tumors that have antigens, there are at least four theories why the immune response may fail to destroy a tumor: 1) there are no B cells or cytotoxic T lymphocytes (CTL) capable of recognizing the tumor; 2) there are no TH cells capable of recognizing the tumor; 3) TS cells become activated before TH cells, thus preventing B-cell and CTL activation; and 4) the genes regulating tumor proliferation may be present from birth, so the host does not treat the gene products as "foreign."

"Passive immunotherapy" involves the administration of antibodies to a patient. Antibody therapy is conventionally characterized as passive since the patient is not the source of the antibodies. However, the term passive is misleading because the patient can produce anti-idiotypic secondary antibodies which in turn can provoke an immune response which is cross-reactive with the original antigen. "Active immunotherapy" is the administration of an antigen, in the form of a vaccine, to a patient, so as to elicit a protective immune response. Genetically modified tumor cell vaccines transfected with genes expressing cytokines and co-stimulatory molecules have also been used to alleviate the inadequacy of the tumor specific immune response.

If a specific antibody from one animal is injected as an immunogen into a suitable second animal, the injected antibody will elicit an immune response (e.g., produce antibodies against the injected antibodies—"anti-antibodies"). Some of these anti-antibodies will be specific for the unique epitopes (idiotopes) of the variable domain of the injected antibodies (anti-idiotypic antibodies). Others will be specific for the epitopes of the constant domains of the injected antibodies and hence are known as anti-isotypic antibodies.

The various interactions based on idiotypic determinants, called the idiotypic network, is based on the immunogenicity of the variable regions of immunoglobulin molecules (Ab1) which stimulate the immune system to generate anti-idiotypic antibodies (Ab2), some of which mimic antigenic epitopes ("internal image") of the original antigen. The presence of internal image antibodies (Ab2β) in the circulation can in turn induce the production of anti-anti-idiotypic antibodies (Ab3), some of which include structures that react with the original antigen.

The "network" theory states that antibodies produced initially during an immune response will carry unique new epitopes to which the organism is not tolerant, and therefore will elicit production of secondary antibodies (Ab2) directed against the idiotypes of the primary antibodies (Ab1). These secondary antibodies likewise will have an idiotype which will induce production of tertiary antibodies (Ab3) and so forth.

Ab1→Ab2→Ab3

In other words, one form of an anti-idiotypic antibody may be a surrogate antigen.

Two therapeutic applications arose from the network theory: 1) administer Ab1 which acts as an antigen inducing Ab2 production by the host; and 2) administer Ab2 which functionally imitates the tumor antigen.

The development of the "network" theory led investigators to suggest the direct administration of exogenously produced anti-idiotype antibodies, that is, antibodies raised against the idiotype of an anti-tumor antibody. Such an approach is disclosed in U.S. Pat. No. 5,053,224 (Koprowski, et al.) Koprowski assumes that the patient's body will produce anti-antibodies that will not only recognize these anti-idiotype antibodies, but also the original tumor epitope.

Conventional anti-idiotype antibodies are made by intraspecies or interspecies immunization with a purified antigen-specific pool of antibodies or a monoclonal antibody. The resulting antiserum is then extensively absorbed against similar molecules with the same constant region to remove antibodies with anti-$C_H C_L$ specificities. See, for example, Briles, et al.; "Idiotypic Antibodies," *Immunochemical Techniques* (New York, Academic; Colowich and Kaplan, eds; 1985). The production of anti-ID antibodies against self-idiotopes was one of the first key predictions of the network theory [Rodkey, S., *J. Exp. Med* 130:712-719 (1974)].

A human anti-idiotypic monoclonal antibody (Ab2) has been shown to induce anti-tumor cellular responses in animals and appears to prolong survival in patients with metastatic colorectal cancer. See Durrant, L. G. et al., "Enhanced Cell-Mediated Tumor Killing in Patients Immunized with Human Monoclonal Anti-Idiotypic Antibody 105AD7, " *Cancer Research,* 54:4837-4840 (1994). The use of anti-idiotypic antibodies (Ab2) for immunotherapy of cancer is also reviewed by Bhattacharya-Chatterje, et al; *Cancer Immunol. Immunother.* 38:75-82 (1994).

Idiotopes on lymphoid receptors may in some cases mimic external antigens because of the extensive diversity of the immune system. This idea prompted many attempts to use the internal image of a foreign antigen, mimicked by the idiotypes of T or B receptors, to act as targets for anti-idiotypic antibodies. In this way, it has been proposed that anti-idiotypic antibodies may induce populations of T or B cells that can bind the extrinsic (or soluble) antigen. Such anti-idiotypic antibodies can be used as vaccines, many of which are summarized in Greenspan, NS, and Bona, Calif.; *The FASEB Journal,* 7:437-444 (1992).

The ability to up- or down-regulate immune responses and to control potentially auto-reactive immunocompetent cells is vital for normal immune function and survival. Regulatory mechanisms include the induction of clonal anergy (via inappropriate antigen-presenting cells), peripheral clonal deletion/apoptosis, cytokine (e.g. transforming growth factor-beta (TGF-β) or IL-10)-induced non-responsiveness, 'veto' cells, auto-reactive cytolytic T cells, and both non-specific and antigen-specific T suppressor cells. At least in theory, each of these regulatory systems provides a mechanistic basis for 'therapeutic intervention'.

In addition to cancer immunotherapy, control of abnormal acute and chronic inflammatory response is also one of the most important challenges in medicine. Typical examples of acute and chronic inflammation include atopy, urticaria, asthma, autoimmune hemolytic anemia, rheumatoid arthritis, systemic lupus erythematosus, granulomatous diseases, tuberculosis, and leprosy.

Like the tumor immune response described above, the aim of the inflammatory response is the elimination of harmful agents. Further, the treatment of autoimmune inflammatory disease is sometimes complicated by autoimmune factors that prevent the host from eliminating the harmful agents, thereby leading to a persistent or chronic inflammatory response or condition.

Presently, it has been determined that essential events in the development of inflammation includes a cellular response involving neutrophils and macrophages, specifically the rolling, activation, and adhesion of neutrophils to endothelium via selectins-carbohydrate ligand interaction (and may include neutrophil extravasation).

Therapeutic compositions for the treatment of inflammation have included agents that bind to one or more of the mediators of inflammation. For example, antibodies specific for selectin carbohydrate ligands, and inhibiting selectin-carbohydrate ligand binding, may be important anti-inflammatory targets for the development of therapeutic compositions for the treatment of inflammation.

In addition to the above, there are other cases where an anti-idiotypic mode of induction of a response may be useful. If a given epitope of a protein is discontinuous and results from three-dimensional folding, an anti-Id can be produced that would mimic that structure. Further, in immunizing against latent and/or immunosuppressive viruses, there is the possibility of well known deleterious effects not solvable by the use of attenuated viruses (e.g., mumps, measles, rubella, and HIV). The use of anti-ID induction of protective immunity may avoid these deleterious effects.

SUMMARY OF THE INVENTION

The present invention is a method and composition for generating both a humoral and/or a cellular immune response by administering a binding agent that specifically binds to a pre-selected soluble antigen. In accordance with the invention, the binding agent-soluble antigen complex alters the immunogenic condition of the host by generating new immunogens that are recognizable by the immune system. This leads to a humoral and/or a cellular response. In one embodiment of the invention, the immune response comprises an anti-tumor response and/or cell killing.

The present invention is a comprehensive method for the treatment of certain diseases and conditions that includes, but is not limited to, targeting a pre-determined antigen, preferably a multi-epitopic antigen and/or preferably soluble; administering a binding agent, preferably a monoclonal antibody, and inducing a comprehensive immune response against the disease or condition that generated the target antigen. In a preferred embodiment of the invention, the binding agent or the binding agent/antigen complex induces the production of a humoral response, as evidenced in part by the production of anti-antigen (e.g., anti-tumor or anti-inflammation) antibodies, Ab3 and/or Ab1c; and/or induces the production of a cellular response, as evidenced in part by the production of T-cells that are specific for the binding agent, the binding agent/antigen complex, and/or the antigen.

The present invention also includes methods and compositions for altering the immunogenic state of the host organism. In altering the immunogenic state, the compositions and methods of the present invention increase, decrease, or maintain the host's immunogenic state. An example of deriving a therapeutic benefit by increasing the immunogenicity includes but is not limited to treatments for cancer or some infectious diseases. An example of decreasing the immunogenicity includes but is not limited to treatments for rheumatoid arthritis. An example of maintaining immunogenicity includes but is not limited to supplemental treatments for patients that have become tolerant to antigens after an initial response. In a most preferred embodiment of the invention, the methods and compositions do not decrease the antigenicity of the active component in the therapeutic composition.

The present invention also includes methods and compositions for increasing the over-all host response to a disease or condition. These methods and compositions produce a therapeutic benefit for the recipient.

The present invention also is a therapeutic composition comprising an active agent, or binding agent, that specifically binds to a pre-determined soluble antigen, wherein the binding agent, upon binding to the antigen, forms a complex that is both antigenic and immunogenic.

The compositions and methods of the present invention may also include one or more steps or substances that increase the over-all immunogenicity.

The therapeutic compositions and methods of the present invention are suitable for the treatment of any disease or cancer that produces a soluble antigen, preferably a multi-epitopic antigen.

The present invention also includes a method for designing new therapeutic agents comprising selecting a soluble antigen, preferably an antigen that has been determined to be multi-epitopic; and selecting a binding agent that specifically binds to said antigen to form a complex. In accordance with the invention, the binding agent, the binding agent/antigen complex, and/or the antigen lead to the production of a humoral and/or cellular response in vivo. In a preferred embodiment of the invention, the method for designing a new therapeutic agent results in a binding agent or the binding agent/antigen complex that induces the production of a humoral response, as evidenced in part by the production of anti-tumor or anti-inflammation antibodies, Ab3 and/or Ab1c; and/or induces the production of a cellular response, as evidenced in part by the production of T-cells that are specific for the binding agent, the binding agent/antigen complex, and/or the antigen.

Although several investigators have shown that antigen-specific antibodies can enhance the immune response to those antigens presented in a complex form, the present invention is the first to demonstrate that the injection of an antibody against a single epitope can induce a multi-epitopic immune response in cancer patients, provided that the patients' sera contained the respective antigen. The present invention also demonstrates that this antibody injection can change the patient's immune response in such a way that the self-protein CA125 can now be recognized by the immune system.

Stimulation of T cells reactive with subdominant or cryptic epitopes of self-proteins has been suggested as an important factor in inducing immunity to a pre-determined antigen, e.g., an antigen involved in a disease or condition such as cancer or auto-immunity. Antibody-enhanced or -altered presentation of an antigen, such as CA125, in an antibody complex, e.g., bound to MAb-B43.13, by B cells (antibody-specific), or macrophages or dendritic cells (both $F_c$ receptor mediated), may result in presentation of different peptides to the immune system than those obtained by presentation of the antigen alone. This can lead to sufficient presence of antigen-specific peptides from subdominant or cryptic epitopes which may in turn stimulate low-affinity T cells that escaped clonal deletion in the thymus or re-stimulate T cells which were suppressed. The immune response induced by exogenous administration of an antibody to a circulating self-antigen can therefore be compared to that observed in auto-immune diseases. This may also explain why presence of immune complexes of antigen with autologous human antibodies is often not correlated with improved survival. Human B cells recognize preferably immune-dominant epitopes of the antigen, leading to presentation of epitopes against which T cells were formed during fetal development. Murine antibodies on the other hand, recognize immune-dominant epitopes in mice which are not necessarily equivalent to the human immune-dominant epitopes.

The capture and processing of an antigen, e.g., PSA, by B-cells may also occur through the interaction of the membrane bound Ab2 with the anti-antigen/antigen (e.g., anti- PSA/PSA) complexes and in a similar manner through the interaction of membrane bound Ab3 with the antigen (complexed or not with the anti-PSA antibody). Although applicants do not wish to be bound by any particular theory of operability, it is believed that the observed immunological response achieved by the present invention is attributable to an interaction between a newly formed antigen and the human patient's immune system. As noted above, a portion of the immune response includes inducing the production of anti-(anti-idiotype) antibodies by the patient. Within this set of anti-(anti-idiotype) antibodies are those that are directly complimentary to the paratope of an anti-idiotype antibody. It is further believed that the paratope of the anti-idiotype antibody presents an "internal" image of the tumor cell epitope identified (i.e., selectively bound) by the idiotype antibody and, therefore, the anti-(anti-idiotype) antibodies will also bind the tumor antigen. In effect, the present method induces a immunological response to the first antigen, e.g., a tumor antigen, by presenting a second antigen (the paratope of the anti-idiotype antibody, which shares homologies with the tumor antigen) to a portion of the patient's resulting antibodies.

The present invention concerns altering immunogenicity in a manner that produces a beneficial or therapeutically desirable effect. As used herein and as described in more detail below, a beneficial or desirable immune response is one that produces a therapeutically desirable result. A beneficial therapeutic response will typically include activation of the immune system and/or one or more of its components, induction of the immune system and/or one or more of its components, and/or a T cell immune response, and/or a humoral immune response, and/or reduction in tumor burden, and/or an increase in survival time, and/or the like. For example, for a cancer such as ovarian cancer, a beneficial or desirable immune response includes the production of an antibody that immunoreacts with a previously non-immunoreactive ovarian cancer antigen. In this example, the immune response to an antigen is increased. In another example, for a condition such as inflammation, a beneficial or desirable immune response includes the production of an antibody that immunoreacts with a previously immunoreactive antigen so that it becomes non-immunoreactive. In this example, the immune response is decreased. In transplantation, the immune system attacks MHC-disparate donor tissue leading to graft rejection, in autoimmune disease it attacks normal tissues, and in allergy the immune system is hyper-responsive to otherwise harmless environmental antigens. It is now recognized that immunosuppressive therapy may be appropriate for treating each of these disorders.

DISCLOSURE OF THE INVENTION

Figure 1:
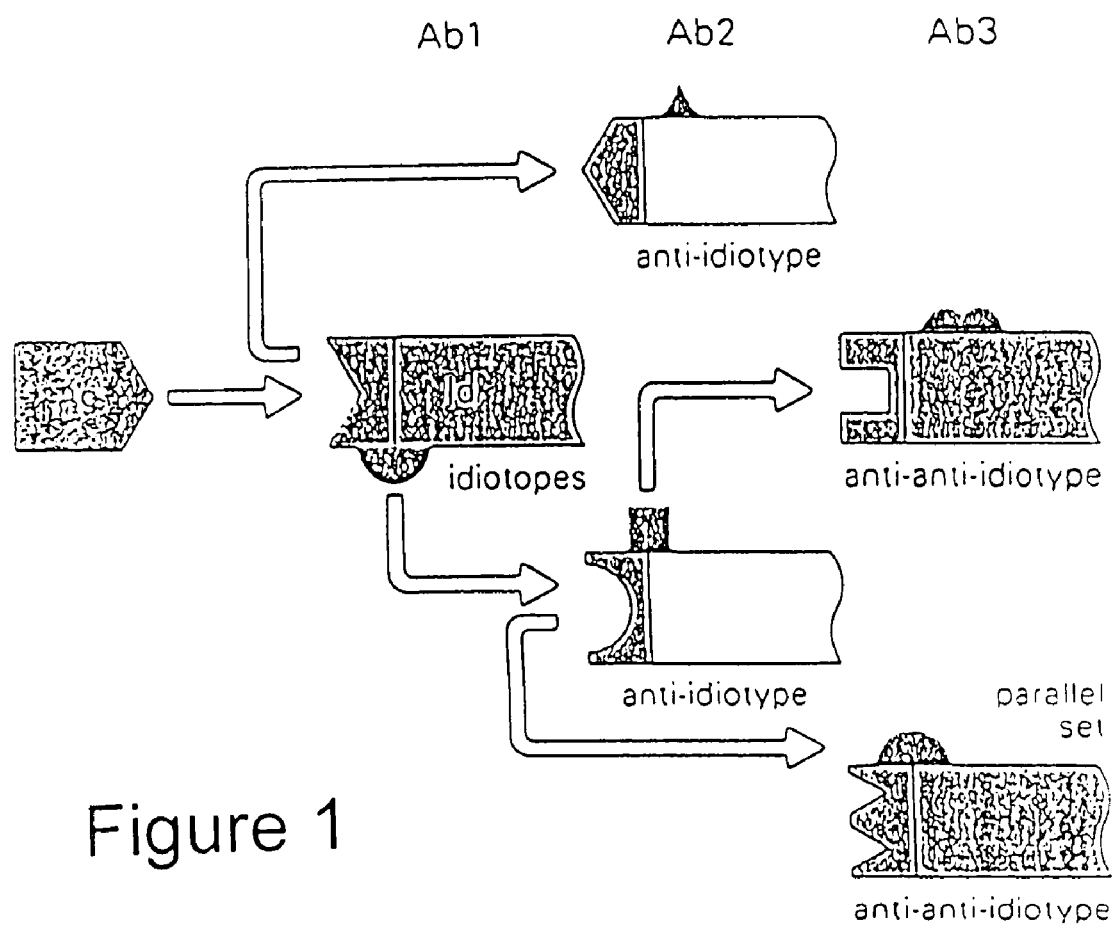
FIG. 1 is a graphic representation of the different types of antibodies and their structural relationship to each other and to an antigen.

The present invention comprises a method and composition for altering immunogenicity resulting in the induction or mediation of a comprehensive immune response.

The present invention comprises a method for increasing the immunogenicity of an administered composition by target selection, by activation methodologies, and by delivery systems that, in combination, induces either cellular or humoral immunity, or both.

The present invention involves the discovery that binding a binding agent to an antigen, such as a multi-epitopic tumor-associated antigen, increases the immunogenicity of the immunogen while maintaining its antigenicity, and leads to the generation of a humoral and/or cellular response to the immunogen. The methods and compositions of the present invention typically mediate a host's ability to generate an immune response to a previously non-immunogenic antigen, i.e., an antigen that does not stimulate the immune system to generate an effective host immune response. In this manner, the host immune system can recognize and initiate a beneficial, and preferably effective immune response to the previously unrecognized antigen.

In certain embodiments of the invention, the binding agent is a non-labeled binding agent, more preferably, a monoclonal antibody, and most preferably, a photoactivated monoclonal antibody. The antigen, defined in more detail below, is any immunotolerant antigen, preferably a tumor associated antigen. In preferred embodiments, the photoactivated antibody is an intact antibody having broken sulphur to sulphur bonds between the heavy and light chains of the antibody.

A composition and method of the present invention includes administering a binding agent that specifically binds to a pre-determined antigen to form a complex, wherein the complex is immunogenic. In preferred embodiments of the invention, the immunogenicity is evident in the production and/or induction of anti-idiotype antibodies (Ab2), anti-anti-antibodies (Ab3), antibodies to the complex, antibodies to the antigen (Ab1c, which is used interchangeably with Ab3'), cytotoxic lymphocytes, such as killer T cells or natural killer (NK) cells, and/or T cell proliferation.

A composition and method of the present invention includes administering an effective amount of a binding agent that specifically binds to a pre-determined antigen, wherein the antigen is preferably present in vivo in a high amount, allowing the binding agent to bind to the antigen, and inducing the production of a beneficial immune response against the antigen.

The present invention also includes compositions and methods that result in the induction of a beneficial immune response, particularly where one skilled in the art would not expect to find an antigen-specific immune response, e.g., tumor-associated antigens ("self") antigens.

An additional composition of the present invention may also include a modified antigen, wherein a soluble, preferably multi-epitopic, antigen is modified by binding to a binding agent. An additional method of the present invention may include producing the modified antigen, and/or using the modified antigen to achieve a therapeutic effect, e.g., producing, inducing, or inhibiting an immune response against the antigen.

In one embodiment of the invention, the methods and compositions include all binding agents as defined herein, exclusive of B43.13 antibodies. For example, a method and composition of the invention may include a composition comprising a binding agent that is free of, or substantially free of, B43.13 antibodies.

The invention further includes methods and compositions for treating ovarian cancer comprising a binding agent that specifically binds to an ovarian cancer antigen, such as CA 125, wherein said binding agent is exclusive of B43.13 antibodies, wherein the complex between the binding agent and the antigen is immunogenic.

In certain embodiments the invention provides a method for inducing a host immune response against a multi-epitopic in vivo antigen, such as a tumor associated antigen or a non-tumor associated antigen, present in the host's serum, which antigen preferably does not elicit an effective host immune response, the method comprising contacting the antigen with a composition comprising a binding agent that specifically binds to a first epitope on the antigen and allowing the binding agent to form a binding agent/antigen pair wherein a host immune response is elicited against a second epitope on the antigen. The present invention involves contacting an antigen, preferably a soluble antigen, with a composition of the invention, and reacting a binding agent in the composition with the antigen. In accordance with the invention, binding the antigen with the binding agent generates host recognition of the antigen. In turn, generating host recognition leads to initiating an immune response against the antigen.

In certain embodiments the invention provides a method for inducing an immune response against an antigen that does not elicit an effective host immune response, the method comprising administering to the host a low dose or a small amount of a binding agent that binds an epitope of a soluble form of the antigen. In certain embodiments the invention provides for a method for inducing an immune response against an antigen that does not elicit an effective host immune response, the method comprising administering to the host a binding agent that binds an epitope of a soluble form of the antigen using a low dose of binding agent, preferably a dose that does not produce ADCC and/or induce antibody-mediated toxicity. In some embodiments of the invention, low dose of binding agent comprises from about 0.1 μg to about 2 mg per kg of body weight of the host. In some embodiments of the invention, the antigen is a cellular antigen. ADCC is assessed by incubating $^{51}$Cr-labeled tumor cells with a binding agent according to the invention and adding fresh human PBMCs, followed by incubation for fourt hours and measurement of specific lysis. ADCC is deemed to be absent if specific lysis is less than 15%. As used herein, antibody-mediated toxicity refers to clinical toxicity, specific indicators of which include, but are not limited to, abnormal serum chemistries, impaired renal function, and signs and symptoms of serum sickness or anaphylaxis.

In certain embodiments, the invention provides a method comprising intravenously administering to the host a binding agent that binds an epitope of a soluble form of a cellular antigen.

In certain embodiments the host immune response comprises a cellular and humoral immune response. In certain embodiments, the host immune response comprises a cellular response. In certain embodiments, the host immune response comprises a humoral response. In certain embodiments, the antigen is a soluble antigen. In certain embodiments the binding agent is an antibody. In certain embodiments, the antibody is a murine monoclonal antibody. In certain embodiments the antibody does not induce antibody-mediated toxicity, e.g., isotypic induced HAMA toxicity, in the host. In certain embodiments the antigen is associated with a human disease or pathological condition. In certain embodiments the disease or pathological condition is cancer. In certain embodiments the binding agent is photoactivated. In certain embodiments the humoral response comprises anti-idiotype antibodies. In certain embodiments, the amount of binding agent is at least 0.1 μg and preferably up to 2 mg, more preferably between 1 μg and 200 μg per kg of body weight of the host.

In certain embodiments, the invention provides a therapeutic composition comprising a binding agent specific for a first epitope on a multi-epitopic antigen, which may be a tumor associated antigen or a non-tumor associated antigen, present in the host's serum, which antigen preferably does not elicit an effective host immune response, wherein the binding agent specifically binds to a first epitope on the antigen and forms a binding agent/antigen pair wherein a host immune response is elicited against a second epitope on the antigen. In preferred embodiments of the invention, the binding agent is an antibody, preferably an activated antibody, and most preferably, a photoactivated antibody.

In certain embodiments the invention provides a therapeutic composition comprising a low dose of a binding agent that binds an antigen, preferably a soluble or cellular antigen, which does not elicit an effective host immune response, wherein the binding agent specifically binds to the antigen and induces an immune response against the antigen. Preferably, the low dose of a binding agent is from about 0.1 μg to about 2 mg per kg of body weight of the host.

In certain embodiments the invention provides a therapeutic composition for intravenous administration comprising a binding agent that binds a soluble form of a cellular antigen which does not elicit an effective host immune response, wherein the binding agent specifically binds to the antigen and induces an immune response against the antigen. In a preferred embodiment of the invention, compositions administered intravenously preferably do not include adjuvant. In certain embodiments the invention provides a therapeutic composition for subcutaneous administration comprising a binding agent that binds an epitope of a soluble form of a cellular antigen which does not elicit a host immune response, wherein the binding agent specifically binds to the epitope and induces an immune response against the cell surface form of the antigen. As used herein, a "soluble form of a cellular antigen" refers to a circulating form of an antigen that is also expressed on a cell surface. In a in preferred embodiment of the invention, compositions administered subcutaneously preferably include adjuvant.

Those skilled in the art will recognize that these embodiments may be used alone, or in any combination.

In accordance with the present invention, the inventors believe the interaction between the antigen and the binding agent may effectively present a previously unexposed or suppressed epitope to the patient's immune system to generate: 1) a humoral response resulting in human anti-tumor antibodies that may or may not be inhibitable by the injected antibody, but are definitely inhibitable by an antibody that binds to an epitope different from the epitope reactive with the injected binding agent; and 2) a cell-mediated response resulting in the production of antigen-specific T-cells.

One skilled in the art will recognize that an aspect of any antibody-based immunotherapy is the interaction between the antigen and the antibody. Also, the success, effectiveness, and usefulness of that binding event typically involves a wide variety of sometimes interwoven factors. In general, these factors include but are not limited to the binding capacity of the binding agent, immunogenicity of the binding agent, accessibility of the antigen, accessibility of the antigen's epitope, the degree of complementarity between the paratope of the binding agent and the epitope of the antigen, the effect of the binding event on the complex, the complex's capability of inducing an immune response, and the extent to which the immune response is activated. It is intended that these factors contribute to the determination of an appropriate or desirable binding agent and/or pre-determined antigen, and to the nature and effectiveness of the resulting immune response.

The interplay of these various considerations, as taught by the present invention, may lead one to effective therapeutic remedies. In the case of B43.13 and the treatment of ovarian cancer, a specific example used to prove the general point without thereby limiting the invention, B43.13 is a murine antibody, so its heterogeneity in a human system contributes to its immunogenicity. Further, CA 125, the target antigen, is a soluble, tumor associated antigen, and thereby accessible to a binding agent. The binding event between B43.13 and CA 125 is of such a nature that one or more epitopes on the complex become available to components of the immune system, thus inducing an immune response where previously there was none (or so little that no therapeutic benefit was derived). Further, the binding event created access to an epitope on the complex that was suitable for inducing both humoral and cellular immune responses, thus inducing a comprehensive immune response that is itself a beneficial immune response. As pertains B43.13, all of these individual elements contributed to the recognition of the use of B43.13 to induce an immune response cascade that is effective in the treatment of ovarian cancer.

As noted above, the inventors believe that an important aspect of inducing or mediating a cellular and humoral response lies in part in increasing the immunogenicity of the binding agent-antigen complex while maintaining its antigenicity. As described in more detail below and in the Examples, increasing immunogenicity while maintaining antigenicity may be affected by one or more of the following:

1. Administering a dose of binding agent that is low in comparison to the dose for other therapeutic compositions;
2. Forming a binding agent-antigen complex in vivo or ex vivo;
3. Photoactivating the binding agent prior to administration
4. Administering the binding agent in a microsphere, liposome, nanosphere, or micelle;
5. Conjugating the binding agent to a photodynamic agent, such as hypocrellin B; and
6. Conjugating the binding agent to immune effectors.

In a preferred embodiment of the invention, a composition comprising a pre-determined antibody that specifically binds to a pre-determined tumor associated antigen is used to bind a soluble antigen produced by the tumor. Once the soluble antigen is bound, the immune system recognizes the antigen as "foreign," and mounts an immune response against the antigen or against the binding agent bound to the antigen. Antigens that can be made immunogenic are potentially useful to induce or activate an immune response, leading to therapeutic and possibly prophylactic benefits.

Any composition that includes a binding agent according to the invention may be used to initiate an in vivo immune response. The composition may include one or more adjuvants, one or more carriers, one or more excipients, one or more stabilizers, one or more imaging reagents, one or more effectors; one or more photodynamic agents; and/or physiologically acceptable saline. Generally, adjuvants are substances mixed with an immunogen in order to elicit a more marked immune response. Control vaccinations without the adjuvant resulted in humoral immune responses. In a preferred embodiment of the invention, the composition comprising a binding agent does not include adjuvant.

In a preferred embodiment of the invention, a suitable composition includes a binding agent that binds to a soluble antigen to form a complex that is itself antigenic and immunogenic. In a most preferred embodiment of the invention, the complex is an antigen that induces a beneficial or desirable therapeutic effect.

The composition may also include pharmaceutically acceptable carriers. Pharmaceutically accepted carriers include but are not limited to saline, sterile water, phosphate buffered saline, and the like. Other buffering agents, dispersing agents, and inert non-toxic substances suitable for delivery to a patient may be included in the compositions of the present invention. The compositions may be solutions suitable for administration, and are typically sterile and free of undesirable particulate matter. The compositions may be sterilized by conventional sterilization techniques.

In accordance with the teachings of the present invention, the methods and compositions produce both a humoral and cellular response. Those skilled in the art will readily recognize that determining that a humoral and/or cellular response has been generated is easily shown by testing for the structures associated with each response. For example, evidence of the production of a humoral response includes but is not limited to the production of Ab2 and Ab3. Likewise, evidence of the production of a cellular response includes but is not limited to the production of T2 and/or T3 cells.

Binding Agents

The binding agents of the present invention bind an antigen of interest, and the resulting immunogenic pair or complex may be used to prime or initiate an immune response, typically to another epitope on the complex or a portion of the complex. The epitope, which previously did not elicit an effective immune response, upon being recognized by agents of the immune system, initiates the immune system cascade that results in a beneficial immune response, preferably an effective immune response as used herein, an effective host immune response means amelioration or elimination of the disease or condition that produces the antigen.

A binding agent (BA), as used herein, refers to one member of a binding pair, including an immunologic pair, e.g., a binding moiety that is capable of binding to an antigen, preferably a single epitope expressed on the antigen, such as a pre-determined tumor antigen. In some embodiments of the invention, the binding agent, when bound to the antigen, forms an immunogenic complex. Exemplary binding agents include, but are not limited to: monoclonal antibodies ("MAb"), preferably IgG1 antibodies; chimeric monoclonal antibodies ("C-MAb"); humanized antibodies; genetically engineered monoclonal antibodies ("G-MAb"); fragments of monoclonal antibodies (including but not limited to "F(Ab)$_2$", "F(Ab)" and "Dab"); single chains representing the reactive portion of monoclonal antibodies ("SC-MAb"); antigen-binding peptides; tumor-binding peptides; a protein, including receptor proteins; peptide; polypeptide; glycoprotein; lipoprotein, or the like, e.g., growth factors; lymphokines and cytokines; enzymes, immune modulators; hormones, for example, somatostatin; any of the above joined to a molecule that mediates an effector function; and mimics or fragments of any of the above. The binding agent may be labeled or unlabeled.

A binding agent according to the invention is preferably a monoclonal or polyclonal antibody. The antibody includes, but is not limited to native or naked antibodies; and modified antibodies, such as activated antibodies, e.g., chemically activated or photoactivated antibodies. As used herein, native refers to a natural or normal antibody; naked refers to removing a non-native moiety, e.g., removing the label from a labeled antibody. In a most preferred embodiment of the invention, the binding agent is an Ab1 antibody that induces the production of one or more molecules that comprise an immune response, including but not limited to one or more of the following: molecules associated with a cellular response (cytokines, chemokines, cytotoxic T lymphocytes (CTL), and natural killer cells (NK)), and/or molecules associated with a humoral response [Ab3, Ab1c (sometimes referred to as Ab3')].

Those skilled in the art are enabled to make a variety of antibody derivatives. For example, Jones et al., Nature 321: 522-525 (1986) discloses replacing the CDRs of human antibody with those from a mouse antibody. Marx, Science 229: 455-456 (1985) discusses chimeric antibodies having mouse variable regions and human constant regions. Rodwell, Nature 342: 99-100 (1989) discusses lower molecular weight recognition elements derived from antibody CDR information. Clackson, Br. J. Rheumatol. 3052: 36-39 (1991) discusses genetically engineered monoclonal antibodies, including Fv fragment derivatives, single chain antibodies, fusion proteins chimeric antibodies and humanized rodent antibodies. Reichman et al., Nature 332: 323-327 (1988) discloses a human antibody on which rat hypervariable regions have been grafted. Verhoeyen, et al., Science 239: 1534-1536 (1988) teaches grafting of a mouse antigen binding site onto a human antibody. Biospecific antibodies are also known in the art.

Methods for producing and obtaining an antibody are well known by those skilled in the art. An exemplary method includes immunizing any animal capable of mounting a usable immune response to the antigen, such as a mouse, rat, goat sheep, rabbit or other suitable experimental animal. In the case of a monoclonal antibody, antibody producing cells of the immunized animal may be fused with "immortal" or "immortalized" human or animal cells to obtain a hybridoma which produces the antibody. If desired, the genes encoding one or more of the immunoglobulin chains may be cloned so that the antibody may be produced in different host cells, and if desired, the genes may be mutated so as to alter the sequence and hence the immunological characteristics of the antibody produced. Fragments of binding agents, may be obtained by conventional techniques, such as by proteolytic digestion of the binding agent using pepsin, papain, or the like; or by recombinant DNA techniques in which DNA encoding the desired fragment is cloned and expressed in a variety of hosts. Irradiating any of the foregoing entities, e.g., by ultraviolet light, will enhance the immune response to the antigen. In a preferred embodiment of the invention, effector functions that mediate CDC or ADCC are not required. Various binding agents, antibodies, antigens, and methods for preparing, isolating, and using the binding agents are described in U.S. Pat. No. 4,471,057 (Koprowski), U.S. Pat. No. 5,075,218 (Jette, et al.), U.S. Pat. No. 5,506,343 (Kufe), and U.S. Pat. No. 5,683,674 (Taylor-Papadimitriou, et al), all incorporated herein by reference. Furthermore, many of these antibodies are commercially available from Centocor, Abbott Laboratories, Commissariat a L'Energie Atomique, Hoffman-LaRoche, Inc., Sorin Biomedica, and FujiRebio.

The preferred binding agents of the present invention, murine monoclonal antibodies, may be produced according to conventional techniques well known to those skilled in the art. Hybridoma production in rodents, particularly in mice, is a very well established procedure and is preferred. Stable murine hybridomas provide an unlimited source of antibody of select or pre-determined characteristics. Typically, a monoclonal antibody can be prepared using any technique which provides for the production of antibody molecules by continuous cell lines in culture. These include but are not limited to the hybridoma technique originally described by Kohler and Milstein [Nature, 256:495-497 (1975)]; the human B-cell hybridoma technique [Kozbor, et al., Immunology Today, 4:72 (1983)]; and the EBV transformation technique [Cole, et al., Monoclonal Antibodies and Cancer Therapy, Alan R. Liss, Inc., pp. 77-96 (1985)].

Briefly, a monoclonal antibody of the invention may be produced by immunizing an animal, typically a mouse, with an immunogen, e.g., an antigen such as CA 125. The invention includes but is not limited to the use of a peptide segment that includes a specific epitope or pre-determined amino acid sequence. These peptides can be synthesized and optionally conjugated to a carrier protein, such as keyhole limpet hemocyanin (KLH), and used an immunogen.

The procedure is then followed by obtaining immunized lymphoid cells (e.g., splenetic lymphocytes) from the immunized animals, fusing the lymphoid cells with an immortalized cell (e.g., a myeloma or a heteromyeloma) to produce hybrid cells that can be propagated in culture indefinitely, and then screening the hybrid cells to identify those that produce monoclonal antibodies that react with the target epitope.

The resulting hybridoma can be selected by any of numerous assays, e.g., for binding to Ab2, or for inhibiting Ab1 binding to tumor cells. For example, the binding site epitope or peptide sequences containing the epitope can be synthesized and/or immobilized on polyethylene pins or another support. The appropriate monoclonal antibody can then be determined by its capacity to bind the immobilized peptide, as detected by ELISA using a labeled antibody (labeled with, e.g., peroxidase).

If desired, murine or other animal antibodies may be humanized following any of a number of procedures well known in the art. For example, Reichmann et al [Nature, 322:323-327 (1988)] used recombinant DNA methodology to replace the six hypervariable regions from the human antibody heavy and light chain variable domains with the hypervariable regions from the rodent antibodies. The reshaped human antibodies have the affinity of the original antibodies due to the presence of the original hypervariable regions, but would have all other characteristics of a human antibody.

One of the most promising approaches to tumor immunotherapy is to use antibody fragments or antibody fragments with effector domains to target and kill tumor cells. Single-chain Fv (scFv) has been genetically engineered as a recombinant fusion protein that is composed of a heavy chain (Vh) and a light-chain (V1) variable domain connected by an artificial linker and an effector domain.

In some preferred embodiments, the binding agents according to the invention are activated, preferably by chemical or photodynamic approaches. Preferred chemical approaches include organic reducing agents, such as formamidine sulfonic acid, inorganic reducing agents, nercurous ion, stannous ion, cyanide ion, sodium cyanoborohydride and sodium borohydride, thiol exchange reagents, such as dithiothreitol, mercaptoethanol and mercaptoethanolamine, and protein reducing agents, such as thioredoxin. Use of these reagents results in reduction of some disulfides within the binding agent to produce a binding agent having some sulfhydryl groups. The presence of such groups can change the tertiary structure of the binding agent. Such structural change can modulate the immunoreactivity of the binding agent. Such modulation may lead to an improved anti-idiotypic response and/or cellular response in an individual to whom the binding agent is administered.

In some preferred embodiments, the binding agents according to the invention may optionally be coupled to photodynamic agents. Preferably, such coupling is by covalent linkage or by liposomal association. Liposomal association is preferably achieved by mixing the photodynamic agent with a binding agent in the presence of a liposome-forming reagent. In certain preferred embodiments, the binding agent according to the invention is covalently linked to the liposome-forming reagent. Preferred photodynamic agents include hypocrellins, such as hypocrellin B, more preferably, aminated hypocrellins and hypocrellin derivatives.

In an embodiment of the invention, a suitable composition for the treatment of an ovarian tumor associated antigen contains a binding agent that binds the CA 125 antigen. Exemplary antibodies that bind to CA 125 include, but are not limited to B43.13. The mouse hybridoma B43.13 (MCB-ALT-96), which produces the antibody B43.13, was deposited with the American Type Culture Collection (ATCC), 10801 University Blvd., Manassas, Va. 20110-2209, on May 18, 2000, and was given ATCC deposit number PTA-1883. The present invention also includes the use of any binding agent other than B43.13 that specifically binds to CA 125 and that results in a beneficial immune response, B27.1, e.g., or M11. These and other exemplary antibodies are disclosed in Nustad, et al, Tumor Biology, 17:196-219 (1996) and Nap, et al, Tumor Biology, 17:325-331 (1996).

In another embodiment of the invention, a suitable composition for the treatment of gastrointestinal cancer contains a binding agent that binds the CA 19.9 antigen. Exemplary antibodies that bind to CA 19.9 include, but are not limited to Alt-3, W25 (CIS Bio International), A3 (Shemyakin Inst. Biorg. Chem.), and 1116-NS-19.9 (Centocor), among others. These and other exemplary antibodies are disclosed in Tumor Biology, 19:390-420 (1998). The mouse hybridoma AR44.6R1331, which produces the antibody Alt-3, was deposited with the American Type Culture Collection (ATCC), 10801 University Blvd., Manassas, Va. 20110-2209, on Nov. 17, 2000, and was given ATCC deposit number PTA-2691.

In yet another embodiment of the invention, a suitable composition for the treatment of breast cancer contains a binding agent that binds the CA 15.3 antigen. Exemplary antibodies that bind to CA 15.3 include, but are not limited to SM-3, DF-3, DF3-P, Ma 552, and BC4E549. These and other exemplary antibodies are disclosed in *Tumor Biology*, 19:21-29 (1998).

In yet another embodiment of the invention, a suitable composition for the treatment of prostate cancer contains a binding agent that binds the prostate specific antigen (PSA). An exemplary antibody that binds to PSA includes, but is not limited to AR47.47. The mouse hybridoma AR47.47, which produces the antibody AR47.47, was deposited with the American Type Culture Collection (ATCC), 10801 University Blvd., Manassas, Va. 20110-2209, on Apr. 29, 1998, and was given ATCC deposit number HB-12526.

In yet another embodiment of the invention, a suitable composition for the treatment of inflammation includes a binding agent that binds CA 19.9 antigen. Exemplary antibodies that bind to CA 19.9 and reduce inflammation include but are not limited to Alt-3 and Alt-4 antibodies. The mouse hybridoma AR18.4R3313, which produces the antibody Alt-4, was deposited with the American Type Culture Collection (ATCC), 10801 University Blvd., Manassas, Va. 20110-2209, on Nov. 17, 2000, and was given ATCC deposit number PTA-2692.

Soluble Antigen

A pre-determined antigen may be any human or mammalian antigen of clinical significance. In accordance with the present invention, the pre-determined or target antigen must be capable of binding a binding agent. Capable of binding includes, but is not limited to one or more of the following: the antigen may be soluble, circulating, present, detectable, and/or include a binding site accessible to an administered binding agent.

In a preferred embodiment of the invention, the antigen is a tumor-associated antigen (TAA). In the case of TAA, the cancer may include, but is not limited to lung, colon, rectum, breast, ovary, prostate gland, head, neck, bone, immune system, or any other anatomical location. Illustrative tumors and tumor markers are listed in U.S. Pat. No. 5,075,218.

The methods of the present invention may involve any cancer that produces a soluble multi-epitopic TAA. As used herein soluble is used to describe any antigen that is detectable in a body fluid, i.e., blood, serum, ascites, saliva, or the like. In accordance with the present invention, the preferred tumors are those that: shed soluble tumor antigens, e.g., tumor antigens shed into the bloodstream, as opposed to a surface antigen or an intracellular antigen; exhibit a multi-epitopic tumor associated antigen, and can be found at a concentration in the patient's body fluid more than is normally present in healthy controls and such a high level signifies presence of the disease, yet has not initiated a significant immune response. In a preferred embodiment, the predetermined antigen is an antigen that does not elicit an effective host immune response, e.g., is not effective in reducing tumor burden and/or does not induce a therapeutic benefit (even if a small immune response is generated). As is well known by one skilled in the art, one method of determining whether the concentration of the TAA is greater than in healthy individuals is by comparing the patient's concentration to that of a healthy control. If the concentration of the TAA is higher than the healthy control, then the patient's concentration is predictive of presence or recurrence of the disease.

The invention also involves the production of a modified antigen, typically by producing the modified antigen in vivo. As used herein, modified antigen refers to a first antigen, typically invisible to the immune system, that binds to a binding agent, and the binding agent-antigen is itself an antigen (the "second" antigen) that is immunoreactive with one or more molecules of the immune system.

As used herein, "disease" refers to the management, diagnosis, and/or palliation of any mammalian (including human) disease, disorder, malady, or condition. "Disease" includes but is not limited to cancer and its metastases, such as skin cancer; growths or tumors, and their metastases; tumors and tumor cells, such as sarcomas and carcinomas, including solid tumors, blood-borne tumors, and tumors found in nasal passages, the bladder, the esophagus, or lung, including the bronchi; viruses, including retroviruses and HIV; infectious diseases, such as hepatitis, including chronic hepatitis such as hepatitis B; bacterial diseases; fungal diseases; and dermatological conditions or disorders, such as lesions of the vulva, keloid, vitiligo, psoriasis, benign tumors, endometriosis, Barett's esophagus, *Tinea capitis*, and lichen amyloidosis; and autoimmune disorders, such as rheumatoid arthritis. Exemplary soluble multi-epitopic antigens are described above, and include but are not limited to CA 125, CA 19.9, CA 15.3, polymorphic epithelial mucin (PEM), CEA, and prostate specific antigen.

It should be noted that many of these diseases and/or disorders are characterized in part by including symptoms or biological processes involved with inflammation. Many types of immune-mediated inflammation, including chronic and acute inflammation, and many types of arthritis, including rheumatoid arthritis, and many types of cancer all express or involve the same or similar carbohydrate ligands. Exemplary ligands include, but are not limited to $SLe^a$ and $SLe^x$. An embodiment of the invention includes compositions that include in part one or more binding agents that bind to a carbohydrate ligand. These compositions are effective against any disease or condition that involves the carbohydrate ligand as part of its metabolic pathway, including, but not limited to rheumatoid arthritis, collagen-induced arthritis, adjuvant arthritis, and pristane-induced arthritis. For purposes of this aspect of the invention only, an "effective host immune response" means eliminating harmful factors, thereby eliminating a persistent or chronic inflammatory response or condition.

A high level of antigen, as used herein, is a variable term dependent in part on the type of the antigen, and/or the type of disease or condition, and/or the stage of the disease or condition. For example, one skilled in the art will recognize that a high level may mean that a majority of cancer-positive patients, e.g., above 50% or above about 80%, have a certain amount of circulating antigen. For example, the present understanding of the course of ovarian cancer suggests that 80% or higher of the patients having greater than 35 U/ml of CA 125 antigen in their bloodstream have a statistically significant higher risk of developing ovarian cancer. A high level also may be defined in terms of the amount sufficient to completely or substantially completely bind all of a pre-determined dose of binding agent. A high level may also be defined as a threshold quantity of circulating antigen that those skilled in the art recognize as a high level. A high level may also include that amount that is predictive of disease. A high level may also include an amount or concentration of antigen higher than what is normal for that patient or for that disease or condition.

A method of an embodiment of the invention includes determining the amount of pre-determined antigen in the patient, e.g., circulating in the patient, and if the amount of antigen is a high level, then administering a composition comprising a binding agent according to the invention. A more preferred method of the invention includes determining the amount of circulating pre-determined antigen in the patient and, if the amount is greater than an amount predictive of the disease, more preferably three times greater, then administering a composition comprising a binding agent according to the invention. For example, a method of the invention includes determining the amount of circulating CA 125, and if the amount is greater than about 35 U/ml, and more preferably greater than about 105 U/ml, then administering a composition comprising a binding agent according to the invention, e.g., comprising B43.13. The administered composition may include a low dose of binding agent.

As noted in the background section, the potential effect of injecting a binding agent such as an antibody can be extremely complex and may typically involve distinct mechanisms of action. As used in herein, Ab3 and Ab1c represent two such distinct mechanisms that individually and/or collectively produce a beneficial effect. In the Ab3 pathway, an Ab1 antibody that is capable of binding to a pre-determined antigen may induce the production of an anti-idiotype antibody (Ab2β) that mimics an epitope of the antigen. The anti-idiotype antibody in turn may induce the production of anti-anti-idiotype antibodies (Ab3) that are capable of binding the same epitope on the antigen as the Ab1 antibody. Evidence of this pathway includes a competitive assay between Ab1 and Ab3, since the Ab1 antibody and the Ab3 antibody compete for the same epitope of the antigen.

In the Ab1c pathway, the Ab1 antibody binds to the antigen to form a complex. This complex is itself an antigen, and is sometimes described herein as a "modified antigen" or second antigen. The complex may induce the production of anti-antigen antibody (Ab1c) that are capable of binding a different epitope on the antigen as that bound by the Ab1 antibody. Evidence of this pathway also includes a competitive assay, but comparing the inhibitory effect on Ab1c by antibodies that bind to different epitopes on the antigen or lack of inhibition with Ab1.

In addition to producing Ab3 and/or Ab1c, typically associated with a humoral immune response, the compositions of the present invention may also produce a therapeutic benefit by inducing a cellular immune response (cell mediated immunity), as in the Background section. Both the cellular and the humoral response involve indirect mechanisms for altering the immunogenicity of the host.

Compositions of the present invention may also initiate direct mechanisms for killing undesirable cells such as cancer cells. For example, in antibody-dependent cell-mediated cytotoxicity (ADCC), an Ab1 antibody, bound through its Fab region to a pre-determined antigen, may bind to the Fc receptor of a lymphocyte through the Fc region of the Ab1 antibody. Such participation between an antibody and immune system cells produces an effector function that may lyse tumor cells, infectious agents, and allogeneic cells. Other indirect mechanisms involve complement-mediated cytotoxicity (CDC), apoptosis, (neutralization of immunosuppressive tumor-associated antigens), induction of cytokines and/or chemokines, neutralization of immunosuppressive molecules, and neutralization of anti-adhesion molecules, among others.

As used herein, a comprehensive approach to providing a therapeutic benefit involves one or more, or all, of the following: cellular immunity and the molecules involved in its production; humoral immunity and the molecules involved in its production; ADCC immunity and the molecules involved in its production; CDC immunity and the molecules involved in its production; natural killer cells; and cytokines and chemokines, and the molecules and cells involved in their production. One skilled in the art will recognize that a beneficial immune response (and thereby overcoming immunotolerance) may be determined by a number of ways. Activation of the multiple arms of the immune systems may be determined, for example, by measuring the pre- and post-treatment antigen specific immune response, or by measuring the reduction or amelioration of tumor burden and/or tumor size, or by determining an increased survival period.

Specific demonstrations of the induction of a beneficial immune response or providing a therapeutic benefit would include one or more of the following:

1) a humoral response to the administered antibody (Ab1), including evidence of HAMA and/or Ab2;

2) a humoral response to the antigen, including evidence of the appearance of antigen-specific antibodies to the same and/or different epitopes on the antigen as the epitope for the binding agent (e.g., Ab3 and/or Ab1c);

3) antibody-dependent cytotoxicity, including evidence that post-injection sera with an antigen-specific antibody titer mediates tumor killing when the sera is incubated peripheral blood mononuclear cells and tumor cell targets relative to pre-injection baseline serum;

4) complement-dependent cytotoxicity, including evidence that post injection sera combined with complement-containing plasma kills tumor cell targets relative to pre-injection baseline serum;

5) natural killer cell activity, including enhanced tumor cell killing by peripheral blood mononuclear cells (containing NK cells) in post-injection blood samples taken prior to the appearance of a measurable antibody response to the TAA relative to pre-treatment peripheral blood mononuclear cells;

6) antigen-enhanced cytotoxicity, including enhanced tumor cell target killing by peripheral blood mononuclear cells (in the presence of TAA-positive tumor cells) relative to pre-administration levels; and 7) cellular immunity, including evidence of T cell proliferation or tumor cell lysis post-injection relative to pre-injection.

Further, evidence of a beneficial immune response may include demonstrating that the binding agent-antigen complex results in a more vigorous T cell proliferative response than the response to either the binding agent or the antigen alone (in post-treatment PBMC versus pre-treatment). One skilled in the art will also recognize that this battery of evidence demonstrates that the compositions and methods of the present invention induce multiple different immune system pathways, and that these various pathways have varying relative importance to a particular patient, depending on the individual's specific immune constitution.

Immunugenicity Enhancers

1. Low Dose

In accordance with the methods of the present invention, a composition comprising the binding agent may be administered in an amount sufficient to recognize and bind the antigen, such as a pre-determined tumor associated antigen (TAA), and more preferably a soluble multi-epitopic antigen. In a preferred embodiment of the invention, the dosage is sufficient to generate or elicit a beneficial, and preferably an effective immune response against the antigen. See Example 17. An immunologically or therapeutically effective or acceptable amount of binding agent is an amount sufficient to bind a pre-determined antigen in vivo or ex vivo, and is capable of eliciting an effective immune response to the antigen. The response may inhibit or kill cells, e.g., tumor cells, that carry and present a newly accessible epitope, thereby ameliorating or eliminating the disease or condition that produces the antigen. The immune response may take the form of a humoral response, a cell-mediated response, or both. In a preferred embodiment of the invention, the dosage of the monoclonal antibody is less than the dosage required to produce ADCC or CDC to the administered binding agent.

The concentration or dosage of the protein in the composition can vary widely, e.g., from less than about 0.01% to about 15 to 20% by weight. As noted above, the composition is administered in an amount sufficient to stimulate an immune response against the antigen. Amounts effective for this use will depend in part on the severity of the disease and the status of the patient's immune system. Generally, the composition will include about 0.1 µg to about 2 mg or more of protein agent per kilogram of body weight, more commonly dosages of about 1 µg to about 200 µg per kilogram of body weight, recognized by those skilled in the art as comprising a low dose. Further, those skilled in the art will recognize and be able to evaluate the various considerations that may be used to determine a proper dose. The concentration will usually be at least 0.5%; any amount may be selected primarily based on fluid volume, viscosity, antigenicity, etc., in accordance with the particular mode of administration.

A method and composition of an embodiment of the invention includes a composition comprising a low dose of a binding agent, wherein low dose refers to an amount less than about 2 mg/kg of body weight, even more preferably, between about 0.1 µg to about 2 mg per kilogram of body weight, and wherein the administration of the composition comprising a low dose of binding agent induces a beneficial immune response.

2. Photoactivation

In accordance with the present invention, an antibody may be photoactivated.

In some embodiments, the present invention is directed to preparing antibodies using UV light so that the immunogenicity of the whole antibody is increased. As used herein, increasing the immunogenicity refers to increasing the recognition and/or response of an anti-idiotypic and/or anti-isotypic antibody. In a most preferred embodiment of the invention, the method increases the immunogenicity of the immunogen without altering or adversely affecting its antigenicity.

In accordance with the present invention, it may be beneficial to generate an enhanced response in order to produce a therapeutic benefit. For example, in accordance with the present invention, it may be desirable to administer UV-exposed antibodies to a cancer patient, with the specific purpose of generating an immune response (i.e., producing anti-idiotypic antibodies) to the UV-exposed antibody. This response may provide a therapeutic advantage via the humoral and cellular consequences directed to the cancer cells. In accordance with one aspect of the invention, the UV-exposed protein exhibits increased immunogenicity and therefore may be useful as a therapeutic for a disease.

The protein alteration processes of the present invention result in a modified protein with enhanced immunogenic potential. Perhaps the hydrophobicity/hydrophilicity has been altered by minor tryptophan disruption in combination with sulffiydryl generation to enhance its recognition/response by the immune cells. It is further possible that the antibody's constant portion has key amino acid specific changes which enhance Fc-mediated antigen presenting cell recognition. This is not related to changes in the polymeric state of the protein whereby aggregated forms (as have been observed for human immunoglobulins after UV exposure) are directed to phagocytic cells, since the photoactivated product maintains its monomeric state. The final extent of presentation and response of the antibody/antigen complex typically improve as a result of photoactivation, as detected by the HAMA response of antigen-positive patients injected with the photoactivated antibody.

Processes for photoactivating a binding agent are extremely well known in the art, and include exposing the antibody to radiation, wherein the resulting altered antibody is capable of generating an immune response when administered to an animal typically capable of generating an immune response to the native form of the antibody.

In a preferred embodiment of the invention, the antibody is exposed to ultraviolet light. Typically, the antibody may be exposed to ultraviolet light at a wavelength from about 200 nm to about 400 nm, at from about 0.1 to about 1000 Joules/$cm^2$, for from about 1 to about 180 minutes (more preferably, about 10 to about 30 minutes). Tests run under these conditions show that the process typically results in an intact or whole antibody that has been activated. These tests suggest that the process according to the invention generates sulffiydryls between the light and heavy chains of the antibody.

3. Delivery System

Since some binding agents such as proteins are by themselves poor immunogens, their immunogenicity may be augmented by administration in immunological adjuvants and antigen delivery systems. The immunogenicity of a specific composition may also be increased or optimized by choice of delivery route. For example, the immunogenicity of compositions produced in accordance with the present invention that include a monoclonal antibody may be increased by choosing a mode of delivery that increases the direct contact between the binding agent and the antigen. The preferred route is intravenous, more preferably without adjuvant. An effective, but less preferred route is subcutaneous, more preferably with adjuvant. Those skilled in the art are conversant with the various choices available, and why one route might be chosen over another route for a particular binding agent.

One skilled in the art will also recognize that liposomes, nanospheres, micelles, or microspheres may be used to administer a composition, and that such administration may increase immunogenicity.

4. Photosensitizer

Compositions of the present invention may include one or more photosensitizers. Exemplary photosensitizers include, but are not limited to fluorescein, hematoporphyrin derivatives (e.g., Photofrin®), porphyrin derivatives, and perylenequinoid pigments. In a preferred embodiment of the invention, the photosensitizer comprises the use of perylenequinone (PQP) derivatives as photodynamic agents, and the use of PQP derivatives in immunophotodynamic therapy (IPT).

The invention also comprises a method of treating a disease by administering a therapeutically sufficient amount of at least one PQP derivative bound to a binding agent, and activating the conjugate, typically by photoactivating the PQP derivative. Typically, the PQP derivative may be activated by exposing the derivative to a pre-determined wavelength of light. The invention also includes a method of treating cancer which is enhanced in the presence of light wavelengths between about 400 nm and about 850 nm. Suitable PQPs include, but are not limited to those disclosed in U.S. Ser. No. 08/782,048, incorporated herein by reference. In a preferred embodiment of the invention, the PQP is hypocrellin B, molecules derived from HB, and compositions that include HB or one or more of its derivatives.

The desired characteristics for a PDT sensitizer comprise at least one or more of the following characteristics: good absorption of light in a wavelength that penetrates tissue to the desired depth (absorption in the 600 nm to 850 nm range penetrate the skin many millimeters), compound sensitive to pH—inactive, lower activity or activity destroyed at the pH characteristic of normal tissues, but active or higher activity at the pH of the cells or organisms to be treated; compound cleared from the body quickly and if a compound is intended to treat solid tumors it should have the ability to function either in the presence and/or absence of oxygen to address the problem of tumor cell hypoxia. The photosensitizer should have low dark cytotoxicity, and excellent photopotentiation of cellular damage. The PDT toxic effect may be mediated via necrotic, apoptotic cell death, or by stasis of the tumor vasculature or vascular bed.

5. Effectors

The present invention includes a composition comprising a binding agent bound to or used in conjunction with one or more effectors. As used herein, effector refers to a substance that affects the activity of the binding agent without binding to the substrate (or antigen) binding site.

A conceptually straightforward method to functionalize recombinant antibodies consists of sequentially fusing the antibody gene with the gene of a second protein, and expressing the resulting fusion protein as a single protein. Exemplary second proteins include but are not limited to:

a. A signal amplification moiety, such as a biotin mimetic sequence, which can be introduced at the C-terminus of a binding agent as a detection tag because of strong affinity of streptavidin-biotin;

b. Liposomes: fusion of certain amino acid sequences (with negative charges under physiologic condition) with a binding agent, such as single chain Fv-B43.13. Therefore, the fusion protein can easily be trapped by liposomes;

c. Cytokine sequences (e.g. IL-2): IL2 is a lymphokine synthesized and secreted primarily by T helper lymphocytes which have been activated by stimulation of the T cell receptor complex with antigen/MHC complexes on the surfaces of antigen-presenting cells. The response of T helper cells to activation is induction of the expression of IL2 and of IL2 receptors. IL2 possesses a variety of other activities which affect B cell growth and differentiation, formation of LAK cells, and augmentation of NK cells and enhancement of their cytolytic activity. Because of the central role of the IL2/IL2 receptor system in mediation of the immune response, it is obvious that manipulation of this system has important therapeutic implications. IL2 has already shown promise as an anti-cancer drug by its ability to stimulate the ujym hnhproliferation and activities of tumor attacking LAK and TIL cells.

d. Toxin: immunotoxins made by attaching a toxin (e.g. Pseudomonas extoxin and bacteria RNase) to the antibody or antibody fragments to produce cytotoxic molecules that selectively kill target tumor cell.

e. Enzyme: an antibody-directed enzyme pro-drug therapy system is a particularly attractive artificial effector method. In this approach, an antibody is used to target an enzyme to the tumor, and to retain it while the antibody-enzyme conjugate clears from normal tissues. A non-toxic pro-drug is then administrated, and this is activated by the enzyme to produce a cytotoxic drug at the tumor site.

f. Radionuclide chelator: any peptide that binds to a radionuclide chelator, e.g., metallothionein (MT). MT is a ubiquitous, low-molecular weight, metal-binding protein that participates in metal metabolism and detoxification. Mammalian forms of MT bind seven ions in tetrahedral metal-thiolate clusters, including technetium and other metals useful for targeted radiodiagnosis or therapy.

g. A phagocytosis enhancer, e.g., tuftsin. Tuftsin is natural tetrapeptide (Thr-Lys-Pro-Arg) that was found to manifest several biological activities, including activation of macrophages/monocytes and stimulation of phagocytosis. It has a wide spectrum of immunoadjuvant activities which it exerts on the phagocytic cells, the polymorphonuclear leukocyte, the monocyte and the macrophage. In animal and clinical studies, tuftsin has displayed anti-tumor and anti-infection activity with no detectable toxicity.

The fusion protein scFv-tuftsin was defined as a recombinant fusion protein that is composed scFv antibody binding domain connected with tuftsin by an artificial linker. This bifunctional protein was designed to achieve higher specific anti-idiotypic immunogenicity.

Method

In an embodiment of the invention, MAb B43.13, directed against a first epitope on the multi-epitopic antigen CA 125, induces an immune response against CA 125 through one or more second epitopes on the CA 125 antigen. In a preferred embodiment of the invention, any of the second epitopes are cryptic or previously inaccessible epitopes that are exposed or available for interacting with a component of the immune system reaction after MAb B43.13 binds to the antigen. Cryptic or previously inaccessible refers to an epitope or binding site on the pre-determined antigen that does not activate or stimulate the immune system when the antigen is unbound by a binding agent according to the invention.

As used herein, "administering" refers to any action that results in exposing or contacting a composition containing a binding agent with a pre-determined cell, cells, or tissue, typically mammalian. As used herein, administering may be conducted in vivo, in vitro, or ex vivo. For example, a composition may be administered by injection or through an endoscope. Administering also includes the direct application to cells of a composition according to the present invention. For example, during the course of surgery, tumor cells may be exposed. In accordance with an embodiment of the invention, these exposed cells (or tumors) may be exposed directly to a composition of the present invention, e.g., by washing or irrigating the surgical site and/or the cells.

For diseases that can be characterized in part by having a tumor-associated antigen that is multi-epitopic, one embodiment of the present invention involves contacting a soluble antigen with a binding reagent (BA) that specifically binds to a single epitope on the multi-epitopic tumor-associated antigen.

In accordance with a method of the invention, the binding agent must be capable of binding a pre-determined binding site or receptor, and may be administered to the patient by any immunologically suitable route. For example, the binding agent may be introduced into the patient by an intravenous, subcutaneous, intraperitoneal, intrathecal, intravesical, intradermal, intramuscular, or intralymphatic routes. The composition may be in solution, tablet, aerosol, or multiphase formulation forms. Liposomes, long-circulating liposomes, immunoliposomes, biodegradable microspheres, micelles, or the like may also be used as a carrier, vehicle, or delivery system. Furthermore, using ex vivo procedures well known in the art, blood or serum from the patient may be removed from the patient; optionally, it may be desirable to purify the antigen in the patient's blood; the blood or serum may then be mixed with a composition that includes a binding agent according to the invention; and the treated blood or serum is returned to the patient. The clinician may compare the anti-idiotypic and anti-isotypic responses associated with these different routes in determining the most effective route of administration. The invention should not be limited to any particular method of introducing the binding agent into the patient.

Administration may be once, more than once, and over a prolonged period. As the compositions of this invention may be used for patient's in a serious disease state, i.e., life-threatening or potentially life-threatening, excesses of the binding agent may be administered if desirable. Actual methods and protocols for administering pharmaceutical compositions, including dilution techniques for injections of the present compositions, are well known or will be apparent to one skilled in the art. Some of these methods and protocols are described in *Remington's Pharmaceutical Science*, Mack Publishing Co. (1982).

A binding agent may be administered in combination with other binding agents, or may be administered in combination with other treatment protocols or agents, e.g., chemotherapeutic agents.

The effectiveness of the proteins of the present invention may be monitored in vitro or in vivo. Humoral responses may be monitored in vitro by conventional immunoassays, where the anti-tumor activity of the response may be determined by complement-mediated cytotoxicity and/or antibody-dependent cellular cytotoxicity (ADCC) assays. The assay methodologies are well known, and are described in *Handbook of Experimental Immunology*, Vol. 2, Blackwell Scientific Publications, Oxford (1986). Other assays may be directed to determining the level of the antigen in the patient or tissue. Cell-mediated immunity may be monitored in vivo by the development of delayed-type hypersensitivity reactions, or other in vivo or in vitro means known to those skilled in the art, including but not limited to the skin test reaction protocol, lymphocyte stimulation assays, measuring the toxicity of a subject's lymphocytes to tumor cells by using a standard cytotoxicity assay, by a limiting dilution assay, or by measuring plasma levels of cytokines using standard ELISA assays.

Determining the effectiveness of a specific binding agent-antigen pair may also be accomplished by monitoring cell killing. Those skilled in the art will recognize that there are a variety of mechanisms that are proof of cell killing. As shown in the Examples, cell killing may be demonstrated by showing that Ab3 mediates ADCC, that Ab1 and HAMA mediates CDC, that natural killer (NK) cells are produced, and/or that cytotoxic T lymphocytes (CTLs) are produced.

EXAMPLES

Example 1

Antibody Mediated Immunotherapy Influence of Circulating Antigen in Inducing Antigen Specific Anti-Tumor Immune Responses

This example demonstrates the use of antigen-specific murine monoclonal antibodies to induce an immune response against an immune-suppressive tumor-associated antigen. Injecting an antibody against a specific epitope in a multi-epitopic antigen can lead to immune responses against various other epitopes on this antigen.

In an attempt to understand the mechanism of action of MAb-B43.13, various immunological parameters were studied in ovarian cancer patients injected with this antibody. These studies clearly demonstrated activation of both the humoral and cellular anti-cancer immune responses.

The generation of human CA125-binding antibodies was measured before MAb-B43.13 injection and correlated to pre-injection CA125 levels as well as to survival data. Table 1 shows that generation of anti-CA125 antibodies correlates with CA125 pre-injection levels. Circulating CA125 affects the development of anti-CA125 antibodies only when patients received the MAb-B43.13 injection. If anti-CA125 antibodies before injection of MAb-B43.13 are compared between patients with low or high CA125 values (below or above 105 U/mL), no difference was found between the two groups (Table 1). A minimum concentration of 105 U/mL of CA125 was chosen as representing a significant amount of CA 125.

Tumor killing either through an anti-CA125 antibody-mediated ADCC mechanism or through CA125-specific CLTs, lead to increased survival in patients injected with MAb-B43.13. Although high levels of serum CA125 have been suggested to be a poor prognostic indicator, they seem to have a beneficial effect in combination with the injection of anti-CA125 antibody in such patients. For example, when the CA125 levels were more than 105 units/mL, immune response against CA 125 increased by more than 20% which in turn increased the median survival in those patients from 39.1 months to 54.5 months (Table 1). Thus the injection of a binding agent to a patient containing elevated levels of multi-epitopic soluble antigen leads to antigen specific humoral and cellular response which in turn leads to tumor killing followed by improved survival.

TABLE 1

Correlation between Serum CA125 Levels, Human Anti-CA125 ($Ab_1'$) Response and Survival in Patients Injected with MAb-B43.13

| Preinjection Serum CA125 Level | %-age of Patients with Human Anti-CA125 Response | Mean Survival in Month |
|---|---|---|
| <105 U/mL | 10.3% | 39.1 |
| >105 U/mL | 32.6% | 54.5 |

TABLE 2

Correlation between Serum CA125 Levels and Antibody Levels in Patients Injected with MAb-B43.13.

| Pre-injection Serum CA125 Level | Anti-CA125 Antibody Titre (No. of Positive/Total Patients) |
|---|---|
| <105 U/mL | 3/29 |
| >105 U/mL | 15/46 |

The correlation between CA125 antibodies and survival, with a CA 125 cut-off of 105 U/ml is shown in Table 3.

TABLE 3

| | n | anti-CA125 Antibodies mean ± SD [ng/ml] | P | [-fold increase] | P | mean ± SD [months] | Survival median | p |
|---|---|---|---|---|---|---|---|---|
| Anti-CA125 Non-Responders | 27 | 61.8 ± 25.1 | 0.0031 | 1.3 ± 0.7 | <0.0001 | 34.8 ± 18.2 | 34.0 | <0.0001 |
| Anti-CA125 Responders | 20 | 346.4 ± 376.3 | | 7.4 ± 5.1 | | 67.6 ± 27.0 | 67.0 | |
| CA125 < 105 U/ml | 19 | 94.0 ± 61.0 | 0.0213 | 2.4 ± 1.3 | 0.0089 | 46.1 ± 26.8 | 40.5 | 0.7369 |
| CA125 > 105 U/ml | 28 | 239.8 ± 308.8 | | 5.3 ± 5.2 | | 50.5 ± 28.3 | 44.5 | |
| Anti-CA125 Non-Responders | | | | | | | | |
| CA125 < 105 U/ml | 12 | 53.8 ± 12.0 | 0.1146 | 1.6 ± 0.7 | 0.8448 | 38.5 ± 23.5 | 37.5 | 0.4945 |
| CA125 > 105 U/ml | 15 | 68.2 ± 31.0 | | 1.5 ± 0.7 | | 31.8 ± 12.6 | 30.0 | |
| Anti-CA125 Responders | | | | | | | | |
| CA125 < 105 U/ml | 7 | 162.9 ± 46.1 | 0.0152 | 3.9 ± 0.4 | 0.0009 | 51.9 ± 24.0 | 45.0 | 0.0572 |
| CA125 > 105 U/ml | 13 | 445.2 ± 357.8 | | 9.6 ± 4.7 | | 76.0 ± 25.4 | 82.0 | |
| CA125 < 105 U/ml | | | | | | | | |
| Anti-CA125 Non-Responders | 12 | 53.8 ± 12.0 | 0.0006 | 1.6 ± 0.7 | <0.0001 | 38.5 ± 23.5 | 37.5 | 0.2718 |
| Anti-CA125 Responders | 7 | 162.9 ± 46.1 | | 3.9 ± 0.4 | | 51.9 ± 24.0 | 45.0 | |
| CA125 > 105 U/ml | | | | | | | | |
| Anti-CA125 Non-Responders | 15 | 68.2 ± 31.0 | 0.0025 | 1.5 ± 0.7 | <0.0001 | 31.8 ± 12.6 | 30.0 | <0.0001 |
| Anti-CA125 Responders | 13 | 445.2 ± 357.8 | | 9.6 ± 4.7 | | 76.0 ± 25.4 | 82.0 | |

In an attempt to understand the mechanism behind anti-CA125 antibody formation by MAb-B43.13 injection in cancer patients, we characterized the human anti-CA125 antibodies present in their sera. For example, if the anti-CA125 antibodies were generated in the manner suggested by the idiotypic network, MAb-B43.13 would generate anti-MAb-B43.13 antibodies, some of which would exactly mimic the CA125 antigen (=Ab2β). These in turn can generate anti-CA125 antibodies (=Ab3). The Ab3 generated through this pathway would bind to the same epitope on CA125 as the Ab1 (=B43.13) and therefore compete with the binding of MAb-B43.13 to the antigen.

On the other hand, antibodies generated through the antigen itself will bind to various epitopes available on the antigen. If the anti-CA125 antibodies were generated in a manner suggested by the present invention, the pathway would follow Ab1+soluble antigen→Ab1c. Following this scheme, MAb-B43.13 (Ab1) would bind the CA125 serum antigen, which would in turn generate an anti-CA125 antibody (Ab1c). Furthermore, the Ab1c antibodies generated under this pathway would bind and be inhibited by other anti-CA 125 antibodies, such as B27.1 or M11, because, as noted above, CA125 is multi-epitopic and B43.13, M11, and B27.1 epitopes are distinct. Also, Ab1c will not bind to anti-MAb-B43.13 antibodies.

Analysis of the serum samples with positive anti-CA125 titer demonstrated that their binding to CA125 could be inhibited not only by MAb-B43.13 single chain antibody but also by F(ab') fragments of other anti-CA125 antibodies, B27.1 and M11, that recognize epitopes on CA125 which are different from B43.13 (Tables 3 and 4). Sera from only two patients were considered to contain anti-CA125 antibodies that were exclusively generated via idiotype induction of MAb-B43.13 (=Ab3) i.e. anti-CA125 antibodies that could only and completely be inhibited with MAb-B43.13 and bound to polyclonal rabbit Ab2.

Thus, if the patients serum contained anti-CA125 antibodies that were inhibitable by MAb-B43.13 only, it was classified as containing Ab3; those inhibitable by MAb-B27.1 were classified as Ab1c. In other words, injecting a binding agent such as an antibody against a single epitope on a multi-epitopic antigen leads to generation of a humoral and cellular response against a different epitope on the antigen.

The presence of a multi-epitopic anti-CA125 response in sera of MAb-B43.13 treated patients with high CA125 levels make us believe that, besides anti-idiotype induction, other mechanisms exist to induce an immune response against tumor-associated antigens. In this scenario, the injected antibody forms a complex with the circulating antigen in vivo. This process can cause several effects. The complexation of the antigen by antibodies can facilitate the uptake of CA125 by professional antigen-presenting cells (APC) and thus render the antigen more immunogenic. The complexing antibody—in our case from a murine source—could also function as an adjuvant, adding a foreign component to the self-antigen CA125 that might facilitate recognition by the immune system. Epitopes of the antigen are blocked by the complexing antibody and are either protected from processing or processed at different sequences thus creating new peptides for MHC-binding. It is also possible that a conformational change in the antigen takes place upon antibody binding thereby exposing new epitopes to the immune system, including sub-dominant or immune-dormant epitopes.

It is interesting to note that the complex formation between CA125 and MAb-B43.13 has also been observed during pharmacokinetic studies, as determined by drop in circulating CA125 levels upon injection of MAb-B43.13. When patients received more than one injection and patients developed high amounts of human anti-mouse antibodies (HAMA), the antibody showed rapid clearance to liver and spleen, as demonstrated in immunoscintigraphic studies. Antigen-antibody complexes, accumulated in lymphoid centers like the spleen, are known to be very efficiently presented to T cells by antigen-presenting cells, such as B cells, macrophages, or dendritic cells.

Augmentation of antigen processing and presentation by immune complexing has been demonstrated in several systems. Targeting tetanus toxoid to FcγR by complexing with anti-tetanus toxoid IgG results in a 10-1000-fold increase in processing and presentation of this antigen as measured by $T_H$ cell activation. A similar increase in immunogenicity was observed with hepatitis B antigen complexed with its corresponding antibody. Also the natural presence of antibodies against α-galactosyl epitopes has been used to augment tumor vaccine immunogenicity in α-galactosyl-modified tumor-associated antigens.

It was observed that MAb-B43.13 has a protective effect on its CA125 epitope during antigen processing by the immune system. The MAb-B43.13 epitope was recognized by almost all antiCA125 antibody samples from patients (inhibition in 78% of the samples, Table 4).

Figure 3:
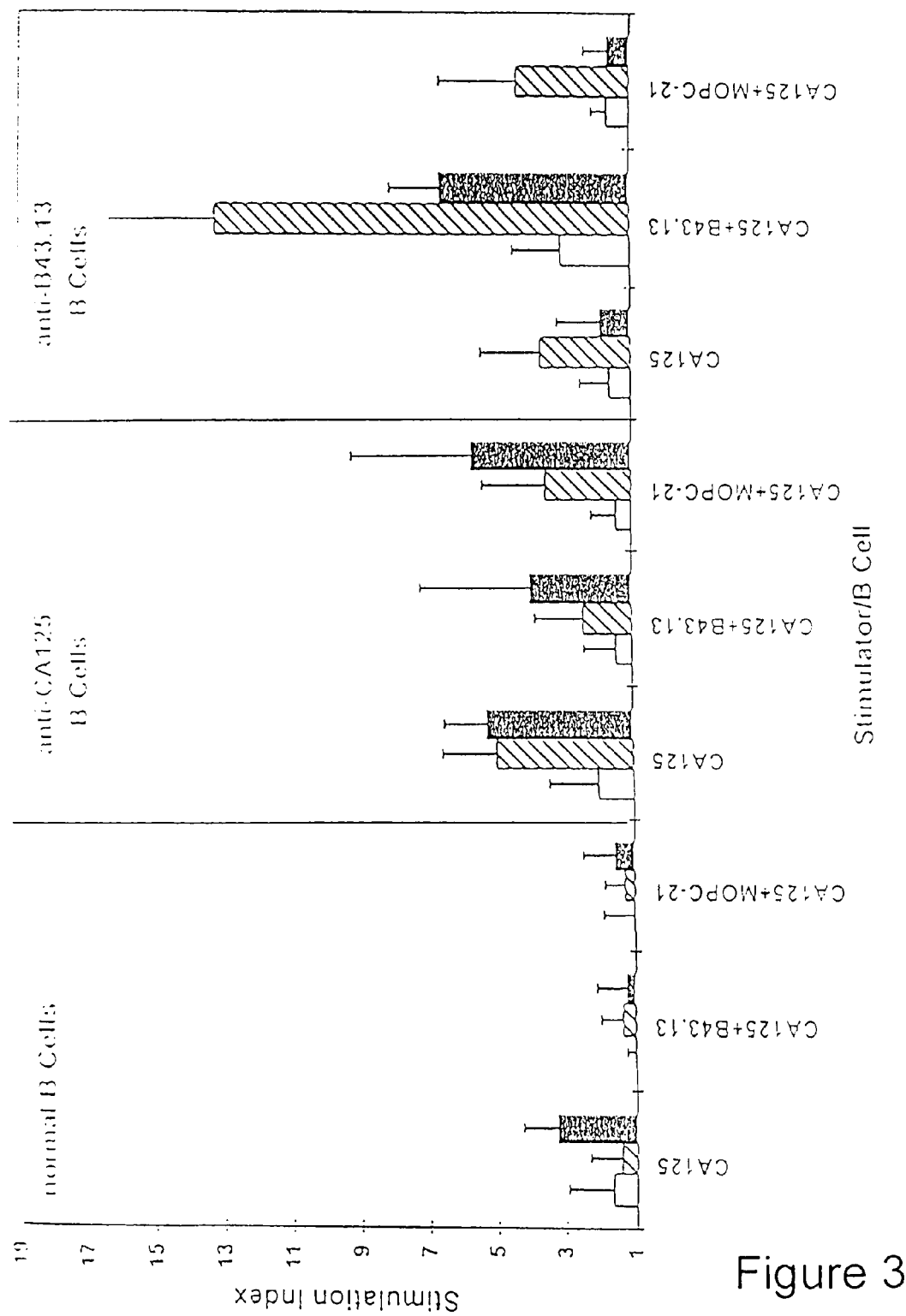
FIG. 3 shows the production of B cells in response to the administration of a composition of the invention. Legend: open bars, 0.1 μg or kU per mL; hatched bars, 1 μg or kU per mL; closed bars, 10 μg or kU per mL.
Figure 6:
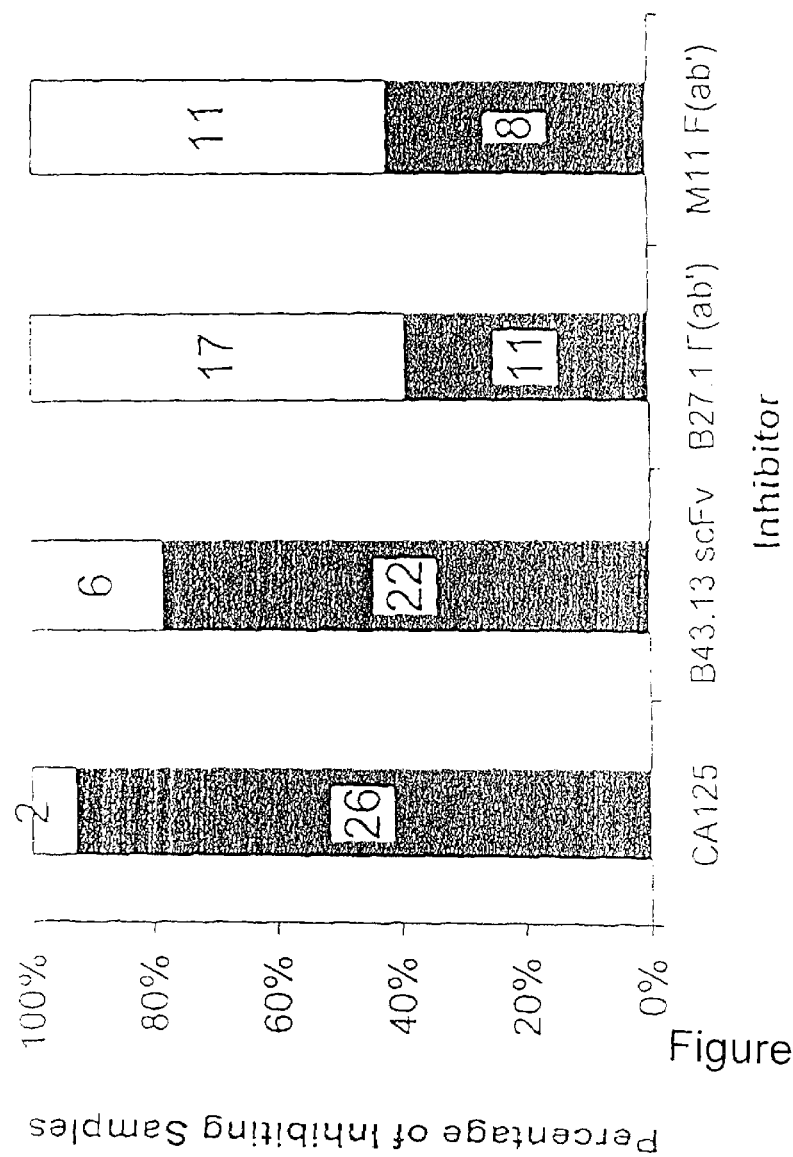
FIG. 6 shows the characterization of anti-CA 125 antibodies from patients injected with MAb B43.13. Anti-CA 125 positive samples were tested for inhibition of their binding to CA 125 (solid phase) by CA 125, MAb-B43.13 scFv, MAb-B27.1 F(ab'), or MAb M11 F(ab'). Single chain MAb-B43.13, F(ab') MAb-B27.1, and F(ab') M11 were used in the inhibition studies to avoid non-specific inhibition of the Fc portion of the antibody and cross-reactivity due to HAMA. To be considered to be significant, inhibition had to be at least 15%.

The reverse seems to be true as well, i.e. CA125 has conserving properties on the idiotope of MAb-B43.13 during the antigen processing event. The increased formation of Ab2 in mice immunized with the CA125-MAb-B43.13 complex compared to mice immunized with MAb-B43.13-KLH (FIG. 3) and the increased Ab2 production in MAb-B43.13 injected patients with CA125 titers above 105 U/mL confirm this observation. See Table 4 and FIG. 6 for a summary and Table 5 for the details of these results. Sera from these patients were analyzed for the presence of human anti-CA125 antibodies by their ability to bind to CA125 [R. Madiyalakan et al, *Hybridoma*, 14:199-203 1995) and Schultes et al., *Cancer Immunology and Immunotherapy* 46:201-212 (1998)]. Antibody purified from pooled patients' sera were found to inhibit B43.13 in similar assays, but not B27.1. The explanation for this anomaly is yet to be determined. However, it has been confirmed using M11 antibodies that B43.13 binds to a distinct epitope, and that upon binding with B43.13, CA 125 is in fact recognized by the immune system.

TABLE 4

| CA125 10500 U/ml | B43.13 scFv 1 μg/ml | B27.1 F(ab') 1 μg/ml | M11 F(ab') 1 μg/mL |
|---|---|---|---|
| Inhibition No. of Positives/Total (%) | | | |
| 26/28 (92.8) | 22/28 (78.6) | 11/28 (39.3) | 8/19 (42.1) |

TABLE 5

Characterization of Anti-CA125 Antibodies in Patients Injected with MAb-B43.13

| Patient | Inj. # | days post-inj. | Anti-CA125 Ab levels (ng/mL) | Binding to anti-MAb B43-13 (AB2)† | Inhibition (%)[1] | | | | Classification |
|---|---|---|---|---|---|---|---|---|---|
| | | | | | CA125 10000 U/mL | B43.13 ScFv[2] 10 µg/mL | B27.1 F(ab')[2] 1 µg/mL | M11 F(ab')[2] 1 µg/mL | |
| 1 | 3 | 0 | 14.8 | + | 62.3 | 42.6 | 5.8 | 2.3 | Ab3 |
| 2 | 1 | 185 | 9.5 | — | 21.6 | −46.9[3] | −86.9[3] | 24.3 | Ab1c |
| 3 | 2 | 239 | 45.4 | + | 89.7 | 95.3 | 12 | ND | Ab3 |
| | 3 | 86 | 25.4 | + | 80.2 | 84.4 | −.05[3] | 2.1 | Ab3 |
| | 3 | 207 | 48.7 | + | 91.4 | 94.0 | −9.1[3] | ND | Ab3 |
| | 4 | 144 | 79.7 | + | 77.1 | 93.0 | 3.5 | 4.5 | Ab3 |
| | 4 | 270 | 30.9 | + | 79.2 | 83.0 | −55.8[3] | ND | Ab3 |
| | 4 | 309 | 16.7 | + | 77.0 | 83.0 | −55.8[3] | ND | Ab3 |
| | 5 | 45 | 16.0 | + | 51.6 | 50.9 | 34.8 | ND | Ab3/Ab1c |
| | 5 | 134 | 64.1 | + | 89.1 | 83.3 | −37.3[3] | −2.3 | Ab3 |
| 4 | 2 | 15 | 23.6 | − | 62.3 | −84.8[3] | −101.9[3] | 18.5 | Ab1c |
| | 2 | 41 | 21.6 | − | 56.9 | 20.2 | −7.0[3] | ND | Ab1c |
| | 2 | 76 | 23.1 | − | 63.6 | 29.4 | 4.5 | ND | Ab1c |
| | 3 | 28 | 11.1 | — | 24.2 | 4.7 | 11.1 | 35.6 | Ab1c |
| 5 | 1 | 16 | 15.5 | + | 74.8 | 78.3 | 39.9 | −12.5 | Ab1c/Ab3 |

| Patient | Inj. # | days post-inj. | Anti-CA125 Ab levels (ng/mL) | Binding to anti-MAb B43-13 (AB2)† | Inhibition (%)[1] | | | | Classification |
|---|---|---|---|---|---|---|---|---|---|
| | | | | | CA125 10000 U/mL | B43.13 ScFv[2] 10 µg/mL | B27.1 F(ab')[2] 1 µg/mL | Mu F(ab')[2] 1 µg/mL | |
| 6 | 3 | 0 | 10.3 | + | 54.0 | 60.2 | 22.7 | 1.5 | Ab1c/Ab3 |
| 7 | 3 | 0 | 14.9 | — | 29.7 | −70.2[3] | −358.9[3] | ND | Ab1c |
| 8 | 3 | 7 | 59.1 | — | 77.1 | 87.1 | 34.9 | 12.5 | Ab1c |
| | 3 | 17 | 46.9 | − | 78.4 | 86.5 | 40.7 | 9.6 | Ab1c |
| 9 | 3 | 112 | 9.2 | − | −66.4[3] | 16.0 | 20.2 | 45.6 | Ab1c |
| | 3 | 166 | 8.5 | − | −18.4[3] | 42.5 | 56.5 | 33.8 | Ab1c |
| 10 | 3 | 0 | 41.5 | — | 30.8 | 39.2 | 20.0 | 57.8 | Ab1c |
| 11 | 5 | 134 | 8.8 | − | 19.0 | 24.4 | 3.5 | −6.5 | Ab1c |
| | 6 | 134 | 8.7 | − | 18.0 | 39.0 | 46.0 | ND | Ab1c |
| | 9 | 26 | 13.4 | − | 54.5 | 19.3 | 11.1 | ND | Ab1c |
| | 9 | 65 | 13.3 | − | 56.1 | 24.4 | 3.7 | ND | Ab1c |
| | 10 | 40 | 9.4 | — | 61.4 | 37.0 | 33.4 | 2.3 | Ab1c |
| 12 | 2 | 14 | 10.6 | − | 24.5 | −54.4[3] | 19.9 | 65.8 | Ab1c |
| 13 | 1 | 15 | 11.5 | − | 30.8 | 47.4 | 55.8 | 2.5 | Ab1c |
| 14 | 2 | 17 | 10.1 | − | 30.3 | −51.2[3] | 1.2 | 32.4 | Ab1c |

[1]To be considered to be significant, inhibition has to be at least 15%
[2]Single chain MAb-B43.13, F(ab') MAb-B27.1, and F(ab') M11 were used in the inhibition studies to avoid non-specific inhibition due to the Fc portion of the antibody and cross-reactivity due to HAMA.
[3]This experiment produced an anomalous result, as evidenced by the negative number, the reasons for which have yet to be determined.
†Anti-MAb-B43.13 (Ab2) was purified from rabbits injected with MabB43.13.
ND = not determined. NA = not applicable Therefore, complex formation can lead to enhanced anti-CA125 as well as anti-idiotypic antibody formation. Manca et al., J. Immunol. 140:2893 (1988) and Ling et al., Immunology 62:7 (1987) have shown that antibodies can preserve the sequence of their epitope during antigen-processing and antibodies have been used to raise immune responses to less immunogenic epitopes of an antigen.

Figure 4:
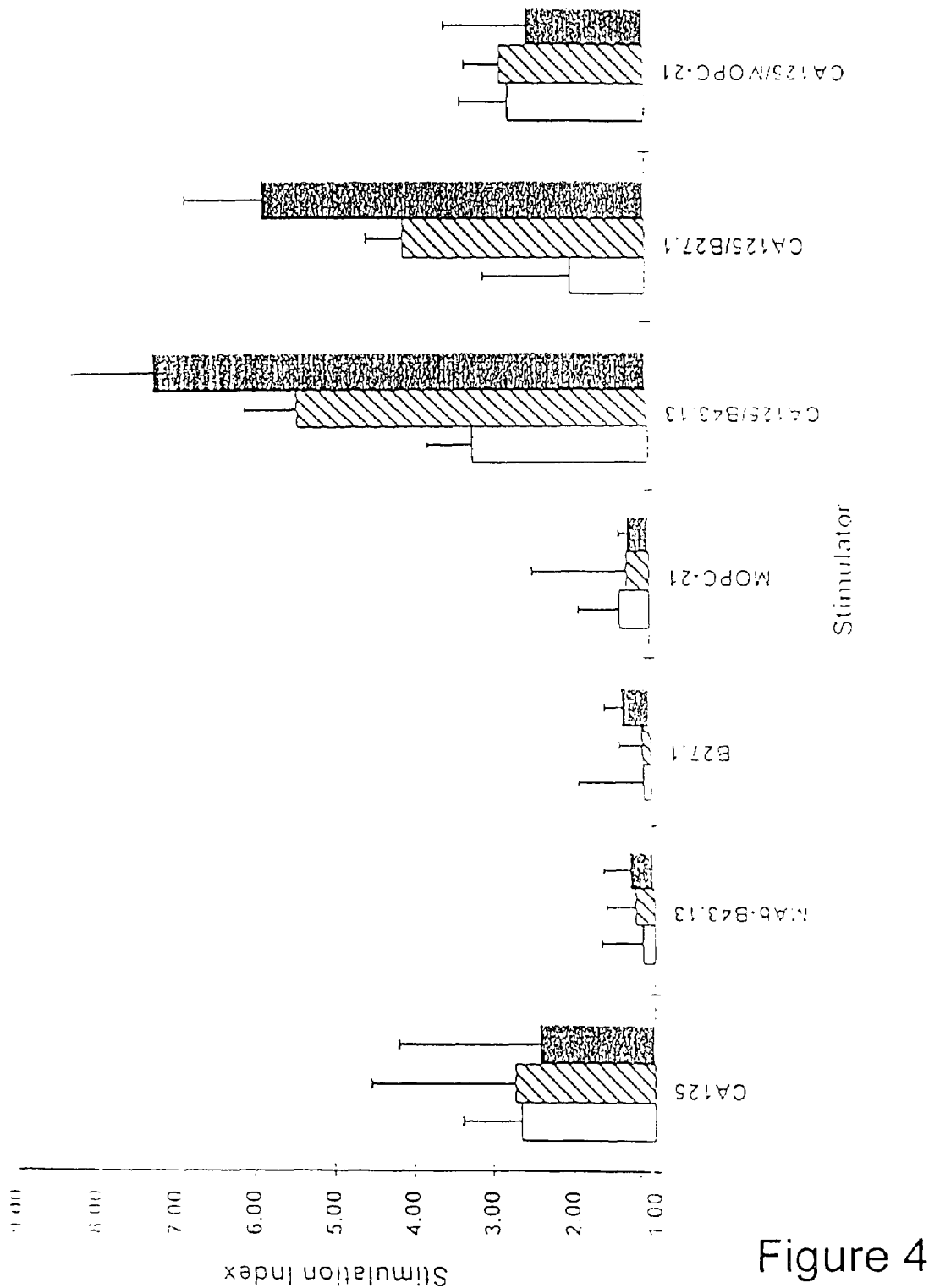
FIG. 4 shows that a binding agent/antigen complex stimulates an immune response. Legend: open bars, 0.1 μg or kU per mL; hatched bars, 1 μg or kU per mL; closed bars, 10 μg or kU per mL.

Enhanced antigen-presentation of antigen-antibody complexes was attributed to facilitated antigen uptake via the Fcγ-receptor (macrophages, dendritic cells) or membrane-bound Ig (B cells) on professional antigen-presenting cells (APC). The human FcγRI and RIII-receptor on macrophages and dendritic cells does not bind murine IgG$_1$, but the human FcγRII, which mediates phagocytosis and pinocytosis of small immune complexes, has strong affinity to this murine IgG isotype. Accordingly, various professional APC can be involved in the preferential presentation of the CA125-MAb-B43.13 complex. We tested B cells with two different specificities as well as macrophages as APC: CA125-specific B cells (from mice immunized with CA125) and anti-MAb-B43.13-specific B cells (from mice immunized with MAb-B43.13). Normal B cells served as control. When the proliferation of CA125-specific T cells was monitored by [methyl-$^3$H]-Thymidine uptake, optimal stimulation was observed in MAb-B43.13 specific B cells, primed with the CA125-MAb-B43.13 complex (FIG. 3), followed by presentation of CA125 by CA125-specific B cells. Enhanced presentation of immune complexes by macrophages and dendritic cells is mediated by preferential uptake via the FcγR. FIG. 4 confirms that CA125 is presented more efficiently by macrophages, if complexed with an antigen specific antibody.

Figure 5:
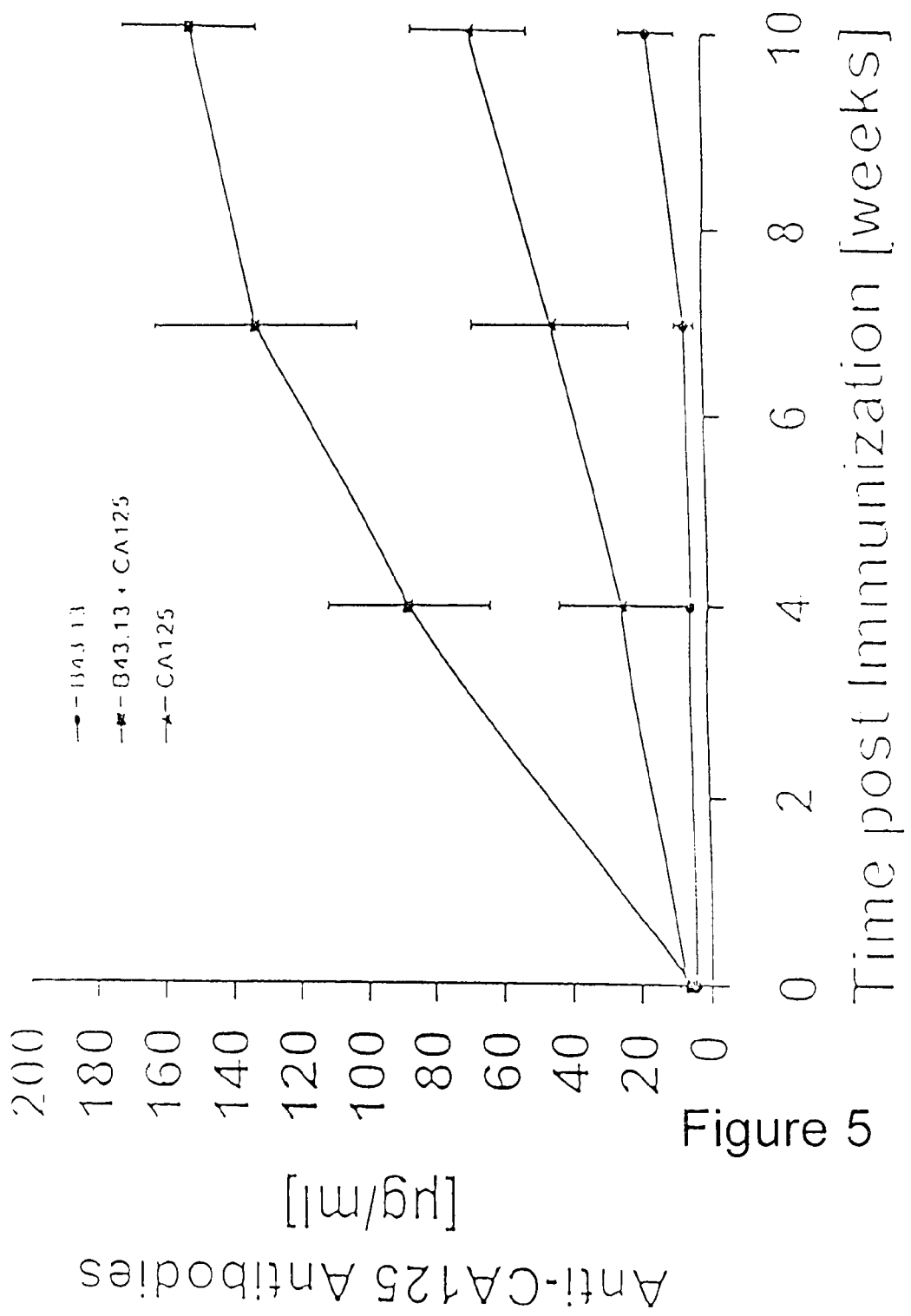
FIG. 5 shows the ability of a composition of the invention to increase the immunogenicity of its target antigen. Legend: ●, MAb 43.13; ■, MAb 43.13+CA 125; ▲, CA 125.

The ability of MAb B43.13 to increase the immunogenicity of CA 125 was studied in a mouse model by immunizing a mouse with the CA 125-MAb 43.13 complex, compared to CA125 or MAb B43.13 alone as the immunogen. When the mouse sera was analyzed for anti-CA125 antibody levels, the mice injected with the antigen-antibody complex had the highest titers (see FIG. 5). This supports the observation that interaction of the antigen with a specific antibody leads to a higher antigen specific humoral immune response compared to antibody or antigen alone.

These results clearly indicate that when an antibody against a single epitope (B43.13) was injected into a patient, an antibody response against the whole antigen is generated which recognizes different epitopes present in the antigen. In other words, injecting a binding agent such as a monoclonal antibody to a soluble multi-epitopic antigen into a patient having a functioning immune system generates an antibody to the antigen, where the generated antibody is inhibited by antibodies to different epitopes.

Example 2

Similarly, injecting the binding agent to the cancer patients having circulating CA125 lead to antigen specific CTL's. Peripheral Blood Mononuclear Cells (PBMC) from eight patients injected with MAb-B43.13 were tested for cytotoxicity against CA125 positive or CA125 negative ovarian tumor cells in a chromium release assay. The results are shown in Table 6. The specificity of the lysis was confirmed by the ability of MAb-B43.13 to inhibit such lysis, as well as the inability to kill CA125 negative tumor cells. Of the 8 patients who received MAb-B43.13, at least four patients (#5 to #8) were determined to have CA125 specific cytotoxic T lymphocytes (CTL's) in their blood. The generation of CA125 specific CTL's are likely to kill ovarian tumor cells in patients.

Example 3

Immunotherapy of Human Ovarian Carcinoma in an Animal Model

In order to investigate the therapeutic effectiveness, MAb-B43.13 was tested in a human-PBL-SCID/BG mouse model. Mice were reconstituted with human-PBL(normal donors) by i.p. injection of 2 to 3×10$^7$ PBL/mouse. MAb-B43.13 was administered at 100 μg/mouse in PBS, in different experimental set-ups. An isotype matched control antibody (MOPC21 or MAb-170) and PBS injection served as controls. The ovarian cancer cells NIH: OVCAR-Nu3 were injected i.p. at 1×10$^6$ cells/mouse or s.c. at 4×10$^6$ cells/mouse. Hu-PBL-SCID/BG mice were either immunized before injection of tumor cells, or after small tumors were established (two weeks after transplantation). In another experiment, tumor-bearing mice (s.c.) were injected with MAb-B43.13 two weeks after tumor transplantation, along with PBL.

Antibody injections were repeated twice in 2-week intervals. Functional and cellular characterization of serum and PBL from these mice demonstrated the successful engraftment of a human immune system in those mice.

All three experiments showed that MAb-B43.13 treatment could: a) delay or prevent development of tumors; b) reduce the size of small, established tumors (s.c. tumor injection) or suppress ascites production; c) delay tumor growth when injected prior to tumor implantation and d) prolong the survival of mice (i.p. tumor injection).

Human tumor infiltrating lymphocytes (TIL) were identified in mice using flow cytometry, which might contribute to the in vivo anti-tumor activity of MAb-B43.13.

At the endpoints of the therapy study, surviving mice from different treatment groups were euthanized. Blood, spleen, tumor, and peritoneal washes were obtained form the measurement of human immunoglobulin as well as flow cytometric analysis of human PBL in mouse tissues. Tumors were also analyzed by immunohistochemistry.

TABLE 6

Cytotoxicity In Patients Injected With A Vaccine Containing MAb-B43.13

| PATIENT ID | Injection Number | Days Post Injection | CAOV-4 | SK-OV-3 | K562 | PERCENT INHIBITION BY MAb-B43.13 (5 μg) | PERCENT DIFFERENCE BETWEEN CA 125 positive and CA 125 negative CELLS |
|---|---|---|---|---|---|---|---|
| 1 | 2 | 17 | 2.0 | 0.0 | 3.7 | ND* | insignificant |
| 2 | 2 | 0 | 9.8 | 7.5 | 33.5 | ND | 31 |
| 3 | 3 | 0 | 22.8 | 20.4 | 64.3 | ND | 12 |
| 4 | 3 | 0 | 25.8 | 20.2 | 44.5 | 4.7 | 28 |
| 5 | 3 | 0 | 65.1 | 45.4 | 80.7 | ND | 43 |
| 6 | 3 | 0 | 23.1 | 20.0 | 42.0 | 19.2 | 16 |
|  | 3 | 6 | 7.4 | 5.2 | 10.2 | 53.0 | 42 |
| 7 | 4 | 355 | 10.3 | 3.1 | 18.9 | ND | 23 |
| 8 | 10 | 425 | 25.5 | 18.2 | 39.2 | 15.4 | 40 |

*ND = Not Done due to lack of sufficient lymphocytes
Results are the mean of one experiment performed in triplicate

Example 5

Induction of Idiotypic Network to Anti-MUC-1 Antibody in Breast Cancer

Figure 7:
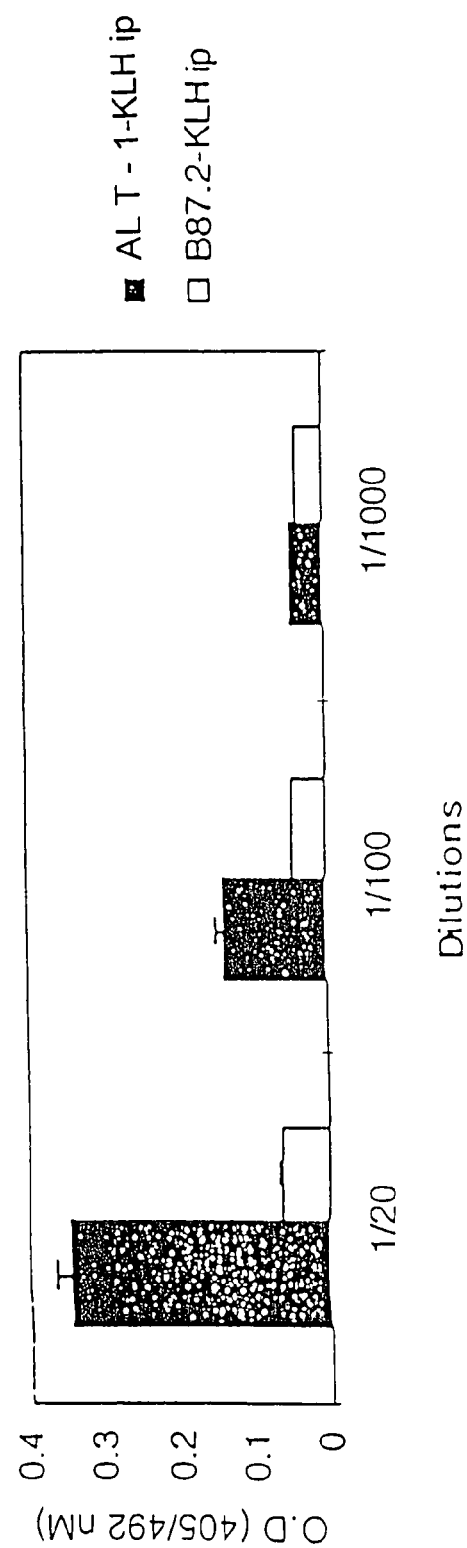
FIG. 7 shows a humoral response generated by an anti-MCV-1 antibody.
Figure 8:
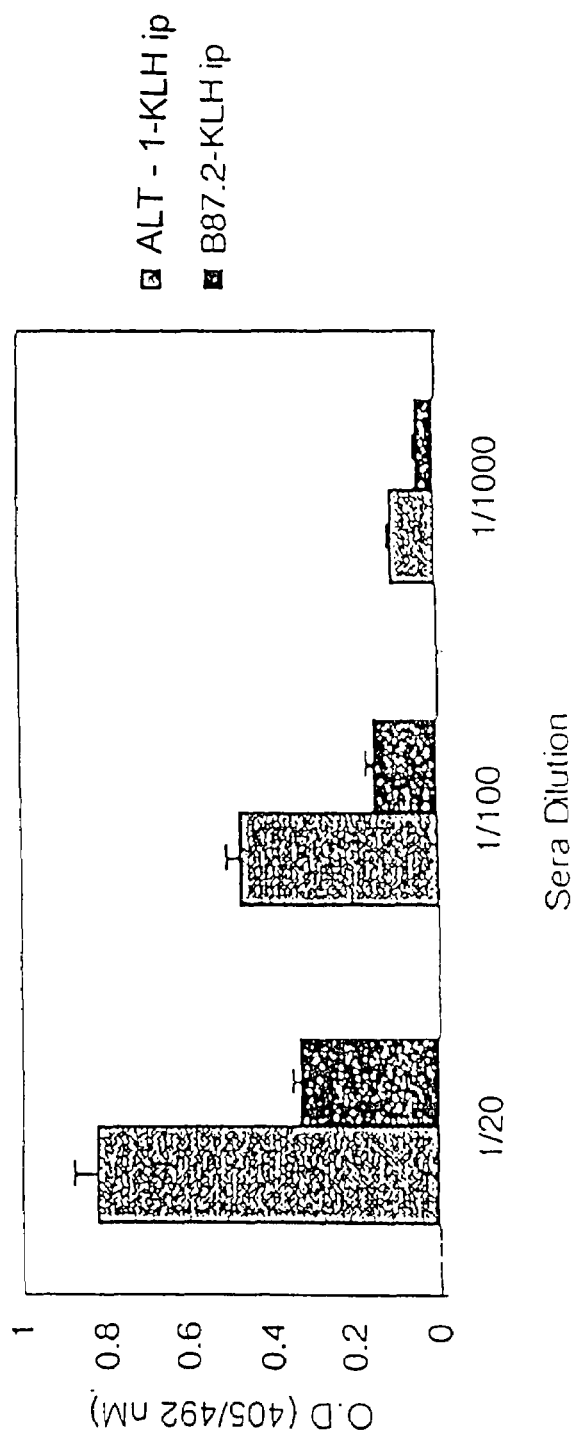
FIG. 8 shows a humoral response generated by a composition of the invention directed against breast cancer.

MUC-1 proteins (polymorphic epithelial mucin) expressed on malignant epithelium are under-glycosylated, which leads to exposure of novel T and B cell epitopes. An anti-MUC-1 murine clone, Alt-1, was generated by immunization of mice with CA15.3 antigen, a glycoprotein consisting of an MUC-1 protein and carbohydrate, and characterized for its binding specificity to CA15.3 by ELISA and to MUC-1 transfectoma by FACS analysis. Injection of MAb-Alt-1 (Ab1) conjugated to KLH into mice carrying MUC-1 transfectoma resulted in anti-idiotypic antibody (Ab2) (FIG. 7) and anti-anti-idiotypic antibody (Ab3) production (FIG. 8). A minimum of four injections at a dose of 50 µg/mouse resulted in a measurable humoral response. The Ab2 and Ab3 levels reached their peak after six injections. The anti-idiotypic antibody (Ab2) competed with the native antigen, CA15.3. T-cell proliferation studies showed specific response to the injected antibody and CA15.3 indicating the presence of idiotype specific T-cells (T2) and anti-idiotype specific T cells (T3).

In addition, a breast tumor model was developed using a human MUC-1 gene transfected mouse mammary carcinoma, 413BCR. Groups of mice were treated with Alt-1-KLH or human immunoglobulin conjugate, and compared to appropriate positive control (liposomal MUC-1) and negative control (murine immunoglobulin). Immunizations were performed twice before or after tumor implantation at weekly intervals. The tumor volumes were measured weekly and the growth rates assessed.

A significant tumor reduction was observed in mice treated with Alt-1-IgG conjugate compared to other groups.

Example 6

A composition according to the invention was produced against CA 19.9 (SLe$^a$), an excellent marker for pancreatic cancer (87%), gastric cancer (68%), and colo-rectal cancer (50%). It has been documented that the carbohydrate ligand (SLe$^a$) constitutes the carbohydrate moieties of the human carcinoembriogenic antigen family [Anostario, et al; 1994)], human pancreatic MUC-1 [Ho, et al; 1995)], and CA 19.9 [Hamanaka, et al; *Pancreas,* 13:160-165 (1996)]. SLe$^a$ has also been identified in human melanoma [Ravindranath, et al, *Cancer,* 79:1686 (1997)] and colorectal cancer [Yamada, et al (1997)]. Those skilled in the art will recognize that a composition containing a binding agent specific for SLe$^a$ (or one or more other adhesion molecules), such a composition optionally having one or more other binding agents specific for other antigens or molecules, may be useful in the treatment of many other cancers, since SLe$^a$ is expressed in large quantities on the surface of many other tumors [Srinivas, et al; (1996)].

The binding agent in the composition was Alt-3, an IgG3 monoclonal antibody that binds strongly to CA 19.9, and has been shown to mediate tumor killing through CDC in vitro.

Approximately $10^4$ chromium labeled SW 1116 (2200 CPM) were incubated with different concentrations of Alt-3, Alt-2, NS1116, Alt-4, and unspecific mIgG3 (20 µg/mL to 0.0025 µg/mL). The antibodies were incubated for 45 minutes at 4° C. In the treatment groups incubated with HAMA, the antibodies were washed twice with medium and incubated with 1 µg/mL of HAMA for 45 minutes at 4° C. All plates were washed and effector cells (fresh collected human PBLs) or fresh human serum (20% in medium) were added and incubated for four hours. The cytotoxic index (C.I.) was then calculated. Paired T test was used to analyze each concentration.

Figure 9:
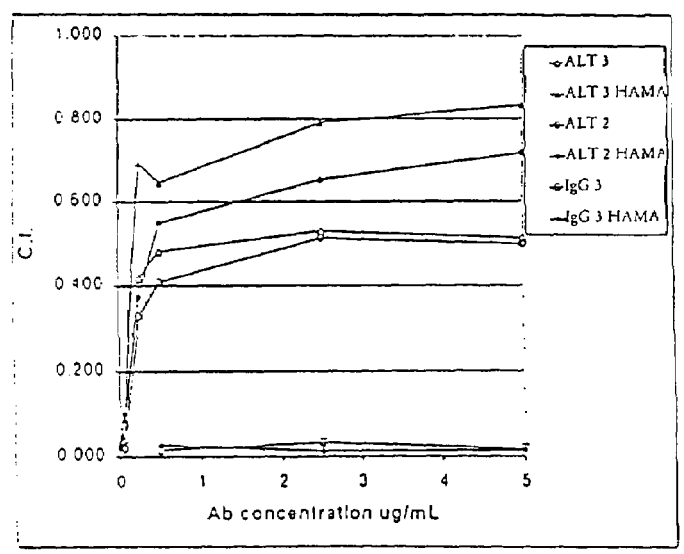
FIG. 9 shows that Alt-3 and Alt-2 binding agents are effective in complement-mediated cytotoxicity.
Figure 10:
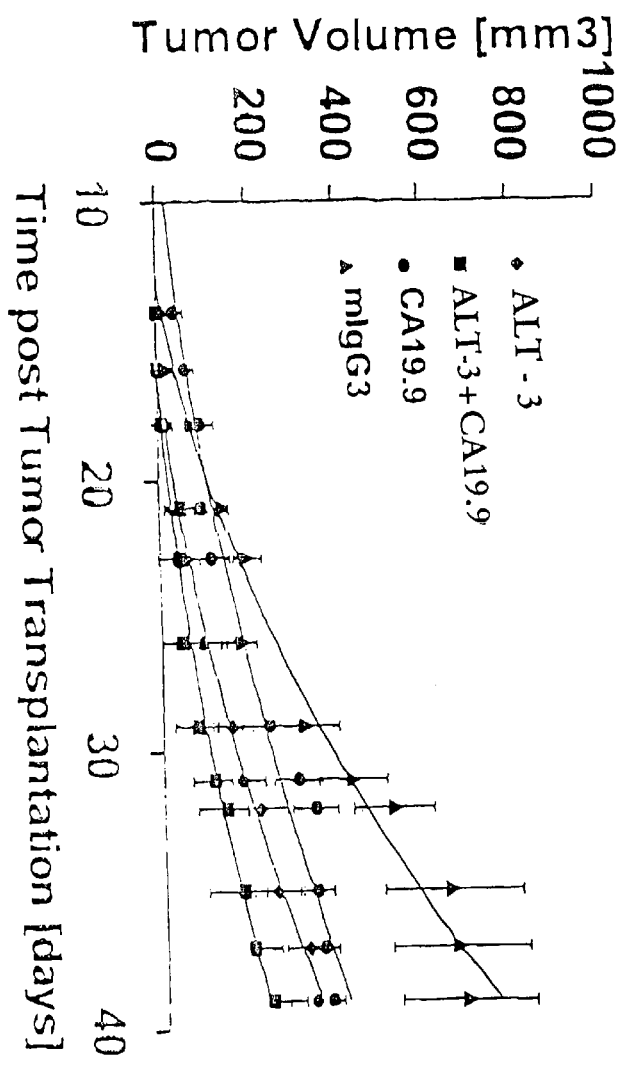
FIG. 10 shows the reduction in gastro-intestinal tumor volume after administration of a anti-CA19.9 antibody.

This experiment shows that Alt-3 and Alt-2 are extremely effective in complement-mediated cytotoxicity (FIG. 9). Such cytotoxicity is increased in the presence of HAMA. The anti-tumor effect of Alt-3 was also analyzed in SCID/BG mice reconstituted with human PBL. This experiment shows a reduction in tumor volume as a result of the binding agent and the binding agent/antigen complex. (FIG. 10).

Example 7

PSA Directed Immunotherapy of Prostate Cancer (Production of AR47.47)

Prostate specific antigen (PSA) represents an attractive target for the immunotherapy of prostate cancer. This glycoprotein is almost exclusively synthesized by the prostatic gland and is currently used for the diagnosis and monitoring of prostate cancer patients. However, since PSA is recognized as a self-antigen, it is essential for effective immunotherapy to develop innovative strategies capable of triggering the immune system and induce a protective immunity against PSA expressing cells. This example demonstrates the use of an antibody to elicit an anti-idiotype cascade associated with an antigen specific anti-tumor immune response. A large panel of anti-PSA monoclonal antibodies have been produced in our laboratory and these antibodies were evaluated for their potential therapeutic efficacy against prostate cancer. We have demonstrated that the immunization of mice with a selected anti-PSA antibody can induce a specific immunity against PSA itself. These results therefore emphasize the potential use of anti-PSA antibodies for the immunotherapy of prostate cancer.

Hybridoma clones secreting anti-PSA antibodies were produced by fusion of the murine myeloma cells Sp2/O with the splenocytes of a Balb/c mouse immunized with human PSA. An exemplary clone, AR47.47, binds to an epitope of PSA corresponding to amino acid sequences 139-163 of the PSA molecule.

The first criteria of selection used to identify the anti-PSA antibody was the ability of this antibody to interact with circulating PSA. Circulating PSA is found either in a free form or complexed to anti-proteases such as α-anti-chymotrypsin and α2-macroglobulin. To screen for clones we used three different forms of PSA: free PSA; PSA complexed to α-anti-chymotrypsin (PSA-ACT); and free PSA non complexing to α-anti-chymotrypsin (PSA-nc). Free PSA corresponds to PSA directly purified from human seminal fluid. Co-incubating free PSA with purified ACT results in the formation of PSA-ACT and PSA-nc. PSA-nc can be separated by gel filtration chromatography. It is believed that PSA-nc may represent the free form of PSA present in the circulation. Complexing of PSA with α2-macroglobulin results in the total encapsulation of PSA. As a consequence, this form of PSA is no longer detectable by monoclonal anti-PSA antibodies. We therefore did not use this form of circulating PSA for the screening.

PSA belongs to the kallikrein family and a high degree of structural homology is found between PSA and the kallikreins HK1 and HK2. The absence of cross reactivity of the anti-PSA antibody with kallikrein isolated from human plasma was used as second criteria for selection.

The hybridoma clone AR47.47 responded to the criteria described above, a strong immunoreactivity was observed with the three forms of PSA used for the screening whereas no cross reactivity was observed with human plasmatic kallikrein. The hybridoma clone AR47.47 was cloned twice by limiting dilution and the second generation clone AR47.47R6R6 was chosen for further studies. Clone AR47.47R6R6 was adapted to standard medium (RPMI 10% FBS) and a cell bank was formed. The absence of mycoplasma contamination was verified by using the Boehringer Manheim mycoplasma test. Clone AR47.47R6R6 has been deposited in the American Type Culture Collection, and has received Accession No. H-B 12526.

Immunization in DBA mice with a binding composition according to the invention (AR47.47) was examined for the induction of a specific PSA immunity via the idiotypic network (i.e. induction of Ab3 antibodies). Anti-PSA antibodies (Ab3) could be detected in the serum of animals immunized with AR 47.47, a minimum of two injections of AR 47.47 was required for Ab3 production. No reactivity towards PSA was detected for the control groups (mice immunized with an isotype matched control antibody not related to PSA and mice receiving PBS injections).

AR 47.47 is directed towards a PSA epitope comprised between the sequence 139-163 of the PSA molecule. The anti-PSA antibodies produced by AR 47.47 immunized mice can specifically interact with the PSA peptide 139-163, showing that at least part of the Ab3 produced are identical in term of specificity to AR 47.47. These results demonstrate that the immunization with AR 47.47 can induce a specific anti-PSA immunity in the host.

Example 8

Anti-Idiotypic Induction of PSA Immunity in Mice

Mice were used to determine whether immunization with anti-PSA antibodies can induce a specific immunity against PSA via activation of the idiotypic network. The goal of this experiment was to demonstrate that the immunization of mice with anti-PSA antibodies (Ab1) can stimulate the immune system to generate anti-idiotypic antibodies (Ab2=surrogate antigen), and anti- anti-idiotypic antibodies (Ab3) capable of reacting with the original antigen.

These experiments used a commercially available antibody as a model anti-PSA antibody (RLSD09; ATCC HB-8525). The purified antibody was conjugated to Keyhole Limpet Hemocyanin (KLH) to enhance its immunogenicity. The anti-PSA antibodies conjugated to KLH were still capable of binding to PSA, indicating that the idiotype of the antibodies were not masked by the conjugation procedure. B43.13 antibody, a mouse monoclonal antibody of the same isotype as the PSA antibody (IgG1) was used as the control. B43.13 antibody is specifically directed against the CA125 ovarian tumor antigen and does not cross react with PSA. In addition FACS analysis verified that the B43.13 antibody does not bind at the cell surface of Line-1-PSA or P81 5-PSA.

Mice were subdivided into three groups of five mice each. The first group of mice was immunized with anti-PSA antibody conjugated to KLH. The second group of mice was immunized with the control B43.13 antibody conjugated to KLH. The third group of mice received PBS injection. Injections were performed i.p. at 10 days intervals with complete Freund adjuvant for the first injection and incomplete Freund adjuvant for the second injection.

Ab2 is a surrogate antigen capable of mimicking the PSA epitope recognized by the injected anti-PSA antibody. A competitive inhibition assay was established to measure the serum level of Ab2. This assay was performed 5 days after the second injection. An inhibition was observed after incubation in the presence of mouse sera from mice immunized with anti-PSA antibody, but not when sera from mice immunized with control antibody or PBS were used. These results indicate that the Immunization of Balb/c mice and DBA mice with the anti-PSA antibody can induce the formation of anti-idiotypic antibody (Ab2) capable of mimicking PSA.

Example 9

Effect of Anti-PSA Immunization on Tumor Development

Balb/c mice were used to determine whether immunization with anti-PSA antibodies can protect the animals against a subsequent tumor challenge. Balb/c mice were divided into 3 groups of 5 mice each. The first group was immunized with anti-PSA antibody RLSDO9 conjugated to KLH, the second group was immunized with control antibody B43 conjugated with KLH, the third group received PBS injections. A total of 4 injections were given for each group using 50 µg of antibodies for each injection. The tumor cells Line-1-PSA were injected intravenously between the third and fourth injections. Nineteen days after tumor inoculation, the mice were sacrificed, the number of tumor foci in the lungs and Ab3 levels in the serum were determined.

The tumor burden in the group of mice immunized with anti-PSA MAb was considerably lower compared to the group of mice immunized with control antibody. Of particular interest is the demonstration, in the group of mice immunized with anti-PSA MAb, of a negative correlation between Ab3 levels and the number of tumor foci in the lungs.

Example 10

Anti-Inflammatory Composition

To test for the effectiveness of a composition containing a binding agent in treating inflammation, a double blind experiment was performed on 18 Spraque Dawley rats (weight about 450 g) divided into 3 groups (8 rats in each group).

The first group was vaccinated with KLH conjugated IgM antibody specific for a carbohydrate ligand on leukocytes (250 µg/rat, i.p.). The second group was vaccinated with KLH conjugated IgM antibody with no binding to the same ligand (250 µg/rat, i.p.). The third group was a control group, and received no vaccination.

Inflammation was induced by injecting 1% carrageenan in 0.9% NaCl (type IV), in the rat right hind paw (0.5 ml/rat). Observation of paw edema by water displacement measurement and caliper measurement.

Figure 11:
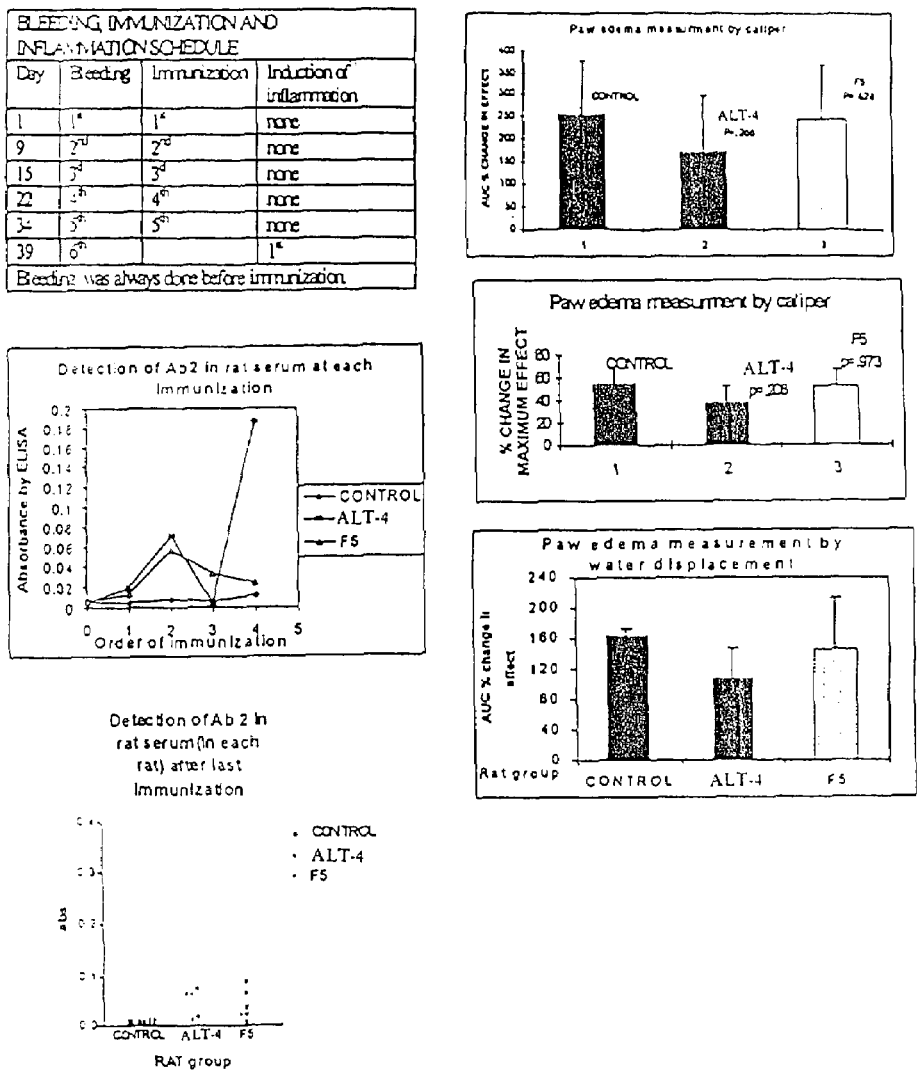
FIG. 11 shows the results and characteristics of an anti-inflammatory anti-CA19 antibody.

The inhibitory effect of Alt-4 antibody on inflammation was clinically different from the control group and control IgM antibody group (FIG. 11).

Example 11

Photoactivation Increases Immunogenicity

Normal, healthy, Sprague-Dawley rats were used. Animals were randomly grouped (4 per group) to receive four different doses (5 µg, 10 µg, 25 µg and 50 µg) of MAb 43.13. Pre-injection blood samples were drawn prior to initiation of the injection schedule. Each rat received the appropriate dose of MAb diluted in sterile 0.01 M phosphate buffered saline intravenously. A second study group received 20 µg of each MAb preparation with or without Incomplete Freund's Adjuvant (IFA). Blood samples were taken just prior to the dose injection at 0, 21, 42, 63 and 77 days.

MAb-B43.13 is a murine IgG, reactive with CA 125. Antibody preparations consisted of MAb-B43.13 in the native form or in a UV-exposed form (e.g., photoactivated). Native MAb was diluted from a stock concentration of 5 mg/mL with 0.01 M phosphate buffered saline to doses of 5, 10, 25 and 50 µg/100 µL. UV exposed MAb was reconstituted from the lyophilized form with 0.01 M phosphate buffered saline (2.2 mg/0.47 mL) and diluted to obtain the same doses as for the native MAb.

An assay was developed to measure the rat anti-mouse response in the serum of the injected animals. Anti-isotype rat anti-mouse antibodies were measured using an ELISA plate coated with an isotype matched control antibody, MOPC 21. Samples were diluted 1/100, allowed to react with the coated antibody, washed, and bound antibody detected using peroxidase conjugated goat anti-rat IgG (H+L) with ABTS substrate. Unknowns were read off a standard curve generated using a commercial rat anti-mouse antibody.

The results of the rat anti-mouse (RTAMA) analysis of sera from the various groups of rats injected with native and UV exposed MAb-B43.13 are shown in Tables 7 and Table 8. The immunological response to the preparations is expressed in terms of the number of responders in each group, with the numerical cut-off defined in the tables. This value (mean of all pre-injection samples (blanks)+3 S.D.) ensures that a true positive response is measured and the results are unlikely to be due to assay variation. The tabulation of responders is probably more meaningful given that the fluctuation of the magnitude of response can be very large and therefore, hinder interpretation.

TABLE 7

ANIMAL RESPONSE* TO INTRAVENOUS INJECTION OF NATIVE AND UV EXPOSED MAb-B43.13 PREPARATIONS

| Sampling | | Number of Responders | | | |
|---|---|---|---|---|---|
| Time | Preparation | 5 µg | 10 µg | 25 µg | 50 µg |
| Pre-injection (blank) | Native | NA** | NA | NA | NA |
| | UV exposed | NA | NA | NA | NA |
| Day 21 | Native | 0 | 0 | 0 | 0 |
| | UV exposed | 2 | 3 | 1 | 1 |
| Day 42 | Native | 0 | 1 | 0 | 1 |
| | UV exposed | 2 | 3 | 4 | 3 |
| Day 63 | Native | 1 | 3 | 3 | 3 |
| | UV exposed | 2 | 4 | 3 | 4 |
| Day 77 | Native | 2 | 2 | 2 | 1 |
| | UV exposed | 3 | 4 | 4 | 4 |

*Number of animals responding in a group o four (RTAMA values ≦ pre-injection sample mean + 3 S.D.)
**NA = Not Applicable The data tends to confirm that the response to the UV exposed MAb-B43.13 occurs earlier (after only one injection) as shown by the greater number of responders at all dose levels in the Day 21 groups.

Furthermore, at all other time periods (and after multiple injections), the proportional response of each group given intravenous UV exposed MAb-B43.13 is greater. It may be suggested that the response is sustained longer for UV exposed MAb-B43.13 since the native MAb-B43.13 appears to show a reduced response rate from Day 23 to Day 77. Actual values of increased response at day 77 are shown in Table 8.

TABLE 8

TOTAL AND $AB_2$ INDUCTION IN RATS INJECTED WITH NATIVE OR UV-EXPOSED MAB--B43.13

| | TOTAL IMMUNE RESPONSE (mean ± S-E) | $Ab_2$ RESPONSE (mean ± S-E) |
|---|---|---|
| Native Mab - B43.13 | 38.47 ± 2.99* | 18.77 ± 8.23 |
| UV-exposed Mab - B43.13 | 1608.67 ± 369.39* | 87.27 ± 45.11 | n = 3
*p = 0.0496

Example 12

Protein Modification as a Result of UV Exposure

The final chemical species present after photoactivation are specific for a given set of exposure conditions and the composition of the matrix solution (as described above). For simple polypeptides containing any of the three primary UV absorbing (UV-B) amino acids (cystine, tryptophan, tyrosine) the consequences of UV exposure can lead to amide bond cleavage, disulfide bond cleavage, alteration of absorbing amino acids and alteration of adjacent or close proximity amino acids. These changes are brought about by direct photoionization or photoexcitation and indirectly by radical formation from other constituents. The nature and extent of these modifications is highly dependent on the chemical reactivities of the species generated and other constituents reactive tendencies or stabilizing/quenching capabilities. For this size of molecule any alteration generally results in dramatic changes in biological function.

These same reactions can take place in larger proteins, however secondary and tertiary structural elements present differing substrates for UV exposure in spite of similar amino acid sequences. Therefore, the hydrophobic/hydrophilic nature and proximal amino acids from distant chain sequences as a result of folding alter the micro-environment and therefore influence the degree and nature of the modification, in addition to other constituents issues stated above. Given the predominance of the tryptophan absorption profile in this UV band width, it is thought to be the primary site of the initial photoactivation process, but direct action on cysteine and tyrosine are also viable.

The mechanism for indirect amino acid modifications has been proposed as local hydrated electron generation or direct energy transfer from the primary absorbing site. The primary observed changes for large proteins focus on measurable chemical/biochemical changes such as absorption and fluorescence determinations of aromatic amino acids which relate to global modifications. Individual amino acid alterations be detected in this group of proteins where sulfhydryl content can be determined as evidence of cysteine disulfide cleavage and/or where a critical amino acid for function is involved. For smaller proteins amino acid hydrolysis and complete quantitation can be performed. The primary concern for functional large proteins, such as enzymes, receptor, or antibodies, is therefore not specific amino acid modification but the consequences of any change on their biological function, and has invariably been described as loss of enzyme function, receptor recognition, or antigen binding.

Example 13

UV Exposed B43-13/CA125 Antibody/Antigen Complex Produces Better CA125 Specific Cellular Immune Response and Better Humoral Response Better cellular immune response was observed when the UV exposed antibody was presented in association with the antigen to T-cells. Thus, macrophages isolated from mouse peritoneal cavities were stimulated with native B43.13 or UV exposed B43.13 in association with CA125 and presented to CA125 specific mouse T-cells isolated from mice injected with CA125. Control experiments included stimulation of the macrophages without the antigen. When the proliferation of T-cells as monitored by [$^3$H]-thymidine uptake was followed, optimal stimulation index was observed in macrophages stimulated with UV exposed B43.13-CA125 complex. The results are summarized in Table 9 below.

TABLE 9

| STIMULATING AGENT[1] | STIMULATION INDEX[2] |
|---|---|
| CA125 | 2.76 |
| Native MAb - B43.13 | 3.98 |
| UV-exposed MAb - B43.13 | 3.31 |
| Native MAb - B43.13 - CA125 | 4.71 |
| UV-exposed MAb - B43.13 - CA125 | 5.28 |

[1]·1 μg/ml of the antibody and 100 Units/ml CA125 were used.
[2]·Mean of three individual experiments done in triplicate.

Example 14

UV Exposure Conditions for Enhanced Immunogenicity Studies

A typical experimental set-up consists of an eight lamp photoreactor unit (typically 200-400 nm spectra, 90% at 300+/−20 nm; 3-9 watts/lamp) arranged concentrically about an approximately 15 centimeter diameter cylinder with appropriate associated electronics, shielding, etc. In this photoreactor unit (RMR-600, Southern New England Ultraviolet Company), samples to be exposed are arranged in several configurations: (1) as individual 1.5 ml (borosilicate glass or quartz) vials tubes located on an eight unit carousel (approx. 5 cm diameter) which is rotated in the chamber at 1-5 rpm for 0-180 minutes (typically 30 minutes); (2) as 2 single vial/tubes (as above) placed in the center of the exposure source and exposed for similar time frames; or (3) as a helical glass (as above) coil (approx. 3 mm external diameter) which allows target solution to flow through the photoreactor unit for various time frames of approximately 0-180 minutes, but typically 10-20 minutes. This latter set-up allows considerable volumes of target solution to be exposed on a continuous basis for large-scale manufacturing purposes.

Under any of these exposure conditions, protein target solutions at 0.5-10 mg/ml (typically 5 mg/ml) in a variety of expected benign low molarity buffer solutions (typically phosphate, pyrophosphate, or tartrate; pH 5-10), can be exposed to determine their effects on target protein immunogenicity.

Example 15

Three derivatives of scFv with additional C-terminal extensions containing mouse and human tuftsin (pDL-6 and pDL-11), or a control sequence (pDL-10), were designed. To construct plasmids pDL-6, pDL-10, and pDL-11, DNA oligodeoxyribonucleotides (SEQ ID NOS.: 1-3)

(5'-GAATTCTGGAGGTGGTACCCAGCCTAGGTAGC-3',

5'-GAATTCAGCTGGAGGTGGTGGATGTGC-3', and

5'-GAATTCTGGAGGTGGTACCAAGCCTAGGTAGC-3')

coding for the amino acid sequences (SEQ ID NOS.: 4-6) N-SerGlyGlyGlyThrGlnProArg-C, N-SerAlaGlyGlyGlyGlyCysAla-C, and N-SerGlyGlyGlyThrLysProArg-C, were used by inserting fragments in EcoRI and EagI sites of pPIC-B43. The plasmid DNAs were transformed into competent GS115 cells by electroporation and the resulting transformants were selected on histidine-deficient media. All positive clones obtained were isolated, cultured in induction media, and analyzed for protein expression in SD S-PAGE followed by Commassie staining. The scFv-tuftsin proteins were produced in minimal media to simplify some downstream protein purification process.

In order to evaluate the anti-idiotypic response, six to 8-week-old BALB/c mice were immunized with 50 μg scFv-tuftsin subcutaneously (Day 0). Two weeks later the mice were received 25 μg of scFv-tuftsin intraperitonealy. The serum of mice was collected on Day 7, 14 and 21.

The anti-idiotypic antibody production was detected by enzyme-linked immunosorbent assay (ELISA). Briefly, chimeric B43.13 was coated to a solid surface and then blocked by 3% BSA/PBS. The chimeric B43.13 was incubated with serum samples for 1 h and then incubated with goat anti-mouse H+L-HRPO for another hour, followed by three washes with Tween 20/PBS. A color reaction was developed by adding 50 μl of substrate solution. Absorbence was read at 405 nm. The same procedure was applied to detect anti-anti-idiotypic antibody (Ab3) production except CA125 was coated to ELISA plate at the beginning.

The data shows that it is possible to detect both Ab2 and Ab3 in the serum samples and this indicates that scFv-tuftsin retained the idiotypic immunogenicity which could trigger humoral immune response in mice. We found that the mice immunized with scFv-tuftsin started to show strong anti-idiotypic antibody (Ab2) production after day 20 post the first immunization. However, the anti-anti-idiotypic antibody (Ab3) production appeared earlier, peaking around day 15. This indicates that the induction of an idiotypic network response might be an important part of the effector mechanism in MAb-based therapy.

Example 16

Construction and Characterization of Single Chain Antibody

The MAb B43.13 variable domain sequences were PCR-amplified using sequence specific primers, and engineered into a cloning vector with scFv orientation of V1-linker-Vh. The DNA fragment coding for the scFv was then sub-cloned into P. pastoris vector, pPIC-9 with aF secretion signals, resulting in recombinant plasmid pPIC-B43.13. One derivative of pPIC-B43.13 with additional C-terminal extensions containing one cysteine (pDL10) was designed to form a disulfide bridge. Therefore, the antigen binding activity can be enhanced by increase of avidity. To construct plasmids pDL10, DNA oligodeoxyribonucleotides (SEQ ID NO.: 7) (5'-GAATTCAGCTGGAGGTGGTGGATGTGC-3') coding for the amino acid sequences, (SEQ ID NO.:5) N-SerAla-GlyGlyGlyGlyCysAla-C were used by inserting fragments in EcoRI and EagI sites of pPIC-B43.13.

The plasmid DNAs were transformed into competent GS115 cells by electroporation and the resulting transformants were selected on histidine-deficient media. After screening for integration at the correct loci, (i.e. colonies can grow on a −his/+glycerol plate but grow slowly on a −his/+methanol plate), all positive clones obtained were isolated, cultured in induction media, and analyzed for protein expression in SDS-PAGE followed by Coomassie staining, as we described previously (Luo et al., 1997). The protein samples were dialysed against PBS and concentrated using Centricon® 10 filter (Amicon, Danvers, Mass.).

Purity of scFv-pDL10 were analyzed by SDS-PAGE under reducing condition. CA125-binding specificity was determined using a ELISA in which microtiter plate wells were coated with CA125, CA15.3 (a human breast cancer antigen), or CA19.9 (a human colon cancer antigen). The bound single chain antibody was detected by peroxidase-abeled goat ant-mouse H and L (Southern Bio. Associ.) For 1 hour at room temperature. Following three washes, 50 µl of ABTS substrate solution was added. The absorbance was measured at 405 nm.

Single chain Fv containing poly(lactic-co-glycolic acid) microspheres were prepared by a double-emulsion technique with some modifications (Uchida et al., 1994). $Na^{125}I$ labeled scFv-pDL10 was used as a tracer to determine the loading efficiency. Briefly, scFv-pDL10 (1.5 mg) and $Na^{125}I$-scFv-pDL10 (0.4 µg) in PBS was mixed with 500 µl of chloroform containing 100 mg PLGA 50/50 (Lactel). The mixture was sonicated for 15 s using a sonicator homogenizer (Heat System, New York). The resulting emulsion was added to 2 ml of 9% poly(vinyl alcohol) (PVA, Aldrich, USA). Emulsification was continued by sonicate on for 1 min. The emulsion was transferred to 8 ml of 9% PVA and stirred for 2 hours for evaporation of the chloroform. Microspheres were recovered by centrifugation (15 min, 15000 rpm) and have washed with distilled water and freeze dried for at least 24 hours.

BALB/c female mice 6-8 weeks of age were used in all in vivo experiments. The immunization groups included five groups: 1) immunized with PLGA microspheres, 2) immunized with scFv-pDL10, 3) immunized with scFv-pDL10 formulated in PLGA microspheres, and the other two groups immunized with the mixture of formulated scFv-pDL10 and GM-CSF or TNF-α. After collection of pre-immune serum samples, groups of 4 mice received two subcutaneous immunizations on day 0 and day 14, followed by two intraperitoneal immunizations on day 21 and day 28. The dose for immunization was 10 mg of the microspheres for s.c., 5 mg for i.p. For the other groups that received no microspheres, the dose of scFv-pDL10 matched the amount formulated. The cytokines were purchased from R & D Systems (USA) and were given to mice at a dose of 0.1 µg per day. Tail vein blood samples were taken periodically into Microtainer tubes (Becton Dickinson, USA) and frozen at −80° C. until assay.

Example 17

Dose

Those with skill in the art recognize that the administered dosage can vary widely based on a wide set of different circumstances. The following provides preliminary dosage guidelines.

Retrospective analysis of more than 100 patients who have been injected up to ten times with a 2 mg dose of MAb-B43.13 indicated that some of these patients experienced: a) an unusual course of their disease, characterized by unexpectedly long survival times; and b) no significant adverse reaction or toxicity.

Immunological studies were conducted to understand and evaluate the in vivo mechanism of action of MAb-B43.13. These studies indicated that the extent of anti-idiotypic induction in patients injected with a 2 mg dose of MAb-B43.13 was unrelated to the number of injections or the clinical stage of their disease. However, anti-idiotypic induction is dependent on the levels of the circulating CA 125 present in the patient's sera. Additional experiments demonstrated that the injection of MAb-B43.13 into patients with measurable serum CA 125 led to the formation of antigen-antibody complexes, resulting in antigen epitope presentation and antigen-specific humoral and cellular response to the tumor.

These studies indicate that an effective dose requires only enough antibody to optimally deliver and present all possible circulating CA 125 antigen to the immune system. In vitro studies indicated that 1 ng of MAb-B43.13 can bind 10 units of CA 125. Assuming 40 mL of plasma per kg of body weight, the injection of 2 mg of MAb-B43.13 into a 60 kg patient can bind approximately 8333 U/mL of CA 125 in serum. Since all of the ovarian cancer patients tested to date have had far less than 8333 U/mL of CA 125 in their serum, an injection of 2 mg of MAb-B43.13 is more than sufficient to induce the required immune response. CA 125 levels were considered as significantly elevated when the CA 125 concentration is above three times the cut-off level (e.g., 3×35 U/ml, or 105 U/ml). Additionally, in patients that received radiolabeled MAB-B43.13 for immunoscintographic confirmation of the disease, the results of imaging were excellent in spite of high serum CA 125, suggesting that there is excess MAB-B43.13 for specific tumor uptake.

Furthermore, multiple injections at selected intervals appear to provide optimal benefits to patients, since CA 125 is generated throughout the course of the disease.

Finally, the retrospective analysis showed that the 2 mg dose appears to have therapeutic efficacy; none of the patients (>100) have developed any serious side effects or adverse reactions. If the total HAMA response is an indication of anti-idiotypic induction, a 2 mg dose generates significant levels of anti-idiotypic antibodies to produce the desired therapeutic benefit. Multiple injections of 2 mg of MAb-B43.13 at selected intervals appears to maintain the anti-idiotypic antibodies at the desired therapeutic level without causing any isotypic HAMA-induced toxicity.

A range of effective doses or a therapeutically acceptable amount of MAb-B43.13 therefore includes, but is not limited to, a total dose of about 2 mg or less.

Example 18

Immunophotodynamic Therapy

An immune competent mouse model is available for the MUC-1 system. The MUC-1 transfectant 413 BCR forms tumors (subcutaneous or intravenous) in BALB/c or CB6F1 mice. The BALB/c animal model was used to test HBBA-R2-SL, HBBA-R2 SIL with Alt-1 and a control antibody (HBBA-R2 is a hypocrellin B derivative described in PCT/US98/00235, incorporated herein by reference; SL=stealth liposome; SIL=stealth immunoliposome). The model has the advantage that the bystander effect of the immune system can be analyzed. Help from the immune system, especially from macrophages, has been reported to augment the immune system for the outcome of PDT and as necessary for obtaining complete response rates. BALB/c mice were injected with $2-2.5 \times 10^6$ 413BCR cells into the right flank (s.c.).

Tumors appeared after 7-10 days. When tumors reached a diameter of about 5 mm, hypocrellin formulations were injected iv. at 1 mg/kg. Two hours post injection of HBBA-R2, light treatment was performed at 40 J/cm² (>600 nm). Mice were followed by measuring tumor size. When tumor size reached 4-times pre-treatment volume, mice were sacrificed. Tumors were followed for 2 months and survival curves were calculated, plotted and compared to the light-only treatment group.

For stealth immunoliposome compositions, the antibody Alt-1, which binds to 413BCR cells, was used. Tumors were measured every second day in three dimensions. When tumors reached 4 times pre-treatment volume, mice were sacrificed. Mice treated with light only or drug only were used as control.

Immunoliposomes with Alt-1 showed complete cure in the presence of light. The HBBA-R2-SIL [Alt-1] also showed improved survival in the dark, compared to mice treated with light only. These results suggest a therapeutic effect of Alt-1 in this model and underline the importance of combined therapy using PDT and antibody vaccine.

For all formulations tested, immunoliposomes specific for the tumor showed the best therapeutic effect. This was also reflected when tumor volumes were used for comparison. The reason for the enormous differences between SL and SIL is not yet completely understood. The data suggest that immunoliposomes might cause an immune response in BALB/c mice that can help killing the tumor. From the biodistribution data we know that HBBA-R2 uptake at the tumor is slightly higher with SIL compared to SL.

Example 19

The murine monoclonal antibody Alt-4 is a candidate for the development of an anti-gastrointestinal cancer compound. MAb-Alt-4 binds to tumor antigen CA19.9, a Sialyl Lewis$^a$ antigen which is now generally recognized as one of the most important tumor-associated markers for gastrointestinal cancer. An approach of chimerization of antibody is to construct mouse-human antibody, which is composed hix of mouse variable region and human constant region, by using recombinant DNA technology. Most reports demonstrate the chimeric antibody is able to retain the same specific binding activity to the antigen as its parental mouse antibody, but avoid the human anti-mouse antibody (HAMA) response with in vivo applications.

Experimental Strategies:

cDNA isolation of V-genes: RT-PCR experiments were carried out to isolate antibody variable genes using specific primers. The cDNAs were then cloned into cloning vector pBluscript for DNA sequencing.

Chimeric Antibody Construction: chimeric clones of PAH-18.4H8PCRII#8 and PAG-18.4L20PCRII#19 was obtained by ligating PAG4622-18.4LPCRII and PAH46.6-18.4HPCRII as expression vectors and inserts were obtained from PBKS-18.4L20PCRI1 #14 and PBKS-18.4HPCRII #19. Chimeric clones were used for transfection of SP2/0 cells. To obtain the most efficient method for co-transfection of these cells control plasmid pSV-β gal DNA was used as a positive control plasmid to obtain the optimal conditions for transfection into cells.

Transfection: both methods of transfection showed successful transfection efficiency. Lipofectamine causes some cell death but most cells (80%) of cells that stay alive are transfected. In electroporations method cells transfection efficiency was high and cells that were transfected were growing into colonies which contained the new control plasmid. After establishing optimal conditions for transfection of SP2/0 cells co-transfection of SP2/0 cells with PAH-18.4 and PAG-18.4 was done.

Lipofectamine method: 2 ug of each DNA plasmid was used. The same protocol was mentioned above was followed. 24 hours after transfection, cells were harvested from 6-well plates and cells were seeded in 96-well plates with cell density of $1.0 \times 10^4$ cells/well. After overnight incubation at 37° C., selection media was added to each well in 1:1 ratio. Selection media includes 1 μg/μl of mycophenolic acid and 5 mM histodinal, 7.5 PH which was adjusted using NaOH. Selection media was changed every 3 days and cells were in selection media for 12 days Electroporation method: 20 μg of each DNA plasmid was used. The same method as mentioned above was used for transfection. Cells were plated into 96-well plates after electroporation. with $1 \times 10^4$ cells/well density. 24 hours after transfection selection media was added to cells. Cells were kept under selection media for 12 days and media was changed every 3 days.

To determine whether transfection has occurred supernatant of transfected cells were used for ELISA to assay the production of desired chimeric protein. CA19.9 was used to coat the plates and they were blocked by 3% BSA. For primary antibody tissue culture supernatant was used and for secondary antibody rabbit anti human (Fab'2) IgG (H+L) was used. Assay from ELISA gave positive results for production of desired product.

Example 20

Experimental Verification of the Generation of Antibody Response Against Multiple Epitopes Present in an Antigen by Injecting an Antibody Against a Single Epitope Cancer antigen CA125, which is expressed on more than 80% of epithelial ovarian cancers, is used as an example to demonstrate the present invention.

CA125 has multiple epitopes recognized by different antibodies such as OC125, M11, B43.13, B27.1, among others. In the present invention, MAb-B43.13 was used to generate a CA125 specific immune response which included recognition of the B27.1 epitope.

Method: 86 ovarian cancer patients with active disease were tested for the presence of antibodies against CA125.

None of the patients had antibodies against CA125 before injection of MAb-B43.13. The patients were injected with 2 mg of MAb-B43.13 at varying time intervals (e.g., see Table 5 for some of the patients). Sera from these patients were analyzed for the presence of human anti-CA125 antibodies by their ability to bind to the CA125 [R. Madiyalakan et al, *Hybridoma*, 14:199-203 1995)]. Such anti-CA125 antibodies were further classified to be against the B43.13 epitope or B27.1 epitope by their ability to inhibit the corresponding antibodies. The rationale for the classification comes from the fact that anti-CA125 antibodies in these patients would have been generated by either of the following two pathways:

1) If the anti-CA125 antibodies were generated in the manner suggested by the network theory noted above, the pathway would follow Ab1→Ab2→Ab3. Following this scheme, MAb-B43.13 (Ab1) would generate an anti-idiotype against MAb-B43.13 (Ab2), which would in turn generate an anti-anti-idiotype against MAb-B43.13 (Ab3; or anti-CA125 antibody). Furthermore, the Ab3 antibodies generated under this pathway would bind and be inhibited only by MAb-B43.13, because the B43.13 epitope is the only epitope present.

2) If the anti-CA125 antibodies were generated in a manner suggested by the present invention, the pathway would follow Ab1+soluble antigen→Ab3'. Following this scheme, MAb-B43.13 (Ab1) would bind the CA125 serum antigen, which would in turn generate an anti-CA125 antibody (Ab3'). Furthermore, the Ab3' antibodies generated under this pathway would bind and be inhibited by B27.1 antibodies, because, as noted above, CA125 is multi-epitopic and B43.13 and B27.1 epitopes are distinct; also, Ab3' will not bind to anti-MAb-B43.13 antibodies.

Thus, if the patients serum contained anti-CA125 antibodies that were inhibitable by MAb-43.13 only, it was classified as containing Ab3; those inhibitable by MAb-B27.1 were classified as Ab3'.

Results

Fourteen patients developed anti-CA125 antibodies in their sera (Table 1) in response to MAb-B43.13 injection. 10 of these 14 patients had Ab3' while only two patients had Ab3 antibodies in their sera. Two patients also had both the antibodies. The presence of Ab3 in their sera was also confirmed by the ability of these antibodies to bind to the purified rabbit anti-MAb-B43.13 antibody. There were two patients (#2 and #7) who had anti-CA125 antibodies, but were not inhibitable by MAb-B43.13 or MAb B27.1, thereby suggesting that they may have antibodies against CA125, which recognizes epitopes other than B43.13 or B27.1.

These results clearly indicate that when an antibody against a single epitope (B43.13) was injected into a patient an antibody response against the whole antigen is generated which recognizes different epitopes present in the antigen. The presence of Ab3 in some patients could be explained by the likely presence of excess B43.13 epitope in the CA125 due to insufficient binding of the antibody to that epitope or idiotype induction through Pathway I. Nevertheless, the predominant mechanism of the response seems to be through Pathway II. In other words, injecting a monoclonal antibody to a soluble multi-epitopic antigen into a patient having a functioning immune system generates an antibody to the antigen, where the generated antibody is inhibited by antibodies to different epitopes.

Example 21

In pharmaceutical studies, blood samples were analyzed for CA125 levels before and at selected intervals after MAb-B43.13 injection. In patients with elevated CA125 levels before injection, a significant drop in circulating CA125 levels could be seen immediately after MAb-B43.13 injection (Table 10). This clearly demonstrated that the binding agent upon introduction into the body interacts and removes the circulating CA125.

TABLE 10

| Time (min) after MAb | CA125 Clearance after MAb-B43.13 Injection Patient # (CA 125 levels are given in U/mL) | | | | | | |
|---|---|---|---|---|---|---|---|
| | 002 | 003 | 004 | 006 | 007 | 008 | 010 |
| 0 | 760 | 68 | 65 | 72 | 90 | 269 | 431 |
| 30 | 210 | 2 | 7 | 21 | 16 | 47 | 141 |
| 60 | 144 | 3 | 0 | 22 | 16 | 60 | 79 |
| 240 | 240 | 0 | 0 | 11 | 15 | 52 | 97 |
| 1440 | 277 | 5 | 3 | 6 | 23 | 59 | 96 |
| 2880 | 404 | — | 5 | 1 | 23 | 67 | 93 |
| 4320 | 429 | — | 7 | — | — | — | — |

Furthermore, antigen complexed with antibody is presented efficiently to the immune system and generates better antigen-specific humoral and cellular response. This was demonstrated by the following experiments shown in Examples 22 and 23.

Example 22

Balb/c mice were immunized either with 10 µg of MAb-B43.13 in PBS, i.v.; 10,000 units of CA125 in PBS, i.v.; or 10 µg of MAb-B43.13 and 10,000 units of CA125 in PBS, i.v., every three weeks for a total of 3 injections. The ratio in the B43.13/CA125 injection was similar to that observed in patients with elevated CA125 levels as determined based on the pharmacokinetics data given in Table 10. When the mice sera were analyzed for anti-CA125 antibody levels, the mice injected with the antigen-antibody complex had the highest titre. This supports the observation that binding agent—antigen interaction leads to better antigen specific humoral immune response compared to binding agent or antigen alone.

Example 23

Figure 2:
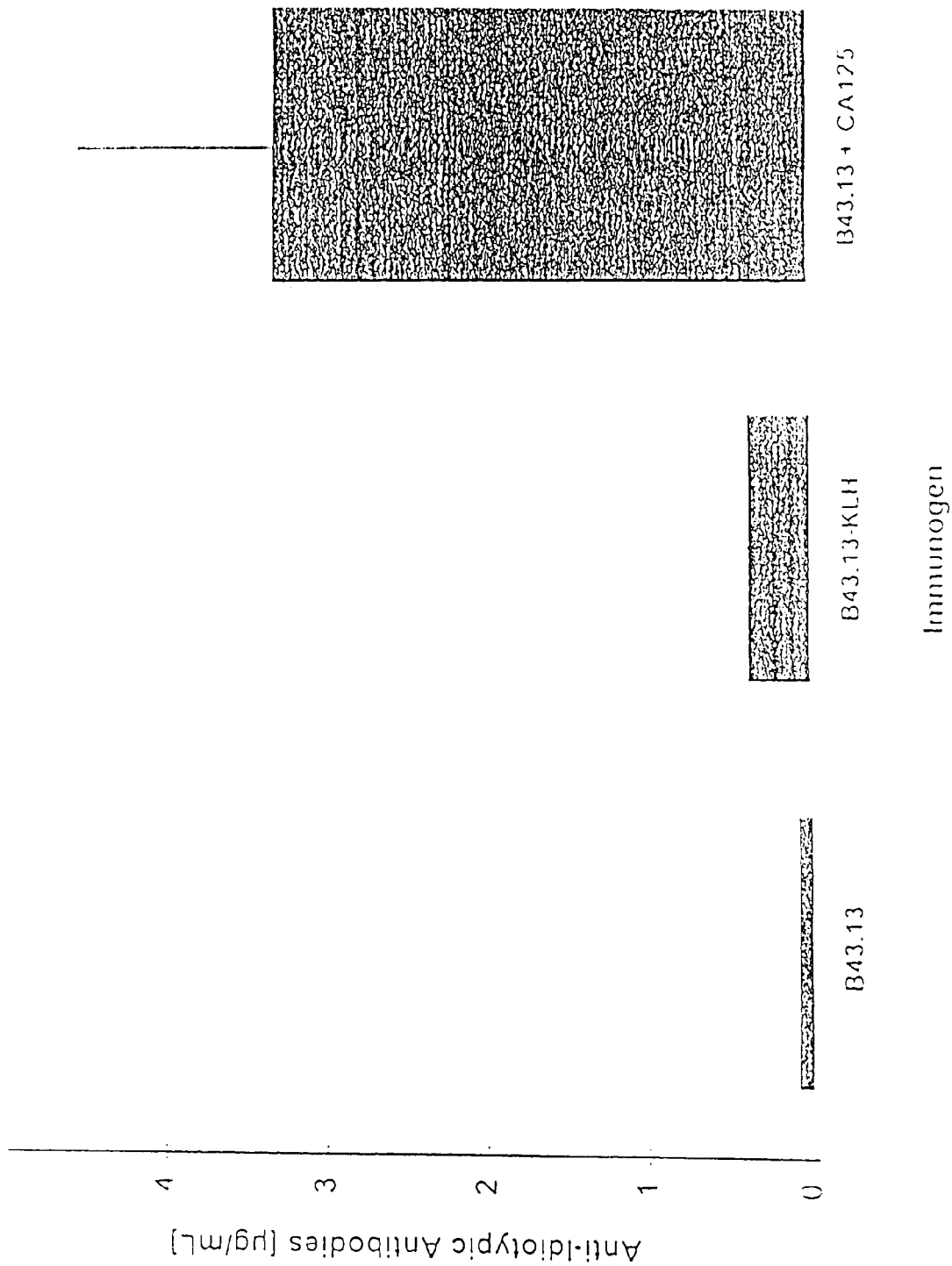
FIG. 2 shows the production of Ab2 in response to the administration of a composition of the invention.

Similarly, better cellular immune response was observed when the binding agent was presented in association with the antigen to the T-cells. Thus, macrophages isolated from mouse peritoneal cavities were stimulated with MAb-B43.13 alone; CA125 alone, a MAb-B43.13-CA125 complex; or control MAb-CA125 and presented to CA125 specific mouse T-cells (isolated from mice injected with CA125). When the proliferation of T-cells as monitored by [$^3$H]-thymidine uptake was followed, optimal stimulation index was observed in macrophages stimulated with antibody-antigen complex (FIG. 2).

Example 24

The role of serum antigen in inducing multi-epitopic antibody response as a consequence of an antibody injection was further confirmed in rabbit studies. Rabbits that do not contain any serum CA125, when injected with MAb B43.13, produced anti-CA125 antibodies that were not inhibitable by B27.1. In contrast, ovarian cancer patients with high serum antigen CA125 levels produce anti-CA125 antibodies that are inhibitable by B27.1 in response to MAb-B43.13 injection.

Example 25

Experimental Verification of Induction of Antigen Specific Anti-Tumor Response by Antibody Injection Human anti-CA125 antibody causes tumor cell lysis through antibody dependent cellular cytotoxicity ("ADCC"). Although the injected MAb-B43.13 does not cause by itself an ADCC and/or complement dependent cytolysis ("CDC") mediated lysis of ovarian tumor cells, the generation of anti-CA125 antibodies in patients injected with MAb-B43.13, leads to tumor cell lysis (see FIG. 3). This was studied in a $^{51}$Chromium release assay by incubating the labeled ovarian tumor cells with effector cells, and sera of six patients injected with MAb-B43.13. This supports the conclusion that the injection of a binding agent leads to its interaction with the antigen, with a specific humoral response resulting in anti-CA125 antibodies that cause tumor cell lysis through ADCC. The results clearly demonstrated the generation of antigen specific anti-tumor response after injection of the antibody.

Example 26

Tumor killing either through an anti-CA125 antibody-mediated ADCC mechanism or through CA125-specific CLTs, lead to increased survival in patients injected with MAb-B43.13. Although high levels of serum CA125 have been suggested to be a poor prognostic indicator, they seem to have a beneficial effect in combination with the injection of anti-CA125 antibody in such patients. For example, when the CA125 levels were more than 100 units/mL, immune response against CA125 increased by more than 20% which in turn increased the median survival in those patients from 39.1 months to 54.5 months (Table 11). Thus the injection of a binding agent to a patient containing elevated levels of multiepitopic soluble antigen leads to antigen specific humoral and cellular response which in turn leads to tumor killing followed by improved survival.

TABLE 11

Correlation between Serum CA125 Levels, Human Anti-CA125 (Ab$_1$') Response and Survival in Patients Injected with MAb-B43.13

| Preinjection Serum CA125 Level | %-age of Patients with Human Anti-CA125 Response | Mean Survival in Month |
|---|---|---|
| <100 U/mL | 10.3% | 39.1 |
| >100 U/mL | 32.6% | 54.5 |

Example 27

One pancreatic cancer patient diagnosed with metastatic disease was repeatedly injected with a composition including an anti-CA 19.9 antibody. The patient received no other treatment, and survived for 22 months after the original diagnosis (19 months after surgery and the injection) This is compared to the current survival period estimate of six months survival after initial diagnosis.

While the present invention has been described in some detail by way of illustration and example, it should be understood that the invention is susceptible to various modifications and alternative forms, and is not restricted to the specific embodiments set forth. It should be understood that these specific embodiments are not intended to limit the invention, and the intention is to cover all modifications, equivalents, and alternatives falling within the spirit and scope of the invention.

We claim:

1. A method for inducing a therapeutic host immune response against a multi-epitopic in vivo antigen that does not elicit an effective host immune response, the method comprising: contacting in vivo a multi-epitopic antigen selected from the group consisting of CA 125, CA 19.9, CA 15.3 and PSA present in a host's serum with a composition comprising a non-radiolabeled antibody or antigen binding fragment thereof that specifically binds to a first epitope on the multi-epitopic in vivo antigen, whereby the antibody or antigen binding fragment thereof forms an immune complex with the antigen, and whereby an effective host T cell response against the antigen in the immune complex is elicited.

2. A method for inducing a therapeutic host immune response against a multi-epitopic in vivo antigen that does not elicit an effective host immune response, the method comprising: contacting in vivo a multi-epitopic antigen selected from the group consisting of CA 125, CA 19.9, CA 15.3 and PSA present in a host's serum with a composition comprising a non-radiolabeled antibody or antigen binding fragment thereof that specifically binds to an epitope on the multi-epitopic in vivo antigen, whereby the antibody or antigen binding fragment thereof forms an immune complex with the antigen, and whereby an effective host humoral immune response against a second epitope of the multi-epitopic in vivo antigen is elicited.

3. A method for inducing a therapeutic host immune response against a multi-epitopic in vivo antigen that does not elicit an effective host immune response, the method comprising: contacting in vivo a multi-epitopic antigen selected from the group consisting of CA 125, CA 19.9, CA 15.3 and PSA present in a host's serum with a composition comprising a non-radiolabeled antibody or antigen binding fragment thereof that specifically binds to an epitope on the multi-epitopic in vivo antigen, whereby the antibody or antigen binding fragment thereof forms an immune complex with the antigen, and whereby an effective host T cell response against the antigen in the immune complex and an effective humoral immune response against a second epitope of the multi-epitopic in vivo antigen is elicited.

4. The method of claim 1, wherein the antigen is CA 125.

5. The method of claim 4, wherein the antigen CA 125 is present in the host's serum at levels greater than 100 U/ml.

6. The method of claim 4, wherein the host has ovarian cancer.

7. The method of claim 4, wherein the antibody is B43.13 which is producible by a hybridoma having ATCC deposit number PTA-1883, or an antigen binding fragment of said antibody.

8. The method of claim 1, wherein the antigen is CA 19.9.

9. The method of claim 8, wherein the host has gastrointestinal cancer.

10. The method of claim 8, wherein the host suffers from inflammation.

11. The method of claim 8, wherein the antibody is Alt-3 which is producible by a hybridoma having ATCC deposit number PTA-2691, or an antigen binding fragment of said antibody.

12. The method of claim 8, wherein the antibody is Alt-4 which is producible by a hybridoma having ATCC deposit number PTA-2692, or an antigen binding fragment of said antibody.

13. The method of claim 1, wherein the antigen is CA 15.3.

14. The method of claim 13, wherein the host has breast cancer.

15. The method of claim 1, wherein the antigen is PSA.

16. The method of claim 15, wherein the host has prostate cancer.

17. The method of claim 15, wherein the antibody is AR47.47 which is producible by a hybridoma having ATCC deposit number HB-12526, or an antigen binding fragment of said antibody.

18. The method of claim 1, wherein the antibody or antigen binding fragment thereof is present in the composition in an amount of from 0.1 µg to 200 µg per kg of body weight of the host.

19. The method of claim 1, wherein the antibody or antigen binding fragment thereof is formulated for administration to the host at a dose of about 2 mg per host.

20. The method according to claim 1, wherein the antibody or antigen binding fragment thereof is selected from the group consisting of a chimeric monoclonal antibody, a genetically engineered antibody, a Fab fragment, a F(ab')2 fragment, a single chain antibody, and a single chain antibody fragment.

21. The method of claim 1, wherein the composition comprises one or more adjuvants, one or more carriers, one or more excipients, one or more stabilizers, one or more pharmaceutically acceptable carriers and/or physiologically acceptable saline.

22. The method of claim 1, wherein contacting comprises administering by intravenous, subcutaneous, intraperitoneal, intradermal, intramuscular, or intralymphatic routes.

23. The method of claim 1, wherein contacting comprises administering the composition in solution, tablet, or aerosol form.

24. The method of claim 2, wherein the antigen is CA 125.

25. The method of claim 24, wherein the antigen CA 125 is present in the host's serum at levels greater than 100 U/ml.

26. The method of claim 24, wherein the host has ovarian cancer.

27. The method of claim 24, wherein the antibody is B43.13 which is producible by a hybridoma having ATCC deposit number PTA-1883, or an antigen binding fragment of said antibody.

28. The method of claim 2, wherein the antigen is CA 19.9.

29. The method of claim 28, wherein the host has gastrointestinal cancer.

30. The method of claim 28, wherein the host suffers from inflammation.

31. The method of claim 28, wherein the antibody is Alt-3 which is producible by a hybridoma having ATCC deposit number PTA-2691, or an antigen binding fragment of said antibody.

32. The method of claim 28, wherein the antibody is Alt-4 which is producible by a hybridoma having ATCC deposit number PTA-2692, or an antigen binding fragment of said antibody.

33. The method of claim 2, wherein the antigen is CA 15.3.

34. The method of claim 33, wherein the host has breast cancer.

35. The method of claim 2, wherein the antigen is PSA.

36. The method of claim 35, wherein the host has prostate cancer.

37. The method of claim 35, wherein the antibody is AR47.47 which is producible by a hybridoma having ATCC deposit number HB-12526, or an antigen binding fragment of said antibody.

38. The method of claim 2, wherein the antibody or antigen binding fragment thereof is present in the composition in an amount of from 0.1 µg to 200 µg per kg of body weight of the host.

39. The method of claim 2, wherein the antibody or antigen binding fragment thereof is formulated for administration to the host at a dose of about 2 mg per host.

40. The method according to claim 2, wherein the antibody or antigen binding fragment thereof is selected from the group consisting of a chimeric monoclonal antibody, a genetically engineered antibody, a Fab fragment, a F(ab')2 fragment, a single chain antibody, and a single chain antibody fragment.

41. The method of claim 2, wherein the composition comprises one or more adjuvants, one or more carriers, one or more excipients, one or more stabilizers, one or more pharmaceutically acceptable carriers and/or physiologically acceptable saline.

42. The method of claim 2, wherein contacting comprises administering by intravenous, subcutaneous, intraperitoneal, intradermal, intramuscular, or intralymphatic routes.

43. The method of claim 2, wherein contacting comprises administering the composition in solution, tablet, or aerosol form.

44. The method of claim 3, wherein the antigen is CA 125.

45. The method of claim 44, wherein the antigen CA 125 is present in the host's serum at levels greater than 100 U/mi.

46. The method of claim 44, wherein the host has ovarian cancer.

47. The method of claim 42, wherein the antibody is B43.13 which is producible by a hybridoma having ATCC deposit number PTA-1883, or an antigen binding fragment of said antibody.

48. The method of claim 3, wherein the antigen is CA 19.9.

49. The method of claim 48, wherein the host has gastrointestinal cancer.

50. The method of claim 48, wherein the host suffers from inflammation.

51. The method of claim 48, wherein the antibody is Alt-3 which is producible by a hybridoma having ATCC deposit number PTA-2691, or an antigen binding fragment of said antibody.

52. The method of claim 48, wherein the antibody is Alt-4 which is producible by a hybridoma having ATCC deposit number PTA-2692, or an antigen binding fragment of said antibody.

53. The method of claim 3, wherein the antigen is CA 15.3.

54. The method of claim 53, wherein the host has breast cancer.

55. The method of claim 3, wherein the antigen is PSA.

56. The method of claim 55, wherein the host has prostate cancer.

57. The method of claim 55, wherein the antibody is AR47.47 which is producible by a hybridoma having ATCC deposit number HB-12526, or an antigen binding fragment of said antibody.

58. The method of claim 3, wherein the antibody or antigen binding fragment thereof is present in the composition in an amount of from 0.1 μg to 200 μg per kg of body weight of the host.

59. The method of claim 3, wherein the antibody or antigen binding fragment thereof is formulated for administration to the host at a dose of about 2 mg per host.

60. The method according to claim 3, wherein the antibody or antigen binding fragment thereof is selected from the group consisting of a chimeric monoclonal antibody, a genetically engineered antibody, a Fab fragment, a F(ab')$_2$ fragment, a single chain antibody, and a single chain antibody fragment.

61. The method of claim 3, wherein the composition comprises one or more adjuvants, one or more carriers, one or more excipients, one or more stabilizers, one or more pharmaceutically acceptable carriers and/or physiologically acceptable saline.

62. The method of claim 3, wherein contacting comprises administering by intravenous, subcutaneous, intraperitoneal, intradermal, intramuscular, or intralymphatic routes.

63. The method of claim 3, wherein contacting comprises administering the composition in solution, tablet, or aerosol form.

64. The method of claim 1, wherein said non-radiolabeled antibody or antigen binding fragment thereof comprises an Fc portion that binds an FcγRII receptor.

65. The method of claim 1, wherein the antibody is an IgG1 antibody or an antigen-binding fragment thereof.

66. The method of claim 3, wherein said non-radiolabeled antibody or antigen binding fragment thereof comprises an Fc portion that binds an FcγRII receptor.

67. The method of claim 3, wherein the antibody is an IgG1 antibody or an antigen-binding fragment thereof.

68. The method of claim 1, wherein the multi-epitopic in vivo antigen is CA 125, and the first epitope on the multi-epitopic in vivo antigen is the epitope bound by an antibody produced by the hybridoma having ATCC deposit number PTA-1883.

69. The method of claim 2, wherein the multi-epitopic in vivo antigen is CA 125, and the epitope on the multi-epitopic in vivo antigen is the epitope bound by an antibody produced by the hybridoma having ATCC deposit number PTA-1883.

70. The method of claim 3, wherein the multi-epitopic in vivo antigen is CA 125, and the epitope on the multi-epitopic in vivo antigen is the epitope bound by an antibody produced by the hybridoma having ATCC deposit number PTA-1883.

71. The method of claim 1, wherein the antibody or antigen binding fragment thereof is specific for a single epitope.

72. The method of claim 71, wherein the antibody or antigen binding fragment thereof is selected from the group consisting of a chimeric monoclonal antibody, a genetically engineered antibody, a Fab fragment, a F(ab')$_2$ fragment, a single chain antibody, and a single chain antibody fragment.

73. The method of claim 2, wherein the antibody or antigen binding fragment thereof is specific for a single epitope.

74. The method of claim 73, wherein the antibody or antigen binding fragment thereof is selected from the group consisting of a chimeric monoclonal antibody, a genetically engineered antibody, a Fab fragment, a F(ab')$_2$ fragment, a single chain antibody, and a single chain antibody fragment.

75. The method of claim 3, wherein the antibody or antigen binding fragment thereof is specific for a single epitope.

76. The method of claim 75, wherein the antibody or antigen binding fragment thereof is selected from the group consisting of a chimeric monoclonal antibody, a genetically engineered antibody, a Fab fragment, a F(ab')$_2$ fragment, a single chain antibody, and a single chain antibody fragment.

\* \* \* \* \*

SEQUENCE LISTING

```
<160> NUMBER OF SEQ ID NOS: 7

<210> SEQ ID NO 1
<211> LENGTH: 32
<212> TYPE: DNA
<213> ORGANISM: Artificial Sequence
<220> FEATURE:
<223> OTHER INFORMATION: Primer

<400> SEQUENCE: 1
gaattctgga ggtggtaccc agcctaggta gc                                     32

<210> SEQ ID NO 2
<211> LENGTH: 27
<212> TYPE: DNA
<213> ORGANISM: Artificial Sequence
<220> FEATURE:
<223> OTHER INFORMATION: Primer

<400> SEQUENCE: 2
gaattcagct ggaggtggtg gatgtgc                                           27
```

-continued

```
<210> SEQ ID NO 3
<211> LENGTH: 32
<212> TYPE: DNA
<213> ORGANISM: Artificial Sequence
<220> FEATURE:
<223> OTHER INFORMATION: Primer

<400> SEQUENCE: 3
gaattctgga ggtggtacca agcctaggta gc                                      32

<210> SEQ ID NO 4
<211> LENGTH: 8
<212> TYPE: PRT
<213> ORGANISM: Artificial Sequence
<220> FEATURE:
<223> OTHER INFORMATION: corresponding amino acid to SEQ ID NO. 1

<400> SEQUENCE: 4

Ser Gly Gly Gly Thr Gln Pro Arg
1               5

<210> SEQ ID NO 5
<211> LENGTH: 8
<212> TYPE: PRT
<213> ORGANISM: Artificial Sequence
<220> FEATURE:
<223> OTHER INFORMATION: corresponding amino acid to SEQ ID NO. 2

<400> SEQUENCE: 5

Ser Ala Gly Gly Gly Gly Cys Ala
1               5

<210> SEQ ID NO 6
<211> LENGTH: 8
<212> TYPE: PRT
<213> ORGANISM: Artificial Sequence
<220> FEATURE:
<223> OTHER INFORMATION: corresponding amino acid to SEQ ID NO. 3

<400> SEQUENCE: 6

Ser Gly Gly Gly Thr Lys Pro Arg
1               5

<210> SEQ ID NO 7
<211> LENGTH: 27
<212> TYPE: DNA
<213> ORGANISM: Artificial Sequence
<220> FEATURE:
<223> OTHER INFORMATION: Primer

<400> SEQUENCE: 7
gaattcagct ggaggtggtg gatgtgc                                           27
```